US011738158B2

(12) United States Patent
Hebrank et al.

(10) Patent No.: US 11,738,158 B2
(45) Date of Patent: *Aug. 29, 2023

(54) ELECTRONIC BREATH ACTUATED IN-LINE DROPLET DELIVERY DEVICE AND METHODS OF USE

(71) Applicant: PNEUMA RESPIRATORY, INC., Boone, NC (US)

(72) Inventors: John H. Hebrank, Durham, NC (US); Charles Eric Hunter, Boone, NC (US); Christopher W. Maurer, Irvine, CA (US); Chengjie Li, Shenzhen (CN); Louis Thomas Germinario, Kingsport, TN (US)

(73) Assignee: Pneuma Respiratory, Inc., Boone, NC (US)

( * ) Notice: Subject to any disclaimer, the term of this patent is extended or adjusted under 35 U.S.C. 154(b) by 524 days.

This patent is subject to a terminal disclaimer.

(21) Appl. No.: 16/651,715

(22) PCT Filed: Oct. 4, 2018

(86) PCT No.: PCT/US2018/054417
§ 371 (c)(1),
(2) Date: Mar. 27, 2020

(87) PCT Pub. No.: WO2019/071008
PCT Pub. Date: Apr. 11, 2019

(65) Prior Publication Data
US 2020/0276398 A1 Sep. 3, 2020

Related U.S. Application Data

(60) Provisional application No. 62/732,455, filed on Sep. 17, 2018, provisional application No. 62/622,022,
(Continued)

(51) Int. Cl.
*A61M 11/00* (2006.01)
*A61M 15/00* (2006.01)
(52) U.S. Cl.
CPC ........ *A61M 11/005* (2013.01); *A61M 15/008* (2014.02); *A61M 15/0026* (2014.02);
(Continued)
(58) Field of Classification Search
CPC .. A61M 11/00; A61M 11/001; A61M 11/002; A61M 11/003; A61M 11/005;
(Continued)

(56) References Cited

U.S. PATENT DOCUMENTS 3,934,585 A 1/1976 Maurice
3,970,250 A 7/1976 Drews
(Continued)

FOREIGN PATENT DOCUMENTS

AU 2012258488 1/2013
CA 2364248 8/2006
(Continued)

OTHER PUBLICATIONS

Copley, "Understanding cascade impaction and its importance for inhaler testing," Copley Scientific, Copley White Paper [serial online], Jul. 2007 [retrieved on May 7, 2017]. Retrieved from the Internet: URL: http://www.copleyscientific.com/files/ww/articles/Understanding%20Cascade%20Impaction%20White%20Paper.pdf; 6 pp.
(Continued)

*Primary Examiner* — Joseph D. Boecker
*Assistant Examiner* — Brian T Khong
(74) *Attorney, Agent, or Firm* — Polsinelli PC

(57) ABSTRACT

An in-line droplet delivery device and related methods for delivering precise and repeatable dosages to a subject for pulmonary use is disclosed. The in-line droplet delivery
(Continued)

device includes a housing, a mouthpiece, a reservoir, an ejector mechanism, and at least one differential pressure sensor. The in-line droplet delivery device is automatically breath actuated by the user when the differential pressure sensor senses a predetermined pressure change within housing. The in-line droplet delivery device is then actuated to generate a plume of droplets having an average ejected particle diameter within the respirable size range, e.g, less than about 5-6 µm, so as to target the pulmonary system of the user. the droplet delivery device is configured in an in-line orientation in that the housing, its internal components, and various device components (e.g., the mouthpiece, air inlet flow element, etc.) are orientated in a substantially in-line or parallel configuration (e.g., along the airflow path) so as to form a small, hand-held device.

26 Claims, 29 Drawing Sheets

Related U.S. Application Data filed on Jan. 25, 2018, provisional application No. 62/575,165, filed on Oct. 20, 2017, provisional application No. 62/568,057, filed on Oct. 4, 2017.

(52) U.S. Cl.
CPC ............... *A61M 2205/3331* (2013.01); *A61M 2205/3592* (2013.01); *A61M 2205/502* (2013.01); *A61M 2205/581* (2013.01); *A61M 2205/583* (2013.01); *A61M 2205/587* (2013.01); *A61M 2205/8206* (2013.01)

(58) Field of Classification Search
CPC .............. A61M 15/00; A61M 15/0001; A61M 15/001; A61M 15/0021; A61M 15/0025; A61M 15/0026; A61M 15/008; A61M 15/0085; A61M 15/0095; A61M 15/0071; A61M 15/0028; A61M 15/0061
See application file for complete search history.

(56) References Cited

U.S. PATENT DOCUMENTS

| | | |
|---|---|---|
| 5,021,701 A | 6/1991 | Takahashi et al. |
| 5,164,740 A | 11/1992 | Ivri |
| 5,363,842 A | 11/1994 | Mishelevich et al. |
| 5,487,378 A * | 1/1996 | Robertson ......... A61M 15/0015 128/200.14 |
| 5,497,763 A | 3/1996 | Lloyd et al. |
| 5,586,550 A | 12/1996 | Ivri et al. |
| 5,607,410 A | 3/1997 | Branch |
| 5,630,793 A | 5/1997 | Rowe |
| 5,758,637 A | 6/1998 | Ivri et al. |
| 5,826,570 A | 10/1998 | Goodman et al. |
| 5,828,394 A | 10/1998 | Khuri-Yakub et al. |
| 5,881,716 A | 3/1999 | Wirch et al. |
| 5,884,620 A | 3/1999 | Gonda et al. |
| 5,894,841 A | 4/1999 | Voges |
| 5,906,202 A | 5/1999 | Schuster et al. |
| 5,938,117 A | 8/1999 | Ivri |
| 5,979,247 A | 11/1999 | Kizawa |
| 6,011,062 A | 1/2000 | Schneider et al. |
| 6,062,212 A | 5/2000 | Davison et al. |
| 6,071,498 A | 6/2000 | Narodylo et al. |
| 6,085,740 A | 7/2000 | Ivri et al. |
| 6,158,431 A | 12/2000 | Poole |
| 6,196,219 B1 | 3/2001 | Hess et al. |
| 6,235,177 B1 | 5/2001 | Borland et al. |
| 6,358,058 B1 | 3/2002 | Strupat et al. |
| 6,443,146 B1 | 9/2002 | Voges |
| 6,511,718 B1 | 1/2003 | Paz de Araujo et al. |
| 6,615,826 B1 | 9/2003 | Gabrio et al. |
| 6,629,524 B1 | 10/2003 | Goodall et al. |
| 6,637,430 B1 | 10/2003 | Voges et al. |
| 6,896,910 B2 | 5/2005 | Kim et al. |
| 6,978,941 B2 | 12/2005 | Litherland et al. |
| 6,981,499 B2 | 1/2006 | Anderson et al. |
| 7,131,599 B2 | 11/2006 | Katase |
| 7,191,777 B2 | 3/2007 | Brand et al. |
| 7,198,044 B2 | 4/2007 | Trueba |
| 7,219,664 B2 | 5/2007 | Ruckdeschel et al. |
| 7,628,339 B2 | 12/2009 | Ivri et al. |
| 7,648,957 B2 | 1/2010 | Heyden et al. |
| 7,708,011 B2 | 5/2010 | Hochrainer et al. |
| 7,883,031 B2 | 2/2011 | Collins, Jr. et al. |
| 7,900,625 B2 | 3/2011 | Kleinstreuer et al. |
| 7,954,486 B2 | 6/2011 | Papania et al. |
| 7,976,140 B2 | 7/2011 | Umeda |
| 8,012,136 B2 | 9/2011 | Collins, Jr. et al. |
| 8,367,734 B1 | 2/2013 | Gao et al. |
| 8,474,452 B2 | 7/2013 | Gumaste et al. |
| 8,545,463 B2 | 10/2013 | Collins, Jr. et al. |
| 8,555,874 B2 | 10/2013 | Fink et al. |
| 8,616,195 B2 | 12/2013 | Power et al. |
| 8,684,980 B2 | 4/2014 | Hunter et al. |
| 8,733,935 B2 | 5/2014 | Ballou, Jr. et al. |
| 8,753,308 B2 | 6/2014 | Palmer et al. |
| 8,936,021 B2 | 1/2015 | Collins, Jr. |
| 8,985,100 B2 | 3/2015 | Minocchieri et al. |
| 9,022,027 B2 | 5/2015 | Addington et al. |
| 9,087,145 B2 | 7/2015 | Ballou, Jr. et al. |
| 9,227,029 B2 | 1/2016 | Addington et al. |
| 9,242,054 B2 | 1/2016 | Fink et al. |
| 9,352,108 B1 | 5/2016 | Reed et al. |
| 9,452,274 B2 | 9/2016 | Addington et al. |
| 9,463,486 B2 | 10/2016 | Wilkerson et al. |
| 9,539,604 B2 | 1/2017 | Wilkerson et al. |
| 9,956,360 B2 | 5/2018 | Germinario et al. |
| 9,962,507 B2 | 5/2018 | Germinario et al. |
| 10,449,314 B2 | 10/2019 | Germinario et al. |
| 10,525,220 B2 | 1/2020 | Hunter et al. |
| 10,568,543 B2 | 2/2020 | Yan |
| 10,857,310 B2 | 12/2020 | Muellinger et al. |
| 10,898,666 B2 | 1/2021 | Germinario et al. |
| 2002/0002975 A1 | 1/2002 | Power |
| 2002/0032387 A1 | 3/2002 | Geva et al. |
| 2002/0046750 A1 | 4/2002 | Gonda et al. |
| 2002/0071871 A1 | 6/2002 | Snyder et al. |
| 2002/0077369 A1* | 6/2002 | Noolandi .......... A61M 15/0085 128/200.14 |
| 2002/0121274 A1 | 9/2002 | Borland et al. |
| 2003/0062042 A1 | 4/2003 | Wensley et al. |
| 2003/0072717 A1 | 4/2003 | Reinhold et al. |
| 2003/0098022 A1 | 5/2003 | Nakao et al. |
| 2003/0101991 A1 | 6/2003 | Trueba |
| 2003/0127538 A1 | 7/2003 | Patel et al. |
| 2003/0140921 A1 | 7/2003 | Smith et al. |
| 2003/0150445 A1 | 8/2003 | Power et al. |
| 2003/0196654 A1 | 10/2003 | Stein |
| 2003/0205229 A1 | 11/2003 | Crockford et al. |
| 2004/0009231 A1 | 1/2004 | Jackson et al. |
| 2004/0045547 A1 | 3/2004 | Yamamoto et al. |
| 2004/0084044 A1 | 5/2004 | Childers et al. |
| 2004/0139963 A1 | 7/2004 | Ivri et al. |
| 2004/0195403 A1 | 10/2004 | Atterybury et al. |
| 2004/0215157 A1 | 10/2004 | Peclat et al. |
| 2004/0256487 A1 | 12/2004 | Collins, Jr. et al. |
| 2005/0011514 A1 | 1/2005 | Power et al. |
| 2005/0077315 A1 | 4/2005 | Pavlu et al. |
| 2005/0121025 A1 | 6/2005 | Gamard et al. |
| 2005/0150489 A1 | 7/2005 | Dunfield et al. |
| 2005/0172476 A1 | 8/2005 | Stone et al. |
| 2005/0172958 A1 | 8/2005 | Singer et al. |
| 2005/0217666 A1* | 10/2005 | Fink ..................... A61P 33/02 128/200.14 |
| 2005/0224075 A1 | 10/2005 | Childers et al. |
| 2005/0236501 A1 | 10/2005 | Zimlich, Jr. et al. |
| 2007/0023036 A1 | 2/2007 | Grychowski et al. |
| 2007/0044793 A1 | 3/2007 | Kleinstreuer et al. |

(56) References Cited

U.S. PATENT DOCUMENTS

| | | |
|---|---|---|
| 2007/0083677 A1 | 4/2007 | Cecka et al. |
| 2007/0119968 A1 | 5/2007 | Collins, Jr. et al. |
| 2007/0119969 A1 | 5/2007 | Collins et al. |
| 2007/0125370 A1 | 6/2007 | Denyer et al. |
| 2007/0157931 A1 | 7/2007 | Parker et al. |
| 2007/0240714 A1 | 10/2007 | Dunne et al. |
| 2007/0248645 A1 | 10/2007 | Bague et al. |
| 2007/0267010 A1 | 11/2007 | Fink et al. |
| 2008/0000470 A1 | 1/2008 | Minocchieri et al. |
| 2008/0059228 A1 | 3/2008 | Bossi et al. |
| 2008/0142010 A1 | 6/2008 | Weaver et al. |
| 2008/0243050 A1 | 10/2008 | Power et al. |
| 2008/0271732 A1 | 11/2008 | Weaver et al. |
| 2008/0283057 A1 | 11/2008 | Rohrschneider et al. |
| 2008/0295827 A1 | 12/2008 | Kobayashi |
| 2008/0308096 A1 | 12/2008 | Borgschulte et al. |
| 2009/0038610 A1 | 2/2009 | Bogh et al. |
| 2009/0093772 A1 | 4/2009 | Genosar et al. |
| 2009/0107492 A1 | 4/2009 | Ooida |
| 2009/0114218 A1 | 5/2009 | Veatch |
| 2009/0114742 A1 | 5/2009 | Collins, Jr. |
| 2009/0118243 A1 | 5/2009 | Gjorstrup |
| 2009/0134235 A1 | 5/2009 | Ivri |
| 2009/0167812 A1 | 7/2009 | Asai et al. |
| 2009/0192443 A1 | 7/2009 | Collins, Jr. |
| 2009/0212133 A1 | 8/2009 | Collins, Jr. |
| 2009/0235925 A1 | 9/2009 | Power et al. |
| 2009/0270752 A1 | 10/2009 | Coifman |
| 2009/0272818 A1 | 11/2009 | Valpey, III et al. |
| 2009/0314292 A1 | 12/2009 | Overfield et al. |
| 2009/0317496 A1 | 12/2009 | Park et al. |
| 2010/0037894 A1 | 2/2010 | Rouse et al. |
| 2010/0078013 A1 | 4/2010 | Power et al. |
| 2010/0089395 A1 | 4/2010 | Power et al. |
| 2010/0156995 A1 | 6/2010 | Kanda et al. |
| 2010/0181387 A1* | 7/2010 | Zaffaroni ............ A61M 11/042 239/128 |
| 2010/0222752 A1 | 9/2010 | Collins, Jr. et al. |
| 2010/0273895 A1 | 10/2010 | Stinchcomb et al. |
| 2010/0282247 A1 | 11/2010 | Kadrichu et al. |
| 2011/0108025 A1 | 5/2011 | Fink et al. |
| 2011/0114090 A1 | 5/2011 | Piper |
| 2011/0230820 A1 | 9/2011 | Lillis et al. |
| 2011/0253139 A1 | 10/2011 | Guthrie et al. |
| 2011/0253805 A1 | 10/2011 | Lee |
| 2012/0037154 A1 | 2/2012 | Gallem et al. |
| 2012/0048265 A1 | 3/2012 | Smaldone |
| 2012/0266878 A1 | 10/2012 | Watanabe et al. |
| 2012/0291781 A1 | 11/2012 | Kaufmann et al. |
| 2013/0064777 A1 | 3/2013 | Tamarkin et al. |
| 2013/0079732 A1 | 3/2013 | Burt et al. |
| 2013/0150812 A1 | 6/2013 | Hunter et al. |
| 2013/0172830 A1 | 7/2013 | Hunter et al. |
| 2013/0239956 A1 | 9/2013 | Schulz et al. |
| 2013/0267864 A1 | 10/2013 | Addington et al. |
| 2013/0284165 A1 | 10/2013 | Krimsky |
| 2013/0299607 A1 | 11/2013 | Wilkerson et al. |
| 2013/0319404 A1 | 12/2013 | Feriani et al. |
| 2013/0327323 A1 | 12/2013 | Rubin |
| 2013/0330400 A1 | 12/2013 | Perkins et al. |
| 2013/0334335 A1 | 12/2013 | Wilkerson et al. |
| 2013/0334339 A1 | 12/2013 | Xu |
| 2014/0037735 A1 | 2/2014 | Montgomery |
| 2014/0116426 A1 | 5/2014 | Mullinger et al. |
| 2014/0187969 A1 | 7/2014 | Hunter et al. |
| 2014/0190496 A1 | 7/2014 | Wensley et al. |
| 2014/0213925 A1 | 7/2014 | Chan et al. |
| 2014/0230817 A1 | 8/2014 | Richardson |
| 2014/0231538 A1 | 8/2014 | Tabata et al. |
| 2014/0283859 A1 | 9/2014 | Minskoff et al. |
| 2014/0336618 A1 | 11/2014 | Wilkerson et al. |
| 2015/0018694 A1 | 1/2015 | Gomo |
| 2015/0101596 A1 | 4/2015 | Hogan |
| 2015/0136129 A1 | 5/2015 | Mehadevan et al. |
| 2015/0136155 A1 | 5/2015 | Verleur et al. |
| 2015/0164375 A1 | 6/2015 | Schindhelm et al. |
| 2015/0174348 A1 | 6/2015 | Tunnell et al. |
| 2015/0196060 A1 | 7/2015 | Wensley et al. |
| 2015/0273165 A1 | 10/2015 | Hadash |
| 2015/0283339 A1* | 10/2015 | Mahadevan .......... A61M 16/12 128/203.14 |
| 2015/0328151 A1 | 11/2015 | Ballou, Jr. et al. |
| 2015/0352301 A1 | 12/2015 | Stedman et al. |
| 2016/0001018 A1 | 1/2016 | Fink et al. |
| 2016/0001019 A1 | 1/2016 | Fink et al. |
| 2016/0082208 A1 | 3/2016 | Ballam et al. |
| 2016/0106341 A1 | 4/2016 | Adam et al. |
| 2016/0129182 A1 | 5/2016 | Schuster et al. |
| 2016/0166768 A1 | 6/2016 | Edwards et al. |
| 2016/0213864 A1 | 7/2016 | Eilat et al. |
| 2016/0213866 A1 | 7/2016 | Tan |
| 2016/0245830 A1 | 8/2016 | Mace et al. |
| 2016/0310982 A1 | 10/2016 | Von Hollen |
| 2016/0325055 A1 | 11/2016 | Cameron |
| 2016/0354557 A1 | 12/2016 | McPherson Allnutt et al. |
| 2017/0007449 A1 | 1/2017 | Nielsen |
| 2017/0035924 A1 | 2/2017 | Yang et al. |
| 2017/0039344 A1 | 2/2017 | Bitran et al. |
| 2017/0106153 A1 | 4/2017 | Davidson et al. |
| 2017/0106155 A1 | 4/2017 | Reed et al. |
| 2017/0128677 A1 | 5/2017 | Eilat et al. |
| 2017/0158776 A1 | 6/2017 | Feltquate et al. |
| 2017/0203058 A1 | 7/2017 | Davidson et al. |
| 2017/0203323 A1 | 7/2017 | Gschwind et al. |
| 2017/0224706 A1 | 8/2017 | Surber |
| 2017/0270260 A1 | 9/2017 | Shetty et al. |
| 2017/0274163 A1 | 9/2017 | Oliveras et al. |
| 2017/0304565 A1 | 10/2017 | Allosery |
| 2017/0304566 A1 | 10/2017 | Allosery |
| 2017/0319796 A1 | 11/2017 | Germinario et al. |
| 2017/0319797 A1 | 11/2017 | Germinario et al. |
| 2017/0333646 A1 | 11/2017 | Hemy et al. |
| 2018/0021528 A1 | 1/2018 | Hsieh et al. |
| 2018/0021530 A1* | 1/2018 | Fink .................... A61M 15/002 128/200.16 |
| 2018/0056018 A1 | 3/2018 | Canvin et al. |
| 2018/0116871 A1 | 5/2018 | Hunter et al. |
| 2018/0193175 A1 | 7/2018 | Bluecher et al. |
| 2018/0317557 A1 | 11/2018 | Monsees et al. |
| 2018/0344955 A1 | 12/2018 | Germinario et al. |
| 2018/0369515 A1 | 12/2018 | Germinario et al. |
| 2019/0117907 A1 | 4/2019 | Germinario et al. |
| 2019/0125985 A1 | 5/2019 | Germinario et al. |
| 2019/0125986 A1 | 5/2019 | Germinario et al. |
| 2019/0125987 A1 | 5/2019 | Germinario et al. |
| 2019/0134330 A1 | 5/2019 | Germinario et al. |
| 2019/0224426 A1 | 7/2019 | Farina et al. |
| 2019/0343793 A1 | 11/2019 | Gunther et al. |
| 2019/0358420 A1 | 11/2019 | Hunter et al. |
| 2020/0060346 A1 | 2/2020 | Danek |
| 2020/0147325 A1 | 5/2020 | Wilson et al. |
| 2020/0230329 A1 | 7/2020 | Danek |
| 2020/0246556 A1 | 8/2020 | Osoegawa et al. |
| 2020/0289770 A1 | 9/2020 | Hebrank et al. |
| 2020/0315842 A1 | 10/2020 | Palanker et al. |
| 2020/0345588 A1 | 11/2020 | Merrell et al. |
| 2020/0353186 A1 | 11/2020 | Hebrank et al. |
| 2021/0106772 A1 | 4/2021 | Hebrank et al. |
| 2021/0236745 A1 | 8/2021 | Germinario et al. |
| 2021/0275760 A1 | 9/2021 | Hunter et al. |
| 2022/0001122 A1 | 1/2022 | Hunter et al. |
| 2022/0296823 A1 | 9/2022 | Hebrank et al. |

FOREIGN PATENT DOCUMENTS

| | | |
|---|---|---|
| CH | 715947 | 11/2020 |
| CN | 1788806 | 6/2006 |
| CN | 104511072 | 4/2015 |
| CN | 204995458 | 1/2016 |
| CN | 205019058 | 2/2016 |
| EP | 2724741 | 4/2014 |
| JP | H11-042219 | 2/1999 |
| JP | 2003-265994 | 9/2003 |
| JP | 2006-68508 | 3/2006 |

(56) References Cited

FOREIGN PATENT DOCUMENTS

| | | |
|---|---|---|
| KR | 10-2019-122453 | 10/2019 |
| WO | WO 93/12823 | 7/1993 |
| WO | WO 96/09846 | 4/1996 |
| WO | WO 96/14163 | 5/1996 |
| WO | WO 98/48873 | 11/1998 |
| WO | WO 00/10634 | 3/2000 |
| WO | WO 00/47335 | 8/2000 |
| WO | WO 00/50112 | 8/2000 |
| WO | WO 01/85244 | 11/2001 |
| WO | WO 01/87378 | 11/2001 |
| WO | WO 03/020349 | 3/2003 |
| WO | WO 03/059413 | 7/2003 |
| WO | WO 2004/078025 | 9/2004 |
| WO | WO 2006/013952 | 2/2006 |
| WO | WO 2006/083014 | 8/2006 |
| WO | WO 2006/102345 | 9/2006 |
| WO | WO 2006/108558 | 10/2006 |
| WO | WO 2007/107160 | 9/2007 |
| WO | WO 2008/056986 | 5/2008 |
| WO | WO 2008/058941 | 5/2008 |
| WO | WO 2008/116165 | 9/2008 |
| WO | WO 2009/012371 | 1/2009 |
| WO | WO 2009/111612 | 9/2009 |
| WO | WO 2010/065452 | 6/2010 |
| WO | WO 2011/042212 | 4/2011 |
| WO | WO 2011/083377 | 7/2011 |
| WO | WO 2011/091268 | 7/2011 |
| WO | WO 2011/163272 | 12/2011 |
| WO | WO 2012/026963 | 3/2012 |
| WO | WO 2013/098334 | 7/2013 |
| WO | WO 2013/158352 | 10/2013 |
| WO | WO 2013/158967 | 10/2013 |
| WO | WO 2013/173321 | 11/2013 |
| WO | WO 2014/147550 | 9/2014 |
| WO | WO 2015/004554 | 1/2015 |
| WO | WO 2015/106150 | 7/2015 |
| WO | WO 2015/136529 | 9/2015 |
| WO | WO 2015/176033 | 11/2015 |
| WO | WO 2015/191478 | 12/2015 |
| WO | WO 2015/191481 | 12/2015 |
| WO | WO 2016/001923 | 1/2016 |
| WO | WO 2016/001924 | 1/2016 |
| WO | WO 2016/003738 | 1/2016 |
| WO | WO 2017/015303 | 1/2017 |
| WO | WO 2017/056103 | 4/2017 |
| WO | WO 2018/213834 | 11/2018 |
| WO | WO 2019/079461 | 4/2019 |
| WO | WO 2019/136437 | 7/2019 |
| WO | WO 2019/219865 | 11/2019 |
| WO | WO 2020/072478 | 4/2020 |
| WO | WO 2020/141424 | 7/2020 |
| WO | WO 2020/154497 | 7/2020 |
| WO | WO 2020/227717 | 11/2020 |
| WO | WO 2020/264501 | 12/2020 |
| WO | WO 2021/090135 | 5/2021 |
| WO | WO 2021/203038 | 10/2021 |
| WO | WO 2022/226407 | 10/2022 |
| WO | WO 2023/064477 | 4/2023 |

OTHER PUBLICATIONS

Kharitonov, "Exhaled markers of inflammatory lung diseases: ready for routine monitoring?" *Swiss Med Wkly*, 2004; 134: 175-192.

Breeders et al., "Inhalation Profiles in Asthmatics and COPD Patients: Reproducibility and Effect of Instruction," *Journal of Aerosol Medicine*, vol. 16, No. 2, 2003, 131-141.

Taube et al., "Use of a portable device to record maximum inspiratory flow in relation to dyspnea in patients with COPD," *Respiratory Medicine*, 2011, 105, 316-312.

Steller, "Microcontroller Based Diagnostic Smart Inhaler," University of Cincinnati, Dec. 7, 2014, 63 pages.

Carvalho et al., "The function and performance of aqueous aerosol devices for inhalation therapy," Journal of Pharmacy and Pharmacology, vol. 68, No. 5, Apr. 8, 2016, pp. 556-578.

Pneuma Respiratory, Digitally breath-actuated inhaler device with precision droplet ejector technology and digital dose confidence. Available on Mar. 18, 2017 [retrieved on Jun. 30, 2017]. Retrieved from the Internet: URL: https://pneumarespiratory.com/. 3 pp.

* cited by examiner

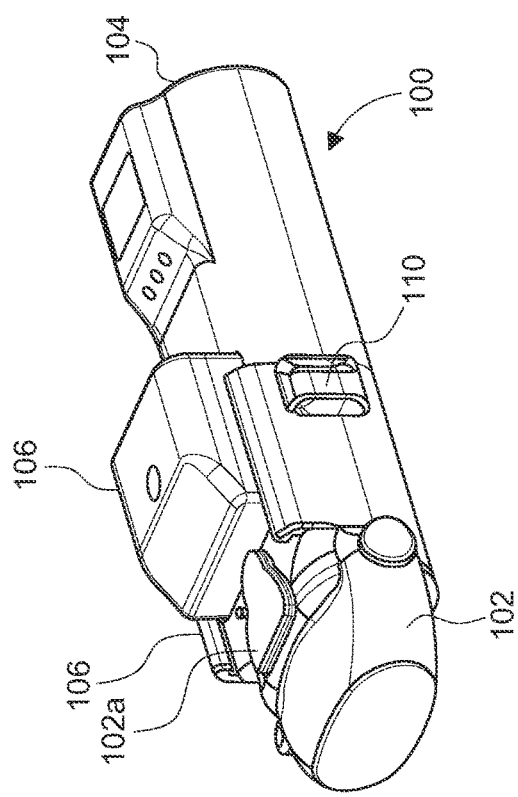
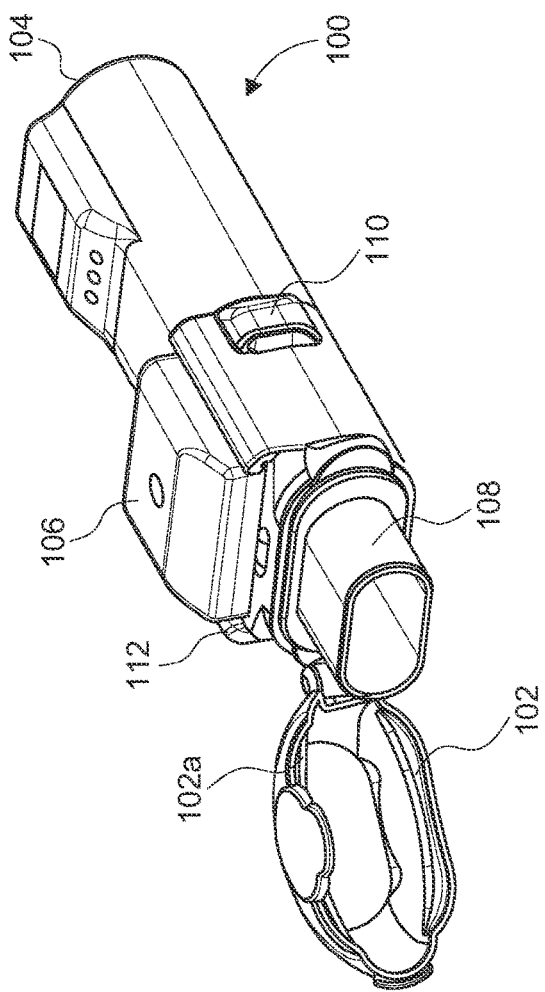

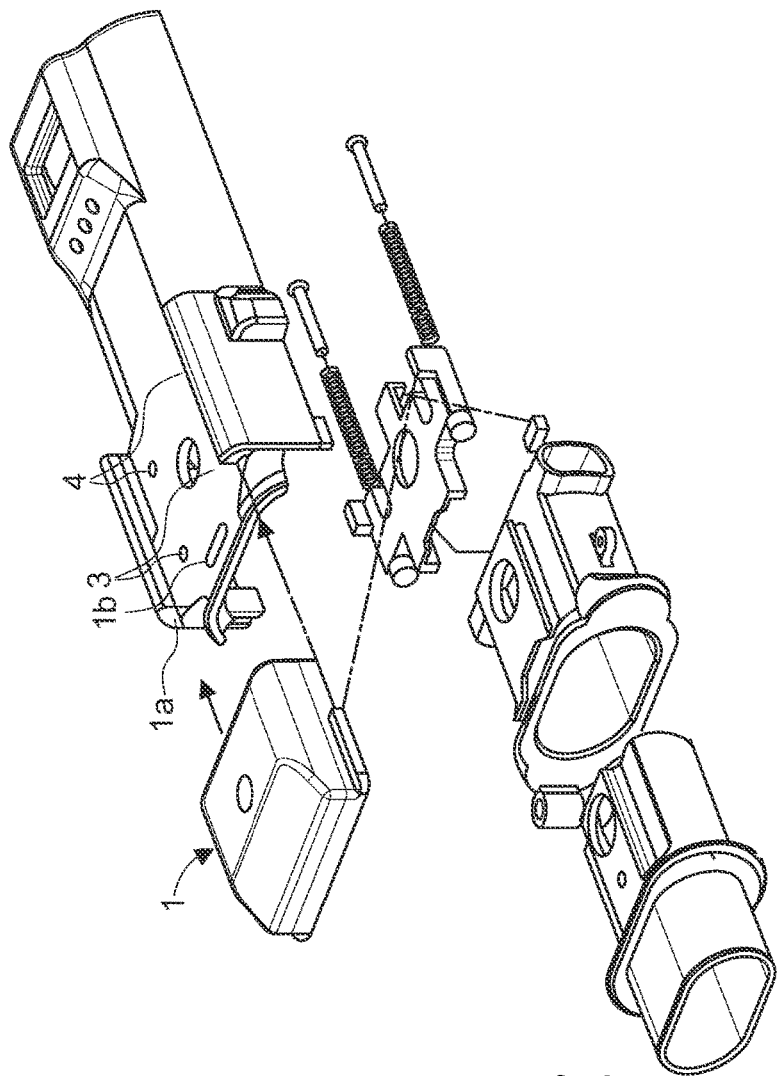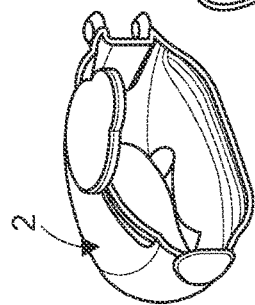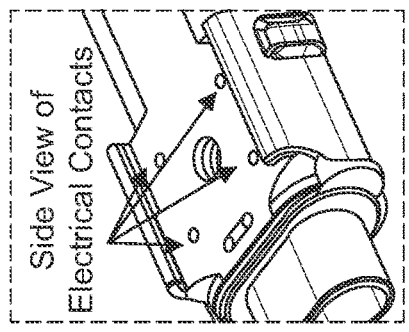
FIG. 3A-1
FIG. 3A-2

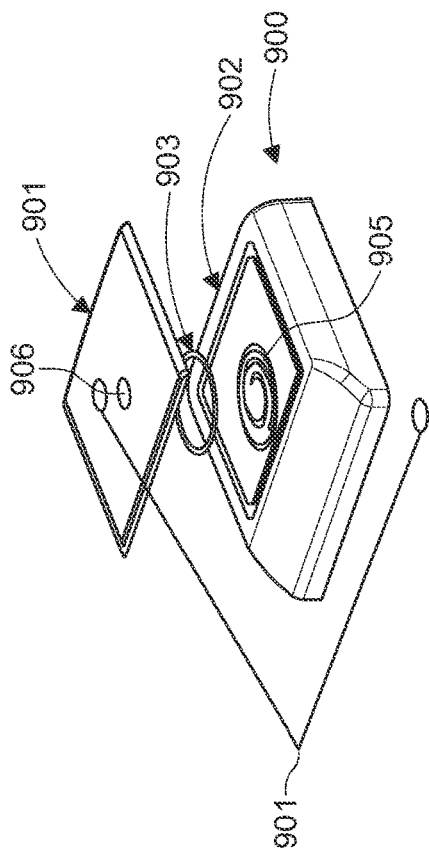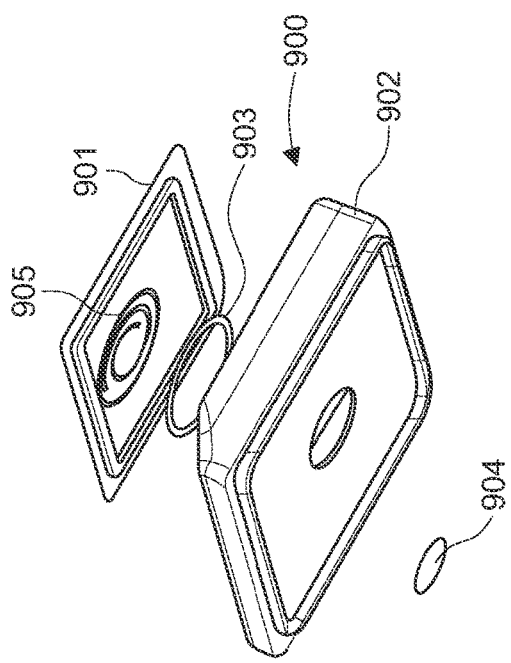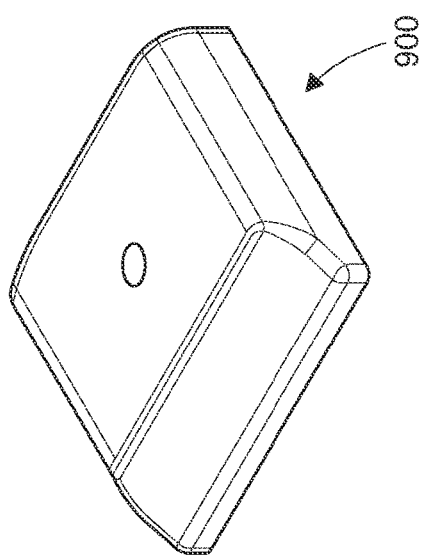
FIG. 9B
FIG. 9C
FIG. 9A

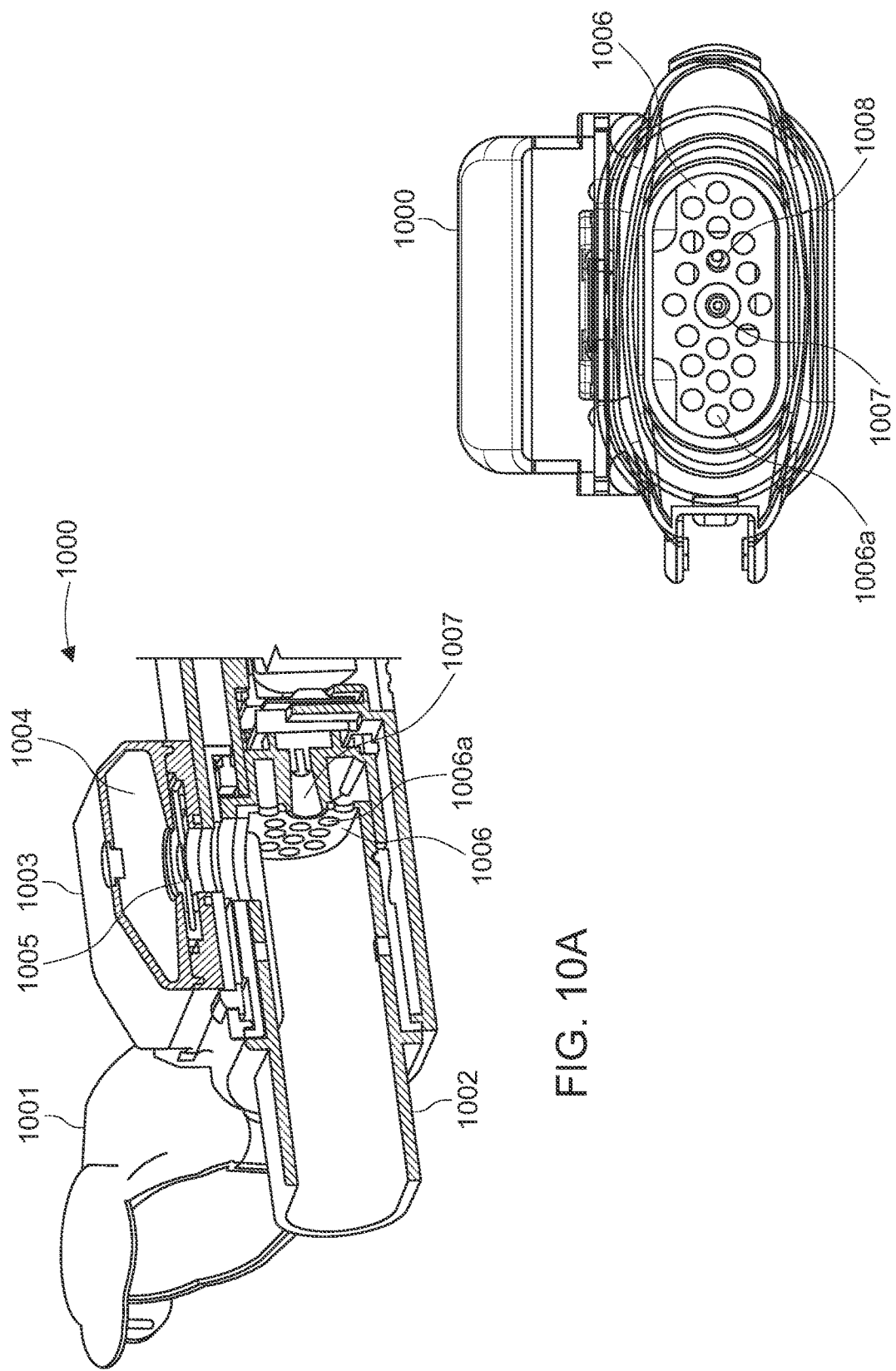

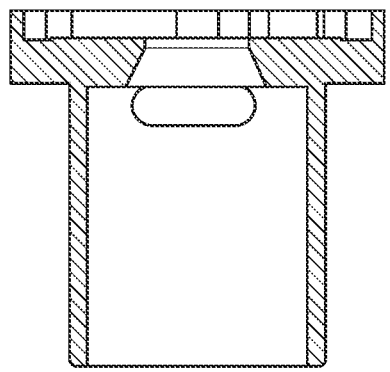
FIG. 14C
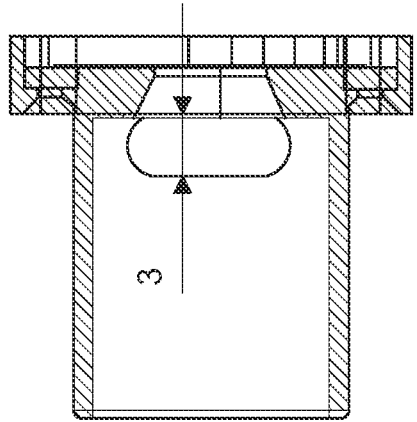
FIG. 14D
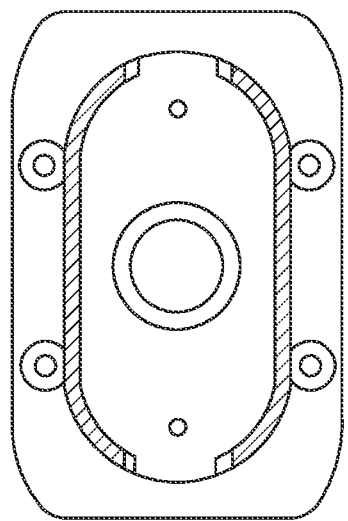
FIG. 14B
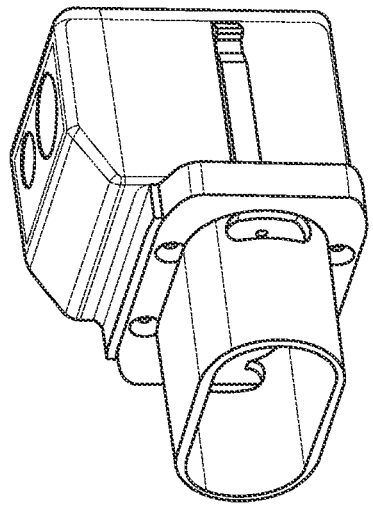
FIG. 14A
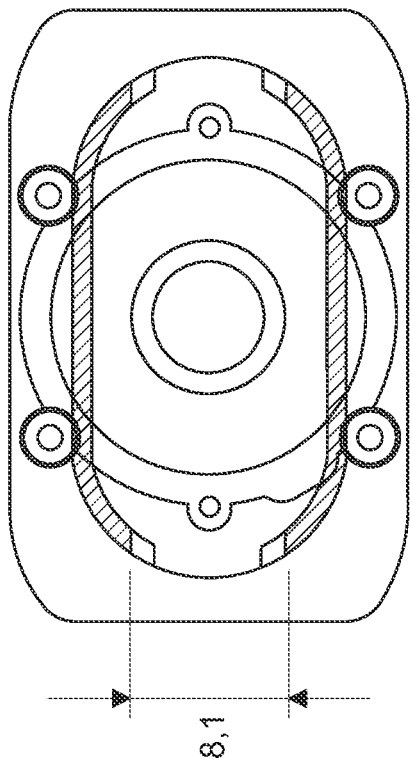

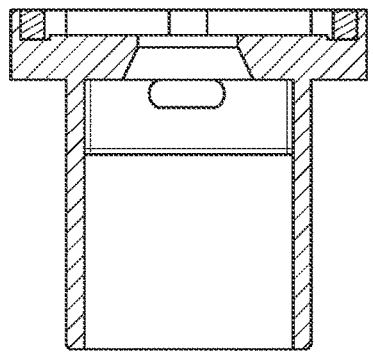
FIG. 16C
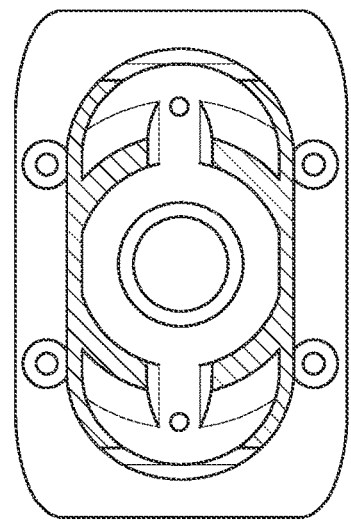
FIG. 16B
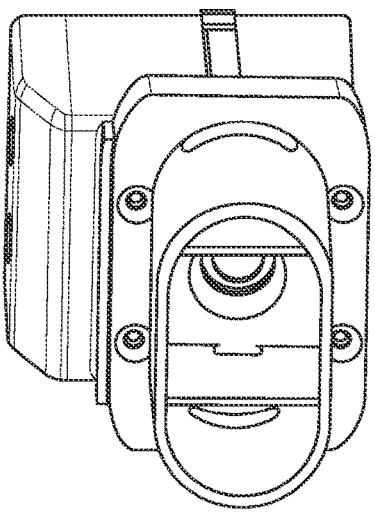
FIG. 16A
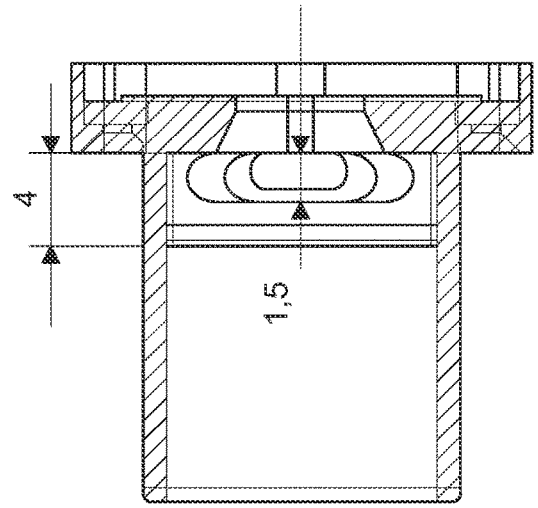
FIG. 16D
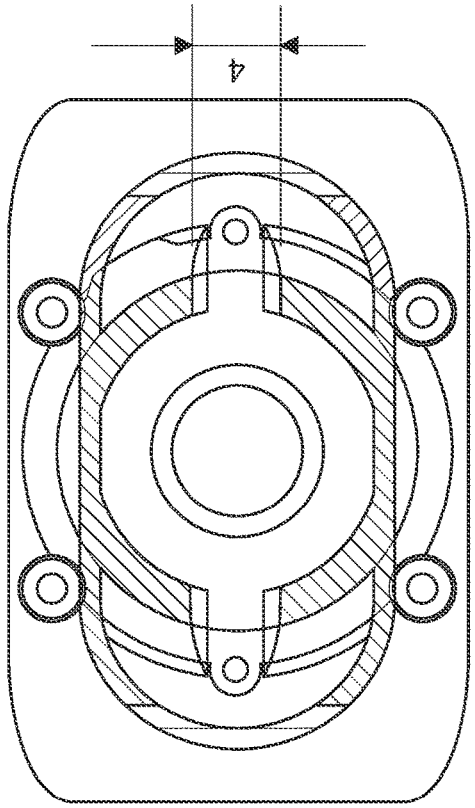

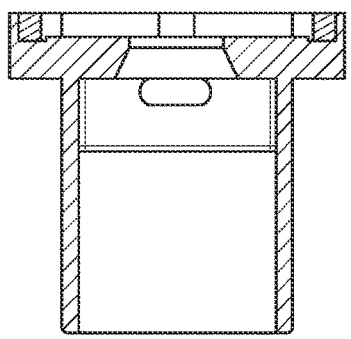
FIG. 17C
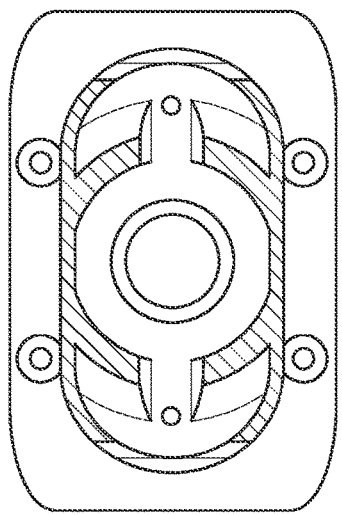
FIG. 17B
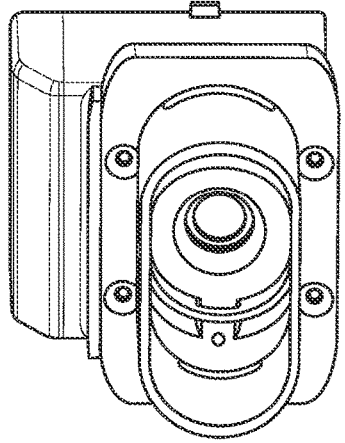
FIG. 17A
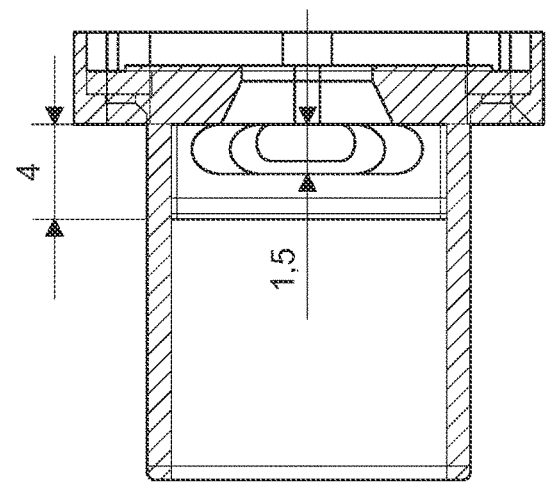
FIG. 17D
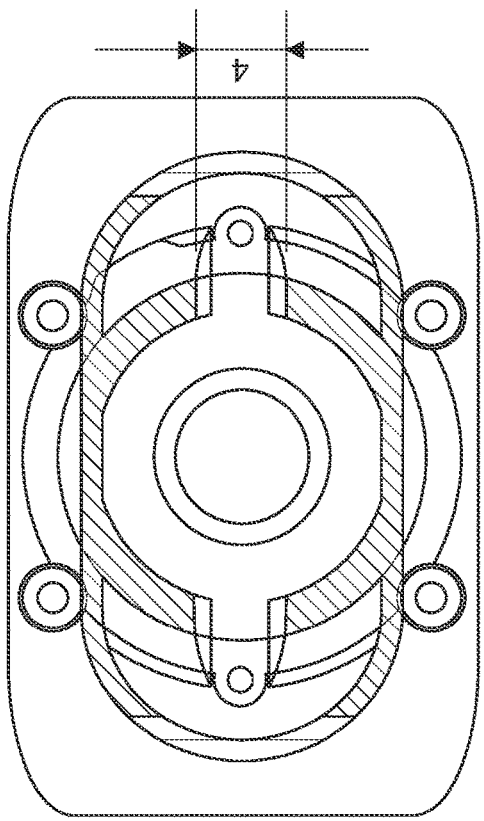

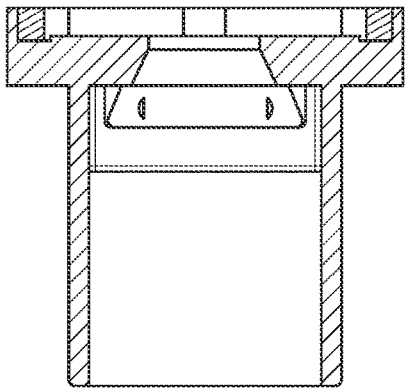
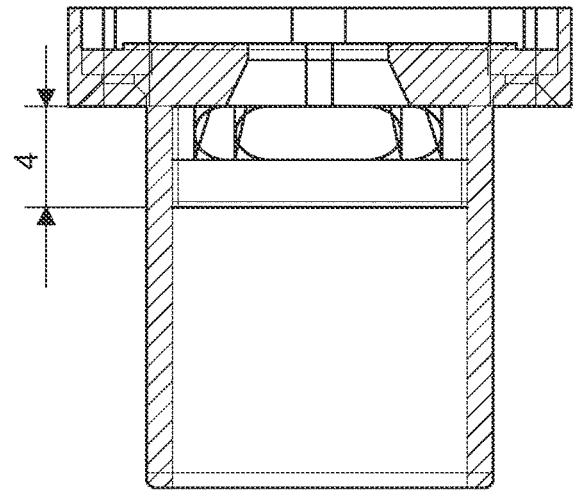
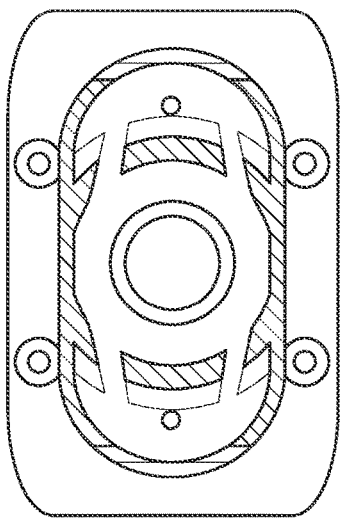
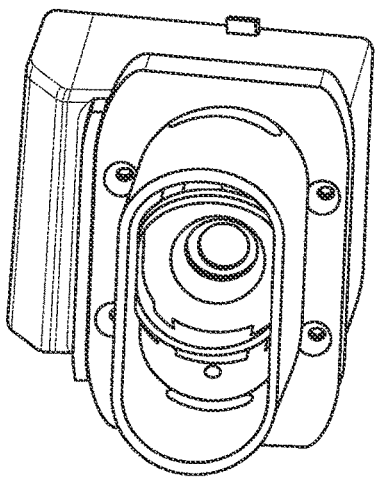
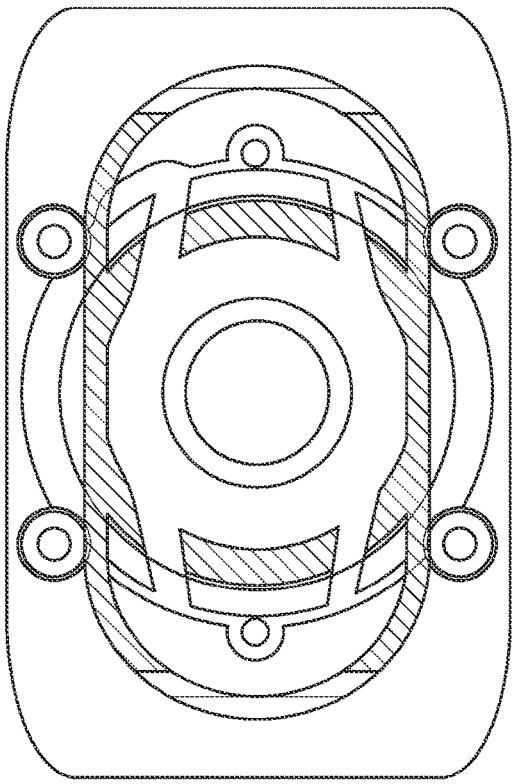
FIG. 18C
FIG. 18D
FIG. 18B
FIG. 18A

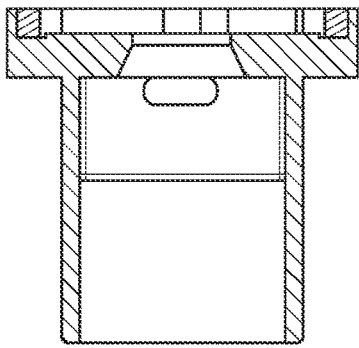
FIG. 19C
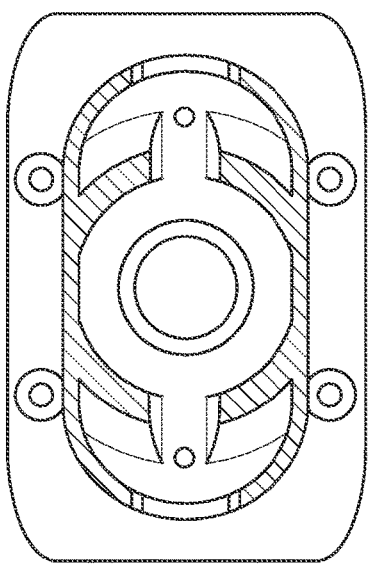
FIG. 19B
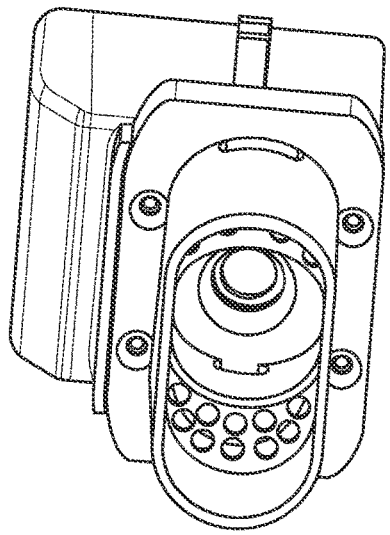
FIG. 19A
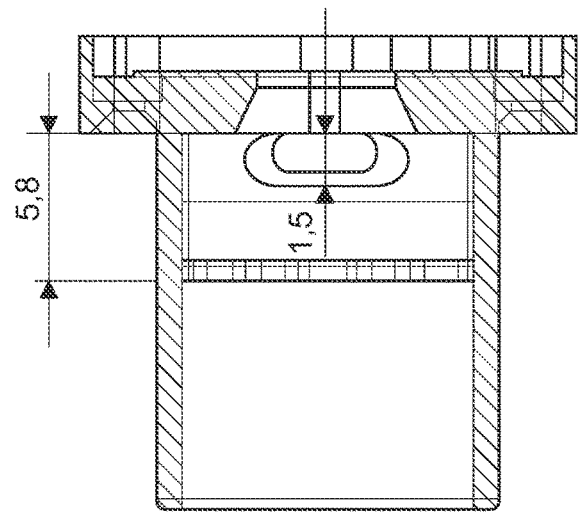
FIG. 19D
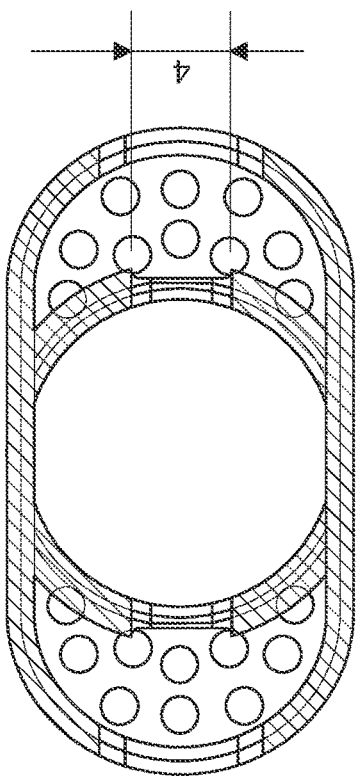

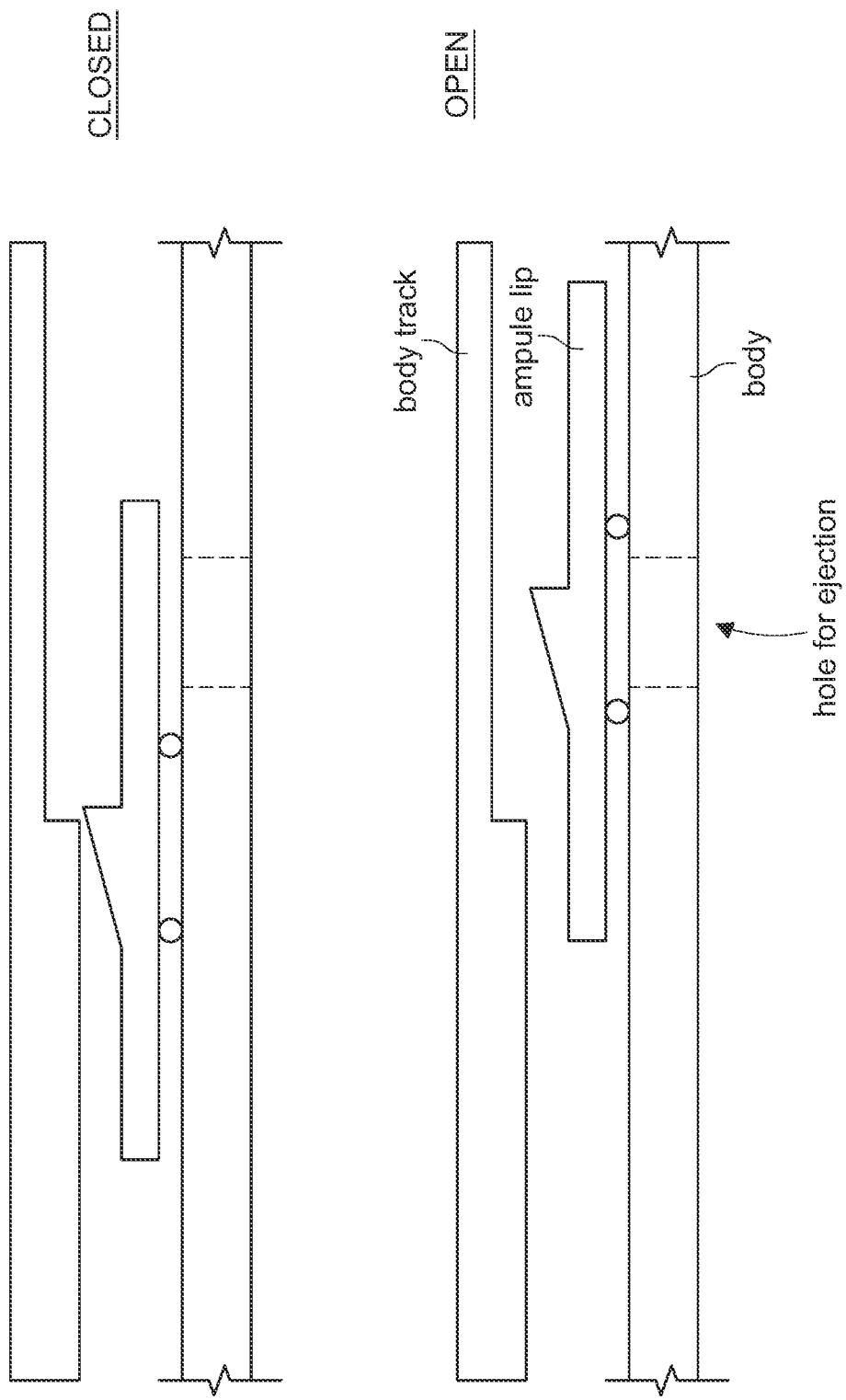

ELECTRONIC BREATH ACTUATED IN-LINE DROPLET DELIVERY DEVICE AND METHODS OF USE

RELATED APPLICATIONS

The present application claims benefit under 35 U.S.C. § 119 of U.S. Provisional Patent Application No. 62/568,057, filed Oct. 4, 2017, entitled "ELECTRONIC BREATH ACTUATED IN-LINE DROPLET DELIVERY DEVICE AND METHODS OF USE", U.S. Provisional Patent Application No. 62/575,165, filed Oct. 20, 2017, entitled "ELECTRONIC BREATH ACTUATED IN-LINE DROPLET DELIVERY DEVICE AND METHODS OF USE", U.S. Provisional Patent Application No. 62/622,022, filed Jan. 25, 2018, entitled "ELECTRONIC BREATH ACTUATED IN-LINE DROPLET DELIVERY DEVICE AND METHODS OF USE", and U.S. Provisional Patent Application No. 62/732,455, filed Sep. 17, 2018, entitled "ELECTRONIC BREATH ACTUATED IN-LINE DROPLET DELIVERY DEVICE AND METHODS OF USE", the contents of which are each herein incorporated by reference in their entireties.

FIELD OF THE INVENTION

This disclosure relates to droplet delivery devices and more specifically to droplet delivery devices for the delivery of fluids to the pulmonary system.

BACKGROUND OF THE INVENTION

The use of aerosol generating devices for the treatment of a variety of respiratory diseases is an area of large interest. Inhalation provides for the delivery of aerosolized drugs to treat asthma, COPD and site-specific conditions, with reduced systemic adverse effects. A major challenge is providing a device that delivers an accurate, consistent, and verifiable dose, with a droplet size that is suitable for successful delivery of medication to the targeted lung passageways.

Dose verification, delivery and inhalation of the correct dose at prescribed times is important. Getting patients to use inhalers correctly is also a major problem. A need exists to insure that patients correctly use inhalers and that they administer the proper dose at prescribed times. Problems emerge when patients misuse or incorrectly administer a dose of their medication. Unexpected consequences occur when the patient stops taking medications, owing to not feeling any benefit, or when not seeing expected benefits or overuse the medication and increase the risk of over dosage. Physicians also face the problem of how to interpret and diagnose the prescribed treatment when the therapeutic result is not obtained.

Currently most inhaler systems such as metered dose inhalers (MDI) and pressurized metered dose inhalers (p-MDI) or pneumatic and ultrasonic-driven devices generally produce droplets with high velocities and a wide range of droplet sizes including large droplet that have high momentum and kinetic energy. Droplets and aerosols with such high momentum do not reach the distal lung or lower pulmonary passageways, but rather are deposited in the mouth and throat. As a result, larger total drug doses are required to achieve the desired deposition in targeted pulmonary areas. These large doses increase the probability of unwanted side effects.

Aerosol plumes generated from current aerosol delivery systems, as a result of their high ejection velocities and the rapid expansion of the drug carrying propellant, may lead to localized cooling and subsequent condensation, deposition and crystallization of drug onto the device surfaces. Blockage of device surfaces by deposited drug residue is also problematic.

This phenomenon of surface condensation is also a challenge for existing vibrating mesh or aperture plate nebulizers that are available on the market. In these systems, in order to prevent a buildup of drug onto mesh aperture surfaces, manufacturers require repeated washing and cleaning, as well as disinfection after a single use in order to prevent possible microbiological contamination. Other challenges include delivery of viscous drugs and suspensions that can clog the apertures or pores and lead to inefficiency or inaccurate drug delivery to patients or render the device inoperable. Also, the use of detergents or other cleaning or sterilizing fluids may damage the ejector mechanism or other parts of the nebulizer and lead to uncertainty as to the ability of the device to deliver a correct dose to the patient or state of performance of the device.

Accordingly, there is a need for a droplet delivery device that delivers droplets of a suitable size range, avoids surface fluid deposition and blockage of apertures, with a dose that is verifiable, and provides feedback regarding correct and consistent usage of the device to patients and professionals such as physicians, pharmacists or therapists.

SUMMARY OF THE INVENTION

In one aspect, the disclosure relates to a breath actuated droplet delivery device for delivering a fluid as an ejected stream of droplets to the pulmonary system of a subject. In certain embodiments, the droplet delivery device is configured in an in-line orientation in that the housing, its internal components, and various device components (e.g., the mouthpiece, air inlet flow element, etc.) are orientated in a substantially in-line or parallel configuration (e.g., along the airflow path) so as to form a small, hand-held device.

In certain embodiments, the droplet delivery device may include: a housing; a mouthpiece positioned at the airflow exit side of the housing; a reservoir disposed within or in fluid communication with the housing for receiving a volume of fluid; an ejector mechanism in fluid communication with the reservoir, the ejector mechanism comprising a piezoelectric actuator and an aperture plate, the aperture plate having a plurality of openings formed through its thickness and the piezoelectric actuator operable to oscillate the aperture plate at a frequency to thereby generate an ejected stream of droplets, at least one differential pressure sensor positioned within the housing; the at least one differential pressure sensor configured to activate the ejector mechanism upon sensing a pre-determined pressure change within the mouthpiece to thereby generate an ejected stream of droplets; the ejector mechanism configured to generate the ejected stream of droplets wherein at least about 50% of the droplets have an average ejected droplet diameter of less than about 6 microns, such that at least about 50% of the mass of the ejected stream of droplets is delivered in a respirable range to the pulmonary system of a subject during use.

In some aspects, the droplet delivery device further includes an air inlet flow element positioned in the airflow at the airflow entrance of the device and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the mouthpiece.

In certain embodiments, the housing and ejector mechanism are oriented such that the exit side of the aperture plate is perpendicular to the direction of airflow and the stream of droplets is ejected in parallel to the direction of airflow. In other embodiments, the housing and ejector mechanism are oriented such that the exit side of the aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In certain aspects, the droplet delivery device further includes a surface tension plate between the aperture plate and the reservoir, wherein the surface tension plate is configured to increase contact between the volume of fluid and the aperture plate. In other aspects, the ejector mechanism and the surface tension plate are configured in parallel orientation. In yet other aspects, the surface tension plate is located within 2 mm of the aperture plate so as to create sufficient hydrostatic force to provide capillary flow between the surface tension plate and the aperture plate.

In yet other aspects, the aperture plate of the droplet delivery device comprises a domed shape. In other aspects, the aperture plate may be formed of a metal, e.g., stainless steel, nickel, cobalt, titanium, iridium, platinum, or palladium or alloys thereof. Alternatively, the plate can be formed of suitable material, including other metals or polymers, In other aspects. In certain embodiments, the aperture plate is comprised of, e.g., poly ether ether ketone (PEEK), polyimide, polyetherimide, polyvinylidine fluoride (PVDF), ultra-high molecular weight polyethylene (UHMWPE), nickel, nickel-cobalt, palladium, nickel-palladium, platinum, or other suitable metal alloys, and combinations thereof. In other aspects, one or more of the plurality of openings of the aperture plate have different cross-sectional shapes or diameters to thereby provide ejected droplets having different average ejected droplet diameters.

In yet other aspects, the reservoir of the droplet delivery device is removably coupled with the housing. In other aspects, the reservoir of the droplet delivery device is coupled to the ejector mechanism to form a combination reservoir/ejector mechanism module, and the combination reservoir/ejector mechanism module is removably coupled with the housing.

In other aspects, the droplet delivery device may further include a wireless communication module. In some aspects, the wireless communication module is a Bluetooth® wireless technology transmitter.

In yet other aspects, the droplet delivery device may further include one or more sensors selected from an inferred transmitter, a photodetector, an additional pressure sensor, and combinations thereof.

In one aspect, the disclosure relates to a method for generating and delivering a fluid as an ejected stream of droplets to the pulmonary system of a subject in a respirable range. The method may comprise: (a) generating an ejected stream of droplets via a breath actuated droplet delivery device of the disclosure, wherein at least about 50% of the ejected stream of droplets have an average ejected droplet diameter of less than about 6 µm; and (b) delivering the ejected stream of droplets to the pulmonary system of the subject such that at least about 50% of the mass of the ejected stream of droplets is delivered in a respirable range to the pulmonary system of a subject during use.

In another aspect, this disclosure relates to a method for delivering a therapeutic agent as an ejected stream of droplets in a respirable range to the pulmonary system of a subject for the treatment of a pulmonary disease, disorder or condition. The method may comprise: (a) generating an ejected stream of droplets via a breath actuated droplet delivery device of the disclosure, wherein at least about 50% of the ejected stream of droplets have an average ejected droplet diameter of less than about 6 µm; and (b) delivering the ejected stream of droplets to the pulmonary system of the subject such that at least about 50% of the mass of the ejected stream of droplets is delivered in a respirable range to the pulmonary system of a subject during use to thereby treat the pulmonary disease, disorder or condition.

In certain embodiments, the pulmonary disease, disorder or condition is selected from asthma, chronic obstructive pulmonary diseases (COPD) cystic fibrosis (CF), tuberculosis, chronic bronchitis, and pneumonia. In further aspects, the therapeutic agent is a COPD medication, an asthma medication, or an antibiotic. The therapeutic agent may be selected from albuterol sulfate, ipratropium bromide, tobramycin, fluticasone propionate, fluticasone furoate, tiotropium, glycopyrrolate, olodaterol, salmeterol, umeclidinium, and combinations thereof. In yet other aspects, the therapeutic agent may be delivered to the pulmonary system of the subject at a reduced dosage, as compared to standard propellant based inhaler dosages.

In yet another aspect, the disclosure relates to a method for the systemic delivery of a therapeutic agent as an ejected stream of droplets in a respirable range to the pulmonary system of a subject for the treatment of a disease, disorder or condition. The method may comprise: (a) generating an ejected stream of droplets via a piezoelectric actuated droplet delivery device, wherein at least about 50% of the ejected stream of droplets have an average ejected droplet diameter of less than about 6 µm; and (b) delivering the ejected stream of droplets to the pulmonary system of the subject such that at least about 50% of the mass of the ejected stream of droplets is delivered in a respirable range to the pulmonary system of a subject during use to thereby systemically delivery the therapeutic agent to the subject to treat the disease, disorder or condition.

In certain embodiments, the disease, disorder or condition is selected from diabetes mellitus, rheumatoid arthritis, plaque psoriasis, Crohn's disease, hormone replacement therapy, neutropenia, nausea, and influenza. In further aspects, the therapeutic agent is a therapeutic peptide, protein, antibody, or other bioengineered molecule. In yet further aspects, the therapeutic agent is selected from growth factors, insulin, vaccines, antibodies, Fc-fusion protein, hormones, enzymes, gene therapies and RNAi cell therapies, antibody-drug conjugates, cytokines, anti-infective agents, polynucleotides, oligonucleotides, or any combination thereof. In other aspects, the therapeutic agent is delivered to the pulmonary system of the subject at a reduced dosage, as compared to oral or intravenous dosages.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the detailed descriptions are to be regarded as illustrative in nature and not restrictive.

BRIEF DESCRIPTION OF THE DRAWINGS

FIGS. 1A-1B illustrate perspective views of an exemplary in-line droplet delivery device, in accordance with embodiments of the disclosure.

FIG. 3A-1 is a partial perspective view of a base unit of an in-line droplet delivery device of FIG. 1A-1B, in accordance with embodiments of the disclosure.

FIG. 3A-2 is an exploded view of an in-line droplet delivery device of FIG. 1A-1B, in accordance with embodiments of the disclosure.

FIG. 3B-1 is a bottom perspective view of a drug delivery ampoule of an in-line droplet delivery device of FIG. 1A-1B, in accordance with embodiments of the disclosure.

FIG. 3B-2 is an exploded view of an in-line droplet delivery device of FIG. 1A-1B, in accordance with embodiments of the disclosure.

FIGS. 3C-1, 3C-2, and 3C-3 are cross section perspective views of an in-line droplet delivery device of FIG. 1A-1B, in accordance with embodiments of the disclosure.

FIGS. 9A-9C show an alternative drug delivery ampoule, with FIG. 9A showing a perspective view, FIG. 9B showing a top exploded view, and FIG. 9C showing a bottom exploded view.

FIG. 10A is a partial cross section perspective view of an in-line droplet delivery device of FIG. 1A-1B comprising a drug delivery ampoule, mouthpiece including an air inlet flow element, and mouthpiece cover, in accordance with an embodiment of the disclosure.

FIG. 10B is a front view of an in-line droplet delivery device of FIG. 1A-1B comprising a drug delivery ampoule and mouthpiece including an air inlet flow element, in accordance with an embodiment of the disclosure.

FIG. 14A shows an alternative drug delivery ampoule with a mouthpiece interfaced at the airflow exit side of the device, in accordance with an embodiment of the disclosure. FIG. 14B shows a front cross-section and FIG. 14C shows a side cross-section, with FIG. 14D showing the same views with exemplary dimensions.

FIG. 16A shows an exemplary drug delivery ampoule with a mouthpiece interfaced at the airflow exit side of the device, in accordance with an embodiment of the disclosure. The mouthpiece includes two airflow entrances on the exterior sides of the mouthpiece, and two interior baffles with additional airflow entrances to provide resistance and modeling of airflow. FIG. 16B shows a front cross-section and FIG. 16C shows a side cross-section, with FIG. 16D showing the same views with exemplary dimensions.

FIG. 17A shows an exemplary drug delivery ampoule with a mouthpiece interfaced at the airflow exit side of the device, in accordance with an embodiment of the disclosure. The mouthpiece includes two airflow entrances on the exterior sides of the mouthpiece, and a substantially concentric baffle (two arcs that form a circle with the top and bottom of the mouthpiece) with two additional airflow entrances to provide resistance and modeling of airflow. FIG. 17B shows a front cross-section and FIG. 17C shows a side cross-section, with FIG. 17D showing the same views with exemplary dimensions.

FIG. 18A shows an exemplary drug delivery ampoule with a mouthpiece interfaced at the airflow exit side of the device, in accordance with an embodiment of the disclosure. The mouthpiece includes two airflow entrances on the exterior sides of the mouthpiece, and a substantially concentric baffle (two arcs that form a circle with the top and bottom of the mouthpiece) with four airflow entrances to provide resistance and modeling of airflow. FIG. 18B shows a front cross-section and FIG. 18C shows a side cross-section, with FIG. 18D showing the same views with exemplary dimensions.

FIG. 19A shows an exemplary drug delivery ampoule with a mouthpiece interfaced at the airflow exit side of the device, in accordance with an embodiment of the disclosure. The mouthpiece includes two airflow entrances on the exterior sides of the mouthpiece, and a substantially concentric baffle with two additional airflow entrances to provide resistance and modeling of airflow. In addition, the interior area of the mouthpiece between the concentric baffle and the wall of the mouthpiece includes an array element positioned above the airflow entrances to provide additional resistance and modeling to airflow. The array element is positioned in a parallel arrangement with the direction of airflow. FIG. 19B shows a front cross-section and FIG. 1919C shows a side cross-section, with FIG. 19D showing the same views with exemplary dimensions.

FIGS. 21A-21D illustrate exemplary aperture plate seal mechanisms, in accordance with embodiments of the disclosure. FIG. 21A showing the ampoule in end view, FIG. 21B and FIG. 21C showing the ampoule in side view. FIG. 21D illustrates an alternative embodiment wherein the mouthpiece cover includes an aperture plate plug.

FIG. 22 shows a summary of Mouth, Throat, Coarse, Respirable and Fine Particle Dose for testing of droplet delivery devices of the disclosure and comparator devices (Respimat) (Mean±SD), *Adjusted for 11,880 μg/ml Albuterol Sulfate Solution; Anderson Cascade Impactor Testing, in accordance with embodiments of the disclosure.

DETAILED DESCRIPTION

Effective delivery of medication to the deep pulmonary regions of the lungs through the alveoli, has always posed a problem, especially to children and elderly, as well as to those with the diseased state, owing to their limited lung capacity and constriction of the breathing passageways. The impact of constricted lung passageways limits deep inspiration and synchronization of the administered dose with the inspiration/expiration cycle. For optimum deposition in alveolar airways, droplets with aerodynamic diameters in the ranges of 1 to 5 μm are optimal, with droplets below about 4 μm shown to more effectively reach the alveolar region of the lungs, while larger droplets above about 6 μm are deposited on the tongue or strike the throat and coat the bronchial passages. Smaller droplets, for example less than about 1 μm that penetrate more deeply into the lungs have a tendency to be exhaled.

Certain aspects of the disclosure relate to an electronic, fully digital platform for delivery of inhaled therapeutics, described herein as an in-line droplet delivery device or soft mist inhaler (SMI) device. The device provides substantial improvements over current inhaled delivery systems by improving dosing precision, dosing reliability, and delivery to the patient. In certain embodiments, the device of the disclosure includes fully integrated monitoring capabilities designed to enhance compliance and ultimately reduce disease associated morbidity.

In certain aspects of the disclosure, target diseases for which the devices of the disclosure are particularly suited for use in the treatment and/or prevention of include asthma and Chronic Obstructive Pulmonary Disease (COPD).

Asthma is a chronic inflammatory disease of the airways characterized by temporary airway narrowing, with patients experiencing recurrent episodes of coughing, wheezing, breathlessness and chest tightness. These episodes are usually associated with widespread but variable airflow obstruction that is often reversible either spontaneously or with treatment. Asthma attacks can be triggered by a myriad of factors, including allergens, irritants in the air, medications, extreme weather conditions, exercise or stress.

The goals of asthma treatment are to reduce symptoms and prevent future episodes or attacks. Prevention is based on eliminating or reducing triggering exposures where possible. The mainstay for pharmacotherapy is through inhaled medications. Medications are divided into two categories: (a) those that provide quick-relief to treat acute symptoms and exacerbations (i.e. short-acting bronchodilators), and (b) those that provide long-term control (i.e. inhaled steroids). Long-acting bronchodilators are important medications but should not be used unless symptoms continue despite use of inhaled steroids. Other medications for severe persistent asthma are available for adjuvant treatment (i.e. omalizumab by injection). Short acting beta$_2$-agonists (SABA), such as albuterol, are the drugs of choice to relieve acute symptoms and to prevent, e.g., exercise-induced bronchoconstriction (EIB).

Chronic Obstructive Pulmonary Disease (COPD) is characterized by persistent respiratory symptoms and airflow limitations that are often due to airway and/or alveolar abnormalities. COPD includes chronic bronchitis and emphysema, which are often present in the same individual with COPD. The etiology of COPD has been linked to smoking, environmental exposure to air pollutants and genetics. Symptoms typically include dyspnea, chronic cough, which can be either productive (sputum) and non-productive, wheezing, and fatigue.

As with asthma, the most common and important medications for treatment are delivered by inhalation. Symptomatic patients with COPD should be receiving maintenance bronchodilators. In general, long-acting bronchodilators are used (i.e. once daily or twice daily); however, short-acting bronchodilators (e.g., albuterol and ipratropium alone or in combination) continue to be used. The short-acting bronchodilators may be used as-needed or on a regular basis. Long-acting bronchodilators are divided into two classes: long-acting beta agonists (LABA) and long-acting muscarinic antagonist (LAMA), which can be used alone or in combination. Patients on long acting bronchodilators who experience exacerbations of their COPD can add inhaled corticosteroids to their maintenance treatment. Furthermore, exacerbations in patients with COPD with chronic bronchitis and severe airflow restrictions, despite the use of combination bronchodilator with inhaled corticosteroids, can also use oral PDE4 inhibitors.

The following table summarizes the most commonly used inhaled medications for asthma and COPD.

| Category | Medication |
|---|---|
| Short-acting bronchodilators | Anticholinergic - ipratropium<br>Beta-agonist - albuterol, fenoterol, terbutaline |
| Long-acting bronchodilators - twice daily | Anticholinergic - glycopyrrolate, aclidinium<br>Beta-agonist - salmeterol, formoterol |
| Long-acting bronchodilators - once daily | Anticholinergic - tiotropium, umeclidinium<br>Beta-agonist - vilanterol, olodaterol |
| Inhaled steroids - twice daily | Fluticasone propionate, budesonide, mometasone, ciclesonide |
| Inhaled steroids - once daily | Fluticasone furoate |

The mainstay for therapy for both asthma and COPD is inhaled medications. The efficacy of the inhaled medicines can be significantly impacted by the devices used to deliver them. Commercially available devices used to deliver inhaled medications are: 1) nebulizers, 2) pressurized metered dose inhalers (MDI), and 3) dry powder inhalers (DPI). Each of these devices is decades old and has significant limitations.

In certain aspects of the disclosure, an in-line droplet delivery device, or soft mist inhaler (SMI) device (these terms are used interchangeably herein) is disclosed. The SMI is a novel inhaled drug delivery device that overcomes limitations of the currently available pulmonary drug delivery devices.

Figure 2:
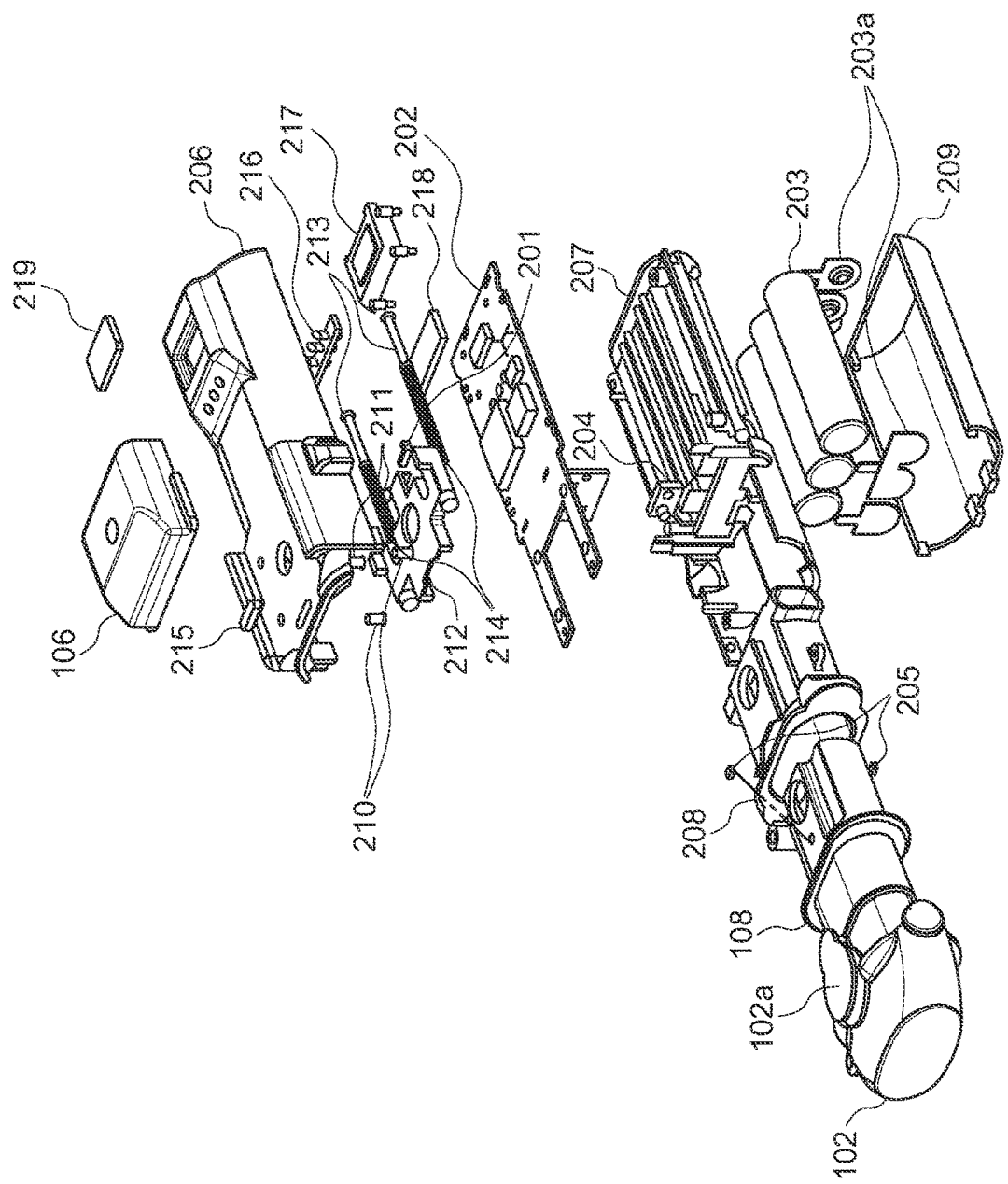
FIG. 2 is an exploded view of an in-line droplet delivery device of FIG. 1A-1B, in accordance with embodiments of the disclosure.

In certain aspects, the present disclosure relates to an in-line droplet delivery device for delivery a fluid as an ejected stream of droplets to the pulmonary system of a subject and related methods of delivering safe, suitable, and repeatable dosages to the pulmonary system of a subject. The present disclosure also includes an in-line droplet delivery device and system capable of delivering a defined volume of fluid in the form of an ejected stream of droplets such that an adequate and repeatable high percentage of the droplets are delivered into the desired location within the airways, e.g., the alveolar airways of the subject during use.

The present disclosure provides an in-line droplet delivery device for delivery of a fluid as an ejected stream of droplets to the pulmonary system of a subject, the device comprising a housing, a mouthpiece, a reservoir for receiving a volume of fluid, and an ejector mechanism including a piezoelectric actuator and an aperture plate, wherein the ejector mechanism is configured to eject a stream of droplets having an average ejected droplet diameter of less than about 6 microns, preferably less than about 5 microns.

As shown in further detail herein, the droplet delivery device is configured in an in-line orientation in that the housing, its internal components, and various device components (e.g., the mouthpiece, air inlet flow element, etc.) are orientated in a substantially in-line or parallel configuration (e.g., along the airflow path) so as to form a small, hand-held device. In certain embodiments, the housing and ejector mechanism are oriented such that the exit side of aperture plate is perpendicular to the direction of airflow and the stream of droplets is ejected in parallel to the direction of airflow. In other embodiments, the housing and ejector mechanism are oriented such that the exit side of aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In specific embodiments, the ejector mechanism is electronically breath activated by at least one differential pressure sensor located within the housing of the in-line droplet delivery device upon sensing a pre-determined pressure change within the mouthpiece. In certain embodiments, such a pre-determined pressure change may be sensed during an inspiration cycle by a user of the device, as will be explained in further detail herein.

In some aspects, the droplet delivery device further includes an air inlet flow element positioned in the airflow at the airflow entrance of the housing and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the mouthpiece As will be described in further detail herein, the air inlet flow element may be positioned behind the exit side of the aperture plate along the direction of airflow, or in-line or in front of the exit side of the aperture plate along the direction of airflow. In certain embodiments, the air inlet flow element comprises one or more openings formed there through and configured to increase or decrease internal pressure resistance within the droplet delivery device during use. For instance, the air inlet flow element comprises an array of one or openings. In the embodiments, the air inlet flow element comprises one or more baffles, e.g., wherein the one or more baffles comprise one or more airflow openings.

In accordance with certain aspects of the disclosure, effective deposition into the lungs generally requires droplets less than about 5-6 µm in diameter. Without intending to be limited by theory, to deliver fluid to the lungs a droplet delivery device must impart a momentum that is sufficiently high to permit ejection out of the device, but sufficiently low to prevent deposition on the tongue or in the back of the throat. Droplets below approximately 5-6 µm in diameter are transported almost completely by motion of the airstream and entrained air that carry them and not by their own momentum.

In certain aspects, the present disclosure includes and provides an ejector mechanism configured to eject a stream of droplets within the respirable range of less than about 5-6 µm, preferably less than about 5 µm. The ejector mechanism is comprised of an aperture plate that is directly or indirectly coupled to a piezoelectric actuator. In certain implementations, the aperture plate may be coupled to an actuator plate that is coupled to the piezoelectric actuator. The aperture plate generally includes a plurality of openings formed through its thickness and the piezoelectric actuator directly or indirectly (e.g. via an actuator plate) oscillates the aperture plate, having fluid in contact with one surface of the aperture plate, at a frequency and voltage to generate a directed aerosol stream of droplets through the openings of the aperture plate into the lungs, as the patient inhales. In other implementations where the aperture plate is coupled to the actuator plate, the actuator plate is oscillated by the piezoelectric oscillator at a frequency and voltage to generate a directed aerosol stream or plume of aerosol droplets.

In certain aspects, the present disclosure relates to an in-line droplet delivery device for delivering a fluid as an ejected stream of droplets to the pulmonary system of a subject. The ejected stream of droplets includes, without limitation, droplets formed from solutions, suspensions or emulsions which have viscosities in a range capable of droplet formation using the ejector mechanism. In certain aspects, the therapeutic agents may be delivered at a high dose concentration and efficacy, as compared to alternative dosing routes and standard inhalation technologies.

In certain embodiments, the in-line droplet delivery devices of the disclosure may be used to treat various diseases, disorders and conditions by delivering therapeutic agents to the pulmonary system of a subject. In this regard, the in-line droplet delivery devices may be used to deliver therapeutic agents both locally to the pulmonary system, and systemically to the body.

More specifically, the in-line droplet delivery device may be used to deliver therapeutic agents as an ejected stream of droplets to the pulmonary system of a subject for the treatment or prevention of pulmonary diseases or disorders such as asthma, chronic obstructive pulmonary diseases (COPD) cystic fibrosis (CF), tuberculosis, chronic bronchitis, or pneumonia. In certain embodiments, the in-line droplet delivery device may be used to deliver therapeutic agents such as COPD medications, asthma medications, or antibiotics. By way of non-limiting example, such therapeutic agents include albuterol sulfate, ipratropium bromide, tobramycin, fluticasone propionate, fluticasone furoate, tiotropium, glycopyrrolate, olodaterol, salmeterol, umeclidinium, and combinations thereof.

In other embodiments, the in-line droplet delivery device may be used for the systemic delivery of therapeutic agents including small molecules, therapeutic peptides, proteins, antibodies, and other bioengineered molecules via the pulmonary system. By way of non-limiting example, the in-line droplet delivery device may be used to systemically deliver therapeutic agents for the treatment or prevention of indications inducing, e.g., diabetes mellitus, rheumatoid arthritis, plaque psoriasis, Crohn's disease, hormone replacement, neutropenia, nausea, influenza, etc.

By way of non-limiting example, therapeutic peptides, proteins, antibodies, and other bioengineered molecules include: growth factors, insulin, vaccines (Prevnor—Pneumonia, Gardasil—HPV), antibodies (Keytruda (pembrolizumab), Opdivo (nivolumab) Avastin (bevacizumab), Humira (adalimumab), Remicade (infliximab), Herceptin (trastuzumab)), Fc Fusion Proteins (Enbrel (etanercept), Orencia (abatacept)), hormones (Elonva—long acting FSH, Growth Hormone), enzymes (Pulmozyme—rHu-DNAase–), other proteins (Clotting factors, Interleukins, Albumin), gene therapy and RNAi, cell therapy (Provenge—Prostate cancer vaccine), antibody drug conjugates—Adcetris (Brentuximab vedotin for HL), cytokines, anti-infective agents, polynucleotides, oligonucleotides (e.g., gene vectors), or any combination thereof; or solid droplets or suspensions such as Flonase (fluticasone propionate) or Advair (fluticasone propionate and salmeterol xinafoate).

In other embodiments, the in-line droplet delivery device of the disclosure may be used to deliver a solution of nicotine including the water-nicotine azeotrope for the delivery of highly controlled dosages for smoking cessation or a condition requiring medical or veterinary treatment. In addition, the fluid may contain THC, CBD, or other chemicals contained in marijuana for the treatment of seizures and other conditions.

In certain embodiments, the in-line drug delivery device of the disclosure may be used to deliver scheduled and controlled substances such as narcotics for the highly controlled dispense of pain medications where dosing is monitored or otherwise controlled. In certain embodiments, by way of non-limiting example, dosing may only enabled by doctor or pharmacy communication to the device, only in a specific location such as the patient's residence as verified by GPS location on the patient's smart phone, and/or it may be controlled by monitoring compliance with dosing schedules, amounts, abuse compliances, etc. In certain aspects, this mechanism of highly controlled dispensing of controlled medications can prevent the abuse or overdose of controlled substances.

Certain benefits of the pulmonary route for delivery of drugs and other medications include a non-invasive, needle-free delivery system that is suitable for delivery of a wide range of substances from small molecules to very large proteins, reduced level of metabolizing enzymes compared to the GI tract and absorbed molecules do not undergo a first pass effect. (A. Tronde, et al., J Pharm Sci, 92 (2003) 1216-1233; A. L. Adjei, et al., Inhalation Delivery of Therapeutic Peptides and Proteins, M. Dekker, New York, 1997). Further, medications that are administered orally or intravenously are diluted through the body, while medications given directly into the lungs may provide concentrations at the target site (the lungs) that are about 100 times higher than the same intravenous dose. This is especially important for treatment of drug resistant bacteria, drug resistant tuberculosis, for example and to address drug resistant bacterial infections that are an increasing problem in the ICU.

Another benefit for giving medication directly into the lungs is that high, toxic levels of medications in the blood stream their associated side effects can be minimized. For example intravenous administration of tobramycin leads to very high serum levels that are toxic to the kidneys and therefore limits its use, while administration by inhalation significantly improves pulmonary function without severe side effects to kidney functions. (Ramsey et al., Intermittent administration of inhaled tobramycin in patients with cystic fibrosis. N Engl J Med 1999; 340:23-30; MacLusky et al., Long-term effects of inhaled tobramycin in patients with cystic fibrosis colonized with *Pseudomonas aeruginosa*. Pediatr Pulmonol 1989; 7:42-48; Geller et al., Pharmacokinetics and bioavailablility of aerosolized tobramycin in cystic fibrosis. Chest 2002; 122:219-226.)

As discussed above, effective delivery of droplets deep into the lung airways require droplets that are less than about 5-6 microns in diameter, specifically droplets with mass mean aerodynamic diameters (MMAD) that are less than about 5 microns. The mass mean aerodynamic diameter is defined as the diameter at which 50% of the droplets by mass are larger and 50% are smaller. In certain aspects of the disclosure, in order to deposit in the alveolar airways, droplets in this size range must have momentum that is sufficiently high to permit ejection out of the device, but sufficiently low to overcome deposition onto the tongue (soft palate) or pharynx.

In other aspects of the disclosure, methods for generating an ejected stream of droplets for delivery to the pulmonary system of user using the droplet delivery devices of the disclosure are provided. In certain embodiments, the ejected stream of droplets is generated in a controllable and defined droplet size range. By way of example, the droplet size range includes at least about 50%, at least about 60%, at least about 70%, at least about 85%, at least about 90%, between about 50% and about 90%, between about 60% and about 90%, between about 70% and about 90%, between about 70% and about 95%, etc., of the ejected droplets are in a respirable range of below about 6 μm, preferably below about 5 μm.

In other embodiments, the ejected stream of droplets may have one or more diameters, such that droplets having multiple diameters are generated so as to target multiple regions in the airways (mouth, tongue, throat, upper airways, lower airways, deep lung, etc.) By way of example, droplet diameters may range from about 1 μm to about 200 μm, about 2 μm to about 100 μm, about 2 μm to about 60 μm, about 2 μm to about 40 μm, about 2 μm to about 20 μm, about 1 μm to about 5 μm, about 1 μm to about 4.7 μm, about 1 μm to about 4 μm, about 10 μm to about 40 μm, about 10 μm to about 20 μm, about 5 μm to about 10 μm, and combinations thereof. In particular embodiments, at least a fraction of the droplets have diameters in the respirable range, while other droplets may have diameters in other sizes so as to target non-respirable locations (e.g., larger than about 5 μm). Illustrative ejected droplet streams in this regard might have 50%-70% of droplets in the respirable range (less than about 5 μm), and 30%-50% outside of the respirable range (about 5 μm-about 10 μm, about 5 μm-about 20 μm, etc.)

In another embodiment, methods for delivering safe, suitable, and repeatable dosages of a medicament to the pulmonary system using the droplet delivery devices of the disclosure are provided. The methods deliver an ejected stream of droplets to the desired location within the pulmonary system of the subject, including the deep lungs and alveolar airways.

In certain aspects of the disclosure, an in-line droplet delivery device for delivery an ejected stream of droplets to the pulmonary system of a subject is provided. The in-line droplet delivery device generally includes a housing, a mouthpiece positioned at the airflow exit side of the housing, a reservoir disposed in or in fluid communication with the housing for receiving a volume of fluid, an ejector mechanism in fluid communication with the reservoir, and at least one differential pressure sensor positioned within the housing. The housing, its internal components, and various device components (e.g., the mouthpiece, air inlet flow element, etc.) are orientated in a substantially in-line or parallel configuration (e.g., along the airflow path) so as to form a small, hand-held device. The differential pressure sensor is configured to electronically breath activate the ejector mechanism upon sensing a pre-determined pressure change within the mouthpiece, and the ejector mechanism is configured to generate an ejected stream of droplets.

In certain embodiments, the mouthpiece may be interfaced with (and optionally removable and/or replaceable), integrated into, or part of the housing. In other embodiments, the mouthpiece may be interfaced with (and optionally removable and/or replaceable), integrated into, or part of the drug delivery ampoule.

The ejector mechanism may include a piezoelectric actuator which is directly or indirectly coupled to an aperture plate having a plurality of openings formed through its thickness. The piezoelectric actuator is operable to directly or indirectly oscillate the aperture plate at a frequency to thereby generate an ejected stream of droplets.

In certain embodiments, the housing and ejector mechanism are oriented such that the exit side of aperture plate is perpendicular to the direction of airflow and the stream of droplets is ejected in parallel to the direction of airflow. In other embodiments, the housing and ejector mechanism are oriented such that the exit side of aperture plate is parallel to the direction of airflow and the stream of droplets is ejected substantially perpendicularly to the direction of airflow such that the ejected stream of droplets is directed through the housing at an approximate 90 degree change of trajectory prior to expulsion from the housing.

In certain embodiments, the in-line droplet delivery device is comprised of a separate drug delivery ampoule with an ejector mechanism (e.g., combination reservoir/ejector mechanism module) embedded within a surface of a drug reservoir, and a handheld base unit (e.g., housing) including a differential pressure sensor, a microprocessor and three AAA batteries. In certain embodiments, the handheld base unit also includes a mouthpiece, optionally removable, an optional mouthpiece cover, and an optional ejector plate seal. The microprocessor controls dose delivery, dose counting and software designed monitoring parameters that can be transmitted through blue-tooth technology. The ejector mechanism optimizes droplet delivery to the lungs by creating an ejected droplet stream in a predefined range with a high degree of accuracy and repeatability. Initial droplet studies show at least 65% to 70% of droplets ejected from the device are in the respirable range (e.g., 1-5 μm).

In certain embodiments, the in-line droplet delivery device may include a combination reservoir/ejector mechanism module (e.g., drug delivery ampoule) that may be replaceable or disposable either on a periodic basis, e.g., a daily, weekly, monthly, as-needed, etc. basis, as may be suitable for a prescription or over-the-counter medication. The reservoir may be prefilled and stored in a pharmacy for dispensing to patients or filled at the pharmacy or elsewhere by using a suitable injection means such as a hollow injection syringe driven manually or driven by a micropump. The syringe may fill the reservoir by pumping fluid into or out of a rigid container or other collapsible or non-collapsible reservoir. In certain aspects, such disposable/replaceable, combination reservoir/ejector mechanism module may minimize and prevent buildup of surface deposits or surface microbial contamination on the aperture plate, owing to its short in-use time.

In certain aspects of the disclosure, the ejector mechanism, reservoir, and housing/mouthpiece function to generate a plume with droplet diameters less than about 5 um. As discussed above, in certain embodiments, the reservoir and ejector mechanism modules are powered by electronics in the device housing and a reservoir which may carry sufficient drug for a single dose, just a few doses, or several hundred doses of medicament.

The present disclosure also provides an in-line droplet delivery device that is altitude insensitive. In certain implementations, the in-line droplet delivery device is configured so as to be insensitive to pressure differentials that may occur when the user travels from sea level to sub-sea levels and at high altitudes, e.g., while traveling in an airplane where pressure differentials may be as great as 4 psi. As will be discussed in further detail herein, in certain implementations of the disclosure, the in-line droplet delivery device may include a superhydrophobic filter, optionally in combination with a spiral vapor barrier, which provides for free exchange of air into and out of the reservoir, while blocking moisture or fluids from passing into the reservoir, thereby reducing or preventing fluid leakage or deposition on aperture plate surfaces.

In certain aspects, the devices of the disclosure eliminate the need for patient/device coordination by using a differential pressure sensor to initiate the piezoelectric ejector in response to the onset of inhalation. The device does not require manual triggering of medication delivery. Unlike propellant driven MDIs, the droplets from the devices of the disclosure are generated having little to no intrinsic velocity from the aerosol formation process and are inspired into the lungs solely by the user's incoming breath passing through the mouthpiece. The droplets will ride on entrained air providing improved deposition in the lung.

In certain embodiments, as described in further detail herein, when the drug ampoule is mated to the handheld base unit, electrical contact is made between the base containing the batteries and the ejector mechanism embedded in the drug reservoir. In certain embodiments, visual indications, e.g., a horizontal series of three user visible LED lights, and audio indications via a small speaker within the handheld base unit may provide user notifications. By way of example, the device may be, e.g., 2.0-3.5 cm high, 5-7 cm wide, 10.5-12 cm long and may weight approximately 95 grams with an empty drug ampoule and with batteries inserted.

As described herein, in certain embodiments, the in-line droplet delivery device may be turned on and activated for use by inserting the drug ampoule into the base unit, opening the mouthpiece cover, and/or switching an on/off switch/slide bar. In certain embodiments, visual and/or audio indicators may be used to indicate the status of the device in this regard, e.g., on, off, stand-by, preparing, etc. By way of example, one or more LED lights may turn green and/or flash green to indicate the device is ready for use. In other embodiments, visual and/or audio indicators may be used to indicate the status of the drug ampoule, including the number of doses taken, the number of doses remaining, instructions for use, etc. For example, and LED visual screen may indicate a dose counter numerical display with the number of remaining doses in the reservoir.

As described in further detail herein, during use as a user inhales through the mouthpiece of the housing of an in-line droplet delivery device of the disclosure, a differential pressure sensor within the housing detects inspiratory flow, e.g., by measuring the pressure drop across a Venturi plate at the back of the mouthpiece. When a threshold pressure decline (e.g., 8 slm) is attained, the microprocessor activates the ejector mechanism, which in turn generates an ejected stream of droplets into the airflow of the device that the user inhales through the mouthpiece. In certain embodiments, audio and/or visual indicates may be used to indicate that dosing has been initiated, e.g., one or more LEDs may illuminate green. The microprocessor then deactivates the ejector at a designated time after initiation so as to achieve a desired administration dosage, e.g., 1-1.45 seconds. In certain embodiments, as described in further detail herein, the device may provide visual and/or audio indicators to facilitate proper dosing, e.g., the device may emit a positive chime sound after the initiation of dosing, indicating to the user to begin holding their breath for a designated period of time, e.g., 10 seconds. During the breath hold period, e.g., the three green LEDs may blink. Additionally, there may be voice commands instructing the patient on proper times to exhale, inhale and hold their breath, with an audio indicator of a breath hold countdown.

Following dosing, the in-line droplet delivery device may turned off and deactivated in any suitable manner, e.g., by closing the mouthpiece cover, switching an on/off switch/slide bar, timing out from non-use, removing the drug ampoule, etc. If desired, audio and/or visual indicators may prompt a user to deactivate the device, e.g., by flashing one or more red LED lights, providing voice commands to close the mouthpiece cover, etc.

In certain embodiments, the in-line droplet delivery device may include an ejector mechanism closure system that seals the aperture plate when not in use to protect the integrity of the aperture plate and to minimize and prevent contamination and evaporation of the fluid within the reservoir. For example, in some embodiments, the device may include a mouthpiece cover that comprises a rubber plug that is sized and shaped to seal the exit side surface of the aperture plate when the cover is closed. In other embodiments, the mouthpiece cover may trigger a slide to seal the exit side surface of the aperture plate when the cover is closed. Other embodiments and configurations are also envisioned, e.g., manual slides, covers, and plugs, etc. In certain aspects, the microprocessor may be configured to detect when the ejector mechanism closure, aperture plate seal, etc. is in place, and may thereafter deactivate the device.

Several features of the device allow precise dosing of specific droplet sizes. Droplet size is set by the diameter of the holes in the mesh which are formed with high accuracy. By way of example, the holes in the aperture plate may range in size from 1 µm to 6 µm, from 2 µm to 5 µm, from 3 µm to 5 µm, from 3 µm to 4 µm, etc. Ejection rate, in droplets per second, is generally fixed by the frequency of the aperture plate vibration, e.g., 108-kHz, which is actuated by the microprocessor. In certain embodiments, there is less than a 50-millisecond lag between the detection of the start of inhalation and full droplet generation.

Other aspects of the device of the disclosure that allow for precise dosing of specific droplet sizes include the production of droplets within the respirable range early in the inhalation cycle, thereby minimizing the amount of drug product being deposited in the mouth or upper airways at the end of an inhalation. In addition, the design of the drug ampoule allows the aperture plate surface to be wetted and ready for ejection without user intervention, thus obviating the need for shaking and priming. Further, the design of the drug ampoule vent configuration together with the ejector mechanism closure system limits fluid evaporation from the reservoir to less than 150 µL to 350 µL per month.

The device may be constructed with materials currently used in FDA cleared devices. Standard manufacturing methods may be employed to minimize extractables.

Any suitable material may be used to form the housing of the droplet delivery device. In particular embodiment, the material should be selected such that it does not interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc.

The drug ampoule may be constructed of any suitable materials for the intended pharmaceutical use. In particular, the drug contacting portions may be made from material compatible with the desired active agent(s), e.g., albuterol sulfate and ipratropium bromide. By way of example, in certain embodiments, the drug only contacts the inner side of the drug reservoir and the inner face of the aperture plate and piezoelectric element. Wires connecting the piezoelectric ejector mechanism to the batteries contained in the base unit may be embedded in the drug ampoule shell to avoid contact with the drug. The piezoelectric ejector may be attached to the drug reservoir by a flexible bushing. To the extent the bushing may contact the drug fluid, it may be, e.g., any suitable material known in the art for such purposes such as those used in piezoelectric nebulizers.

In certain embodiments, the device mouthpiece may be removable, replaceable and may be cleaned. Similarly, the device housing and drug ampoule can be cleaned by wiping with a moist cloth. In certain embodiments, the mouthpiece may be interfaced with (and optionally removable and/or replaceable), integrated into, or part of the housing. In other embodiments, the mouthpiece may be interfaced with (and optionally removable and/or replaceable), integrated into, or part of the drug delivery ampoule.

Again, any suitable material may be used to form the mouthpiece of the droplet delivery device. In particular embodiment, the material should be selected such that it does not negatively interact with the components of the device or the fluid to be ejected (e.g., drug or medicament components). For example, polymeric materials suitable for use in pharmaceutical applications may be used including, e.g., gamma radiation compatible polymer materials such as polystyrene, polysulfone, polyurethane, phenolics, polycarbonate, polyimides, aromatic polyesters (PET, PETG), etc. In certain embodiments, the mouthpiece may be removable, replaceable and sterilizable. This feature improves sanitation for drug delivery by providing a mechanism to minimize buildup of aerosolized medication within the mouthpiece and by providing for ease of replacement, disinfection and washing. In one embodiment, the mouthpiece tube may be formed from sterilizable and transparent polymer compositions such as polycarbonate, polyethylene or polypropylene, as discussed herein.

In certain aspects of the disclosure, an electrostatic coating may be applied to the one or more portions of the housing, e.g., inner surfaces of the housing along the airflow pathway such as the mouthpiece, to aid in reducing deposition of ejected droplets during use due to electrostatic charge build-up. Alternatively, one or more portions of the housing may be formed from a charge-dissipative polymer. For instance, conductive fillers are commercially available and may be compounded into the more common polymers used in medical applications, for example, PEEK, polycarbonate, polyolefins (polypropylene or polyethylene), or styrenes such as polystyrene or acrylic-butadiene-styrene (ABS) copolymers. Alternatively, in certain embodiments, one or more portions of the housing, e.g., inner surfaces of the housing along the airflow pathway such as the mouthpiece, may be coated with anti-microbial coatings, or may be coated with hydrophobic coatings to aid in reducing deposition of ejected droplets during use. Any suitable coatings known for such purposes may be used, e.g., polytetrafluoroethylene (Teflon).

Any suitable differential pressure sensor with adequate sensitivity to measure pressure changes obtained during standard inhalation cycles may be used, e.g., ±5 SLM, 10 SLM, 20 SLM, etc. For instance, pressure sensors from Sensirion, Inc., SDP31 or SDP32 (U.S. Pat. No. 7,490,511 B2) are particularly well suited for these applications.

In certain aspects, the microprocessor in the device may be programmed to ensure exact timing and actuation of the ejector mechanism in accordance with desired parameters, e.g., based duration of piezoelectric activation to achieve desired dosages, etc. In certain embodiments, the device includes or interfaces with a memory (on the device, smartphone, App, computer, etc.) to record the date-time of each ejection event, as well as the user's inhalation flow rate during the dose inhalation to facilitate user monitoring, as well as drug ampoule usage monitoring. For instance, the microprocessor and memory can monitor doses administered and doses remaining in a particular drug ampoule. In certain embodiments, the drug ampoule may comprise components that include identifiable information, and the base unit may comprise components that may "read" the identifiable information to sense when a drug ampoule has been inserted into the base unit, e.g., based on a unique electrical resistance of each individual ampoule, an RFID chip, or other readable microchip (e.g., cryptoauthentication microchip). Dose counting and lockouts may also be preprogramed into the microprocessor.

In certain embodiments of the present disclosure, the signal generated by the pressure sensors provides a trigger for activation and actuation of the ejector mechanism to thereby generate droplets and delivery droplets at or during a peak period of a patient's inhalation (inspiratory) cycle and assures optimum deposition of the plume of droplets and delivery of the medication into the pulmonary airways of the user.

In accordance with certain aspects of the disclosure, the in-line droplet delivery device provides a reliable monitoring system that can date and time stamp actual deliver of medication, e.g., to benefit patients with asthma through self-monitoring or through involvement of care givers and family members. The ability of a parent to know the use of asthma medications in a child is obvious. Physicians who can access such information will be better equipped to help their patients with asthma and COPD. It is even possible to consider monitoring of the impact of environmental conditions in a patient population with asthma to help determine public policy.

As described in further detail herein, the in-line droplet delivery device of the disclosure may detect inspiratory airflow and record/store inspiratory airflow in a memory (on the device, smartphone, App, computer, etc.). A preset threshold (e.g., 8-10 slm) triggers delivery of medication over a defined period of time, e.g., 1-1.5 seconds. Inspiratory flow is sampled frequently until flow stops. The number of times that delivery is triggered is incorporated and displayed in the dose counter LED on the device. Blue tooth capabilities permit the wireless transmission of the data.

Bluetooth® wireless technology communication in the device will communicate date, time and number of actuations per session to the user's smartphone. Software programing can provide charts, graphics, medication reminders and warnings to patients and whoever is granted permission to the data. The software application will be able to incorporate multiple medications that use the device of the disclosure (e.g. albuterol, inhaled steroid, etc.).

In certain embodiments, the monitoring capability should lead to early detection of worsening asthma or COPD and early intervention that will reduce exacerbations. The worsening would be detected through the increased requirement for rescue medication. While there are often identifiable triggers to disease worsening, worsening may occur due to lack of adherence to maintenance medication. Prevention of exacerbations or early interventions can potentially have profound positive impacts on quality of life and health resource utilization. Finally, monitoring data may provide support for improvement in disease state and the possibility for reducing maintenance medications.

The device of the disclosure can also provide directed instruction to users, including audio and visual indicators to facilitate proper use of the device and proper dosing. For instance, patients with COPD or asthma who need drug delivered to an inflamed and narrowed lower respiratory region are typically asked to inhale drug particles slowly and steadily followed by about ten seconds of holding their breath to allow sedimentation to occur. In a medical office these patients can be coached and encouraged to hold their breath after inhalation. However, outside of a medical care setting, improper use of an inhaler device often results.

The device of the present disclosure is configured to dispense droplets during the correct part of the inhalation cycle, and can including instruction and/or coaching features to assist patients with proper device use, e.g., by instructing the holding of breath for the correct amount of time after inhalation. The device of the disclosure allows this dual functionality because it may both monitor air flow during the inhalation, and has internal sensors/controls which may detect the end of inhalation (based upon measured flow rate) and can cue the patient to hold their breath for a fixed duration after the inhalation ceases.

In one exemplary embodiment, a patient may be coached to hold their breath with an LED that is turned on at the end of inhalation and turned off after a defined period of time (i.e., desired time period of breath hold), e.g., 10 seconds. Alternatively, the LED may blink after inhalation, and continue blinking until the breath holding period has ended. In this case, the processing in the device detects the end of inhalation, turns on the LED (or causes blinking of the LED, etc.), waits the defined period of time, and then turns off the LED. Similarly, the device can emit audio indications, e.g., one or more bursts of sound (e.g., a 50 millisecond pulse of 1000 Hz), verbal instructions to hold breath, verbal countdown, music, tune, melody, etc., at the end of inhalation to cue a patient to hold their breath for the during of the sound signals. If desired, the device may also vibrate during or upon conclusion of the breath holding period.

In certain embodiments, the device provides a combination of audio and visual methods (or sound, light and vibration) described above to communicate to the user when the breath holding period has begun and when it has ended. Or during the breath holding to show progress (e.g., a visual or audio countdown).

In other aspects, the device of the disclosure may provide coaching to inhale longer, more deeply, etc. The average peak inspiratory flow during inhalation (or dosing) can be utilized to provide coaching. For example, a patient may hear a breath deeper command until they reach 90% of their average peak inspiratory flow as measured during inspiration (dosing) as stored on the device, phone or in the cloud.

In addition, an image capture device, including cameras, scanners, or other sensors without limitation, e.g. charge coupled device (CCD), may be provided to detect and measure the ejected aerosol plume. These detectors, LED, delta P transducer, CCD device, all provide controlling signals to a microprocessor or controller in the device used for monitoring, sensing, measuring and controlling the ejection of a plume of droplets and reporting patient compliance, treatment times, dosage, and patient usage history, etc., via Bluetooth® wireless technology, for example.

Reference will now be made to the figures, with like components illustrates with like references numbers.

FIGS. 1A and 1B illustrate an exemplary in-line droplet delivery device of the disclosure, with FIG. 1A showing the in-line droplet delivery device 100 having a mouthpiece cover 102 in the closed position, and FIG. 1B having a mouthpiece cover 102 in the open position. As shown, the droplet delivery device is configured in an in-line orientation in that the housing, its internal components, and various device components (e.g., the mouthpiece, air inlet flow element, etc.) are orientated in a substantially in-line or parallel configuration (e.g., along the airflow path) so as to form a small, hand-held device.

In the embodiment shown in FIGS. 1A and 1B, the in-line droplet delivery device 100 includes a base unit 104 and a drug delivery ampoule 106. As illustrated in this embodiment, and discussed in further detail herein, the drug delivery ampoule 106 slides into the front of the base unit 104 via slides 112. In certain embodiments, mouthpiece cover 102 may include a push element 102a that facilitates insertion of drug delivery ampoule 106. Also illustrated are one or more airflow entrances or openings 110. By way of example, there may be airflow entrances on the opposite side of the device, multiple airflow entrances on the same side of the device, or a combination thereof (not shown). The in-line droplet delivery device 100 also includes mouthpiece 108 at the airflow exit side of the device.

With reference to FIG. 2, an exploded view of the exemplary in-line droplet delivery device of FIGS. 1A and 1B is shown, including internal components of the housing including a power/activation button 201; an electronics circuit board 202; a drug delivery ampoule 106 that comprises an ejector mechanism and reservoir (not shown); and a power source 203 (e.g., three AAA batteries, which may optionally be rechargeable) along with associated contacts 203a. In certain embodiments, the reservoir may be single-unit dose or multi-unit dose that may be replaceable, disposable or reusable. Also shown, one or more pressure sensors 204 and optional spray sensors 205. In certain embodiments, the device may also include various electrical contacts 210 and 211 to facilitate activation of the device upon insertion of drug delivery ampoule 106 into the base unit. Likewise, in certain embodiments, the device may include slides 212, posts 213, springs 214, and ampoule lock 215 to facilitate insertion of drug delivery ampoule 106 into the base unit.

The components may be packaged in a housing, and generally oriented in an in-line configuration. The housing may be disposable or reusable, single-dose or multi-dose. Although various configurations to form the housing are within the scope of the disclosure, as illustrated in FIG. 2, the housing may comprise a top cover 206, a bottom cover 207, and an inner housing 208. The housing may also include a power source housing or cover 209.

In certain embodiments, the device may include audio and/or visual indications, e.g., to provide instructions and communications to a user. In such embodiments, the device may include a speaker or audio chip (not shown), one or more LED lights 216, and LCD display 217 (interfaced with an LCD control board 218 and lens cover 219). The housing may be handheld and may be adapted for communication with other devices via a Bluetooth® wireless technology communication module or similar wireless communication module, e.g., for communication with a subject's smart phone, tablet or smart device (not shown).

In certain embodiments, an air inlet flow element (not shown, see, e.g., FIGS. 5A-5C and FIGS. 11A-18D) may be positioned in the airflow at the airflow entrance of the housing and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the mouthpiece. Aspects of the present embodiment further allows customizing the internal pressure resistance of the particle delivery device by allowing the placement of laminar flow elements having openings of different sizes and varying configurations to selectively increase or decrease internal pressure resistance, as will be explained in further detail herein.

By way of non-limiting example, an exemplary method of insertion of an ampoule through to use and powering off of the device may be performed as follows:

1. When a new ampoule is initially inserted and pushed onto the device slide guide the device door is open and the ampoule slides and clicks into ampoule position 1. At this setting, an aperture plate seal or cover on the ampoule is open and electrical contacts on the device and ampoule make contact. The system is powered ON and ready for breath actuation. When the device door is opened, an audible beep may be emitted and LED indicator(s) may turn green or flash to notify the user that the system is ON and ready for dosing by inhaling through the mouthpiece.
2. As a patient inhales, a pre-set pressure value is reached and detected by the pressure sensor located within the housing (e.g., delta P sensor) and a second audible indicator or LED indicator may now indicate that a dose is triggered. After the dose is triggered and delivered, another audible and/or LED indicator may trigger until a spray cycle time of, e.g, 1-5 seconds (or other designated dosing time) ends. Further, if desired, when a dose is delivered, the dose counter displayed on the LCD will indicate that a dose was delivered by a decrease in number of doses displayed on the LCD.
3. If no additional doses are required and a time of, e.g., 15 seconds elapse, an audible and/or LED indicator may trigger to alert the user that the device is about to power-off, after which time the device may enter into a low power, sleep mode.
4. If no additional doses are required, the device door is closed to push the ampoule to the non-use position, the aperture plate seal or cover is closed and the device is in placed sleep mode. Further, as the slide mechanism releases pressure from the ON/OFF switch, and the system is now OFF.

5. When a patient is ready to apply additional doses, the device door is opened and the ampoule slides towards the mouthpiece as it is pushed by a spring-loaded mechanism from the non-use position to the use position, to thereby open the aperture plate seal or cover.

Figures 2, 3B:
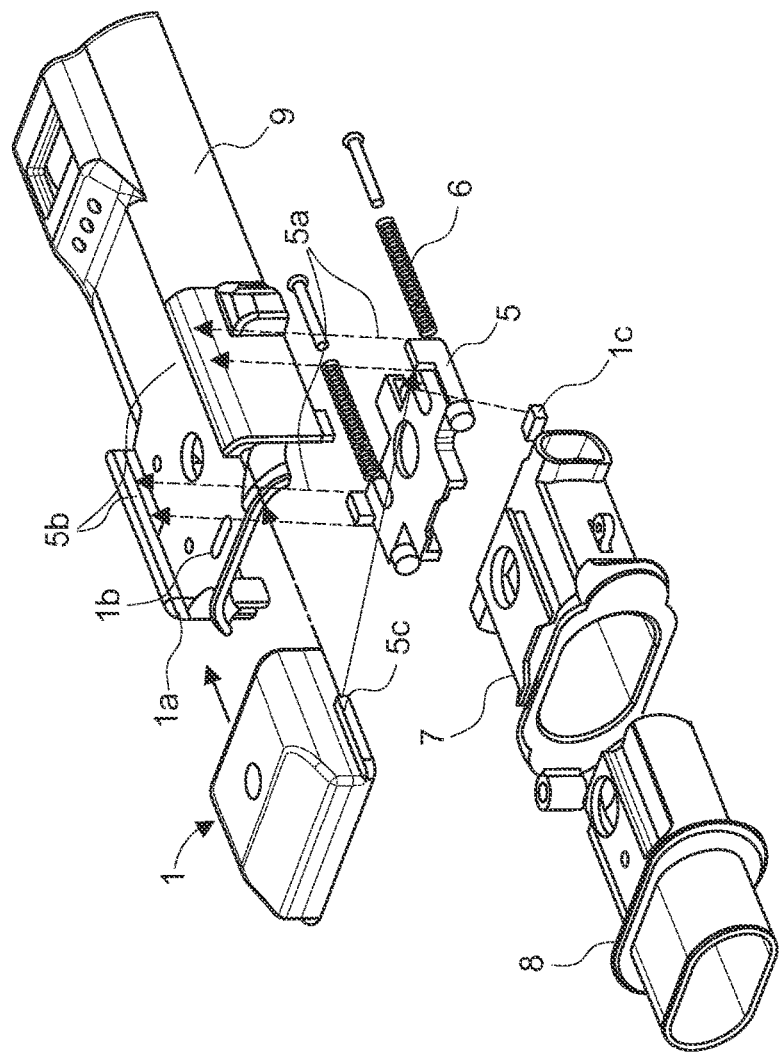
Figures 1, 3B:
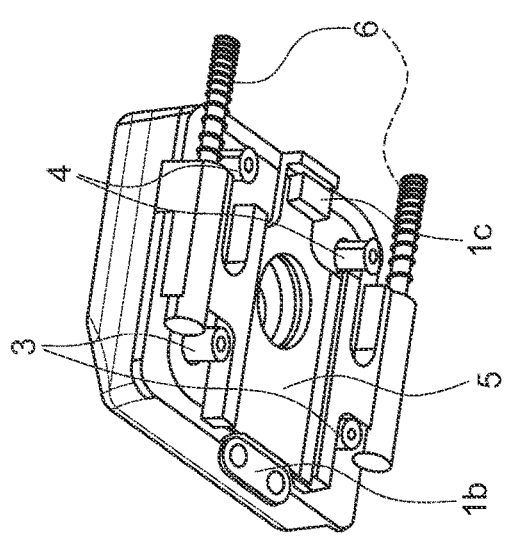

More particularly, a specific exemplary embodiment of a mode of operation of insertion of a drug ampoule and operation of a device is illustrated in FIGS. 3A-1 to FIG. 3C-3. Referring to FIGS. 3A-1 and 3A-2, when a drug ampoule (1), is initially inserted and pushed onto the device slide guide (1*a*), the device door (2) is open, the ampoule slides and clicks into ampoule position 1. An oval button (ampoule lock) (1*b*) clicks down and snaps back to lock the ampoule in place. At this setting, the seal on the aperture plate is open, the four electrical contacts on the device and ampoule make contact, and the system is powered ON, ready for breath actuation. The front two contacts (3) complete the circuit to actuate the piezoelectric element, while the rear two contacts (4) are used to provide specific information on the ampoule, such as ampoule ID, drug type, dosage, etc.

Referring to FIGS. 3B-1 and 3B-2, ampoule position 1(A) is shown, in which the oval button (1*b*) locks the ampoule into place and the four electrical contacts, front (3) and rear (4) connect to complete the electric circuit. When the ampoule is in position 1, the electronic component that activates the ON/OFF button (1*c*) is pushed by the spring-loaded, slide mechanism (5). FIG. 3B-1 provides a bottom view of the spring-loaded slide mechanism (5) and the ON/OFF button (1*c*), in the ON mode. FIG. 3B-2 provides an exploded view (5*a*) of side brackets on the spring-loaded slide (5) and their position (5*a*—dash arrows) through slots (5*b*) on the device which make contact on the ampoule (5*c*) to push the ampoule forward when the device door is opened and activate the ON/OFF switch (1*c*) as it makes contact with the ON/OFF button (1*d*). The device ON/OFF button (1*c*) is activated by the slide (5) when the mouthpiece cover (2) is closed and pushes the ampoule back to position 2, where the aperture plate seal is in the closed position and power is turned OFF to the device as pressure on the ON/OFF switch is released.

Figure 3C:
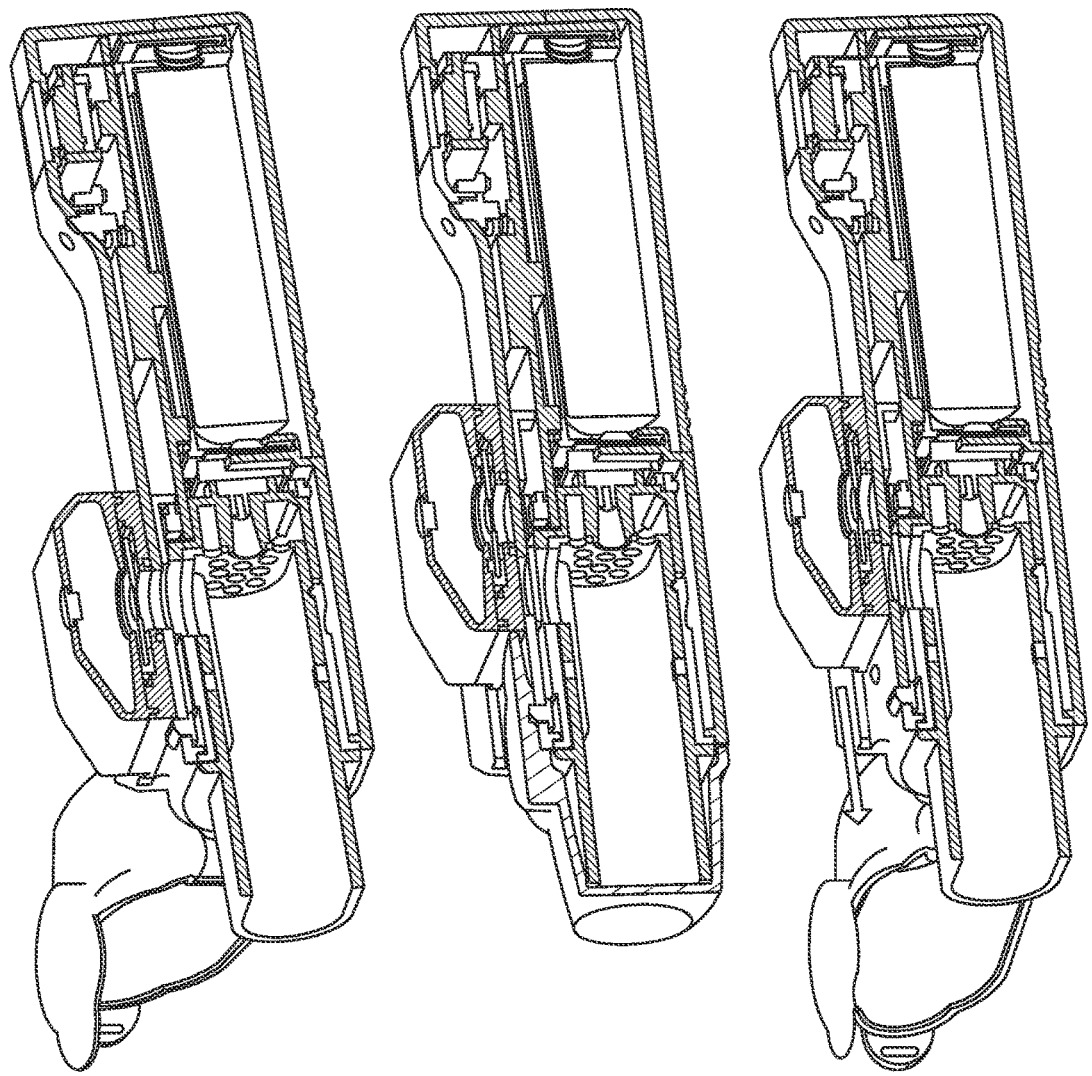

Referring to FIGS. 3C-1, 3C-2, and 3C-3, cross-sections of the device with the ampoule inserted are illustrated to better illustrate the ampoule slide mechanism and positioning of the ON/OFF switch. FIG. 3C-1 shows ampoule position 1, with the mouthpiece cover in the open position and the ON/OFF switch in the ON position. FIG. 3C-2 shows ampoule position 2, with the mouthpiece cover in the closed position and the ON/OFF switch in the OFF position. FIG. 3C-3 shows ampoule position 2, with the mouthpiece cover in the open position and the ON/OFF switch in the OFF position.

However, it is noted that the devices and methods of the disclosure are not so limited, and various modifications and expansions of the method of operation is envisioned as within the scope of the disclosure.

Figure 4A:
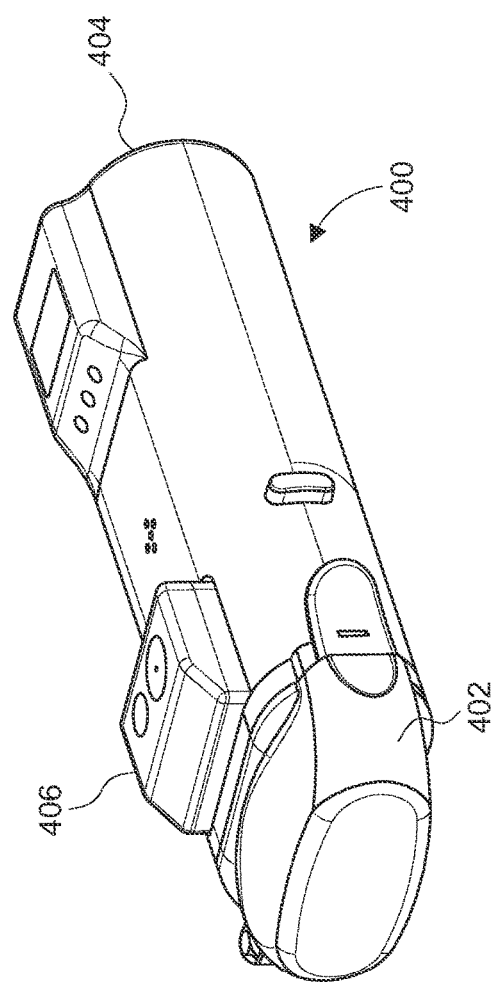
FIGS. 4A-4B illustrate perspective views of another exemplary in-line droplet delivery device, in accordance with embodiments of the disclosure.
Figure 4B:
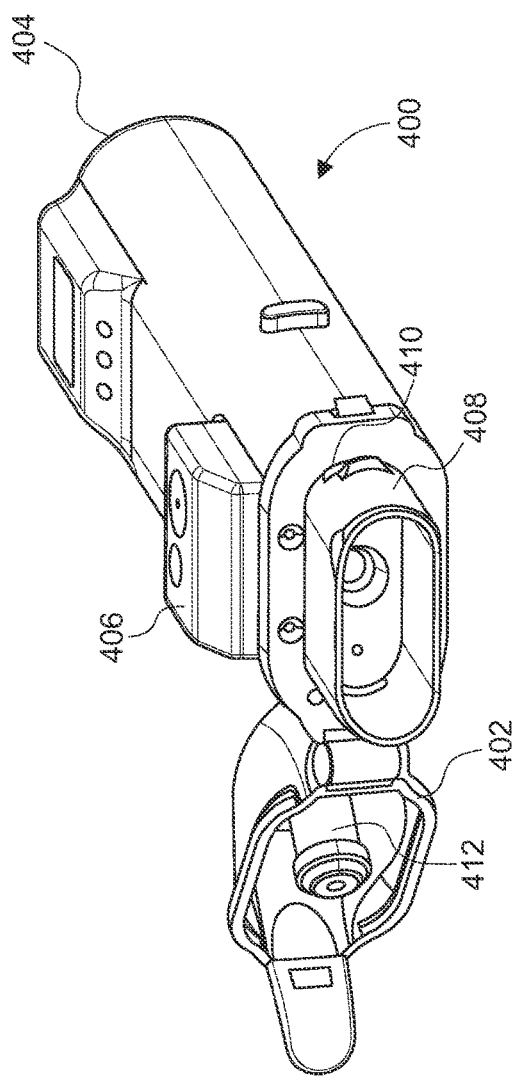

In another embodiment, FIGS. 4A and 4B illustrate an alternative in-line droplet delivery device of the disclosure, with FIG. 4A showing the in-line droplet delivery device 400 with a base unit 404 having a mouthpiece cover 402 in the closed position, and FIG. 4B with a base unit 404 having a mouthpiece cover 402 in the open position. As shown, the droplet delivery device is configured in an in-line orientation in that the housing, its internal components, and various device components (e.g., the mouthpiece, air inlet flow element, etc.) are orientated in a substantially in-line or parallel configuration (e.g., along the airflow path) so as to form a small, hand-held device.

In the embodiment shown in FIGS. 4A and 4B, the in-line droplet delivery device 400 includes a base unit 404 and a drug delivery ampoule 406. As illustrated in this embodiment, and discussed in further detail herein, the drug delivery ampoule 406 slides into the front of the base unit 404. In certain embodiments, mouthpiece cover 402 may include aperture plate plug 412. Also illustrated are one or more airflow entrances or openings 410 in mouthpiece 408. By way of example, there may be airflow entrances on the opposite side of the device, multiple airflow entrances on the same side of the device, or a combination thereof (not shown). The in-line droplet delivery device 400 also includes mouthpiece 408 at the airflow exit side of the device.

Figure 5:
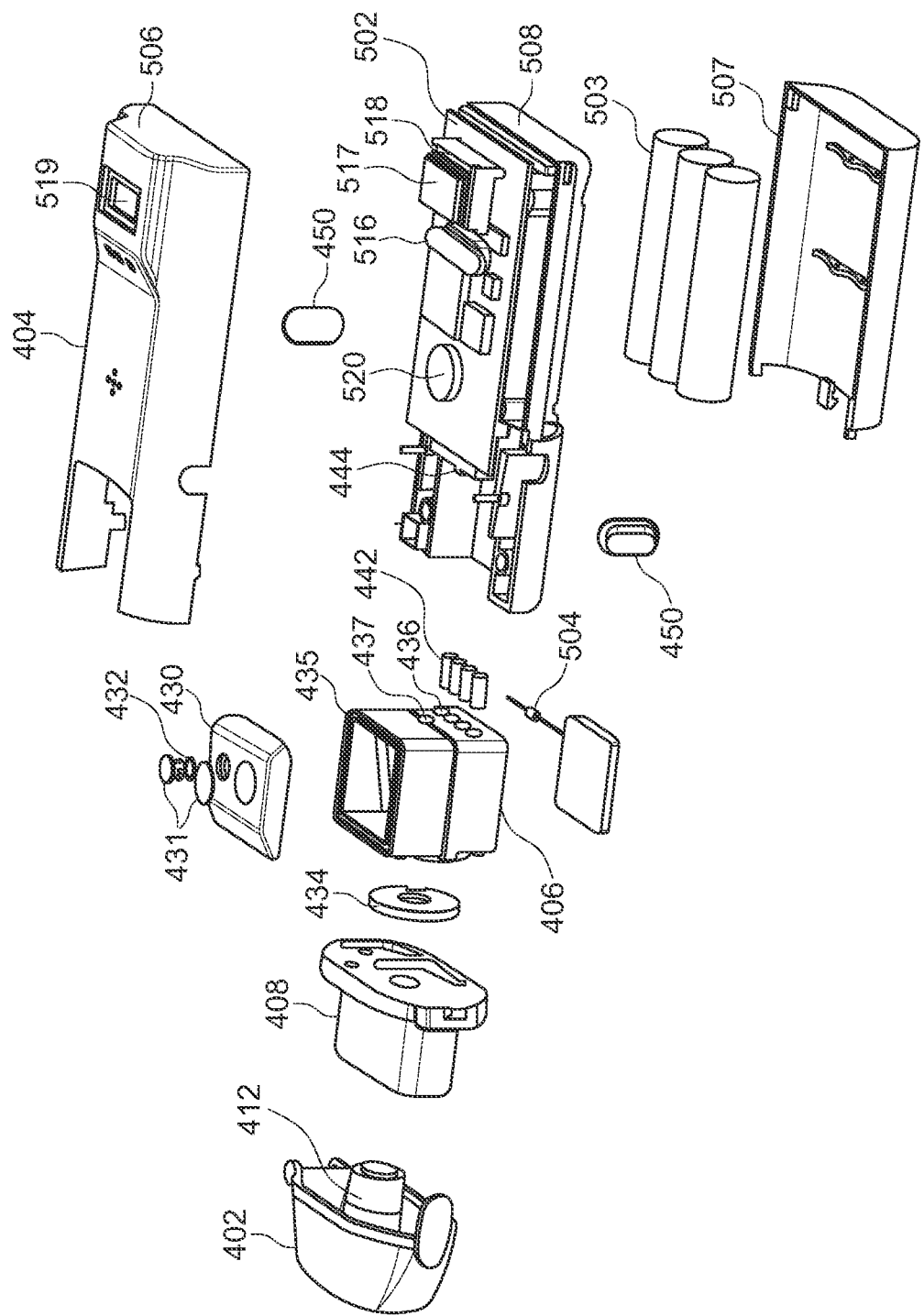
FIG. 5 is an exploded view of an in-line droplet delivery device of FIG. 4A-4B, in accordance with embodiments of the disclosure.

With reference to FIG. 5, an exploded view of the exemplary in-line droplet delivery device of FIGS. 4A and 4B is shown, including internal components of the housing including an electronics circuit board 502; a drug delivery ampoule 406 that comprises top cover 430 having optional vents 431 and vapor barriers 432, an ejector mechanism 434, a drug reservoir 435, electrical contacts 436, and one or more sensor ports 437; and a power source 503 (e.g., three AAA batteries, which may optionally be rechargeable). In certain embodiments, the device may also include various electrical contacts 442 and sensor ports 444 to facilitate activation of the device upon insertion of drug delivery ampoule 406 into the base unit 404. Likewise, in certain embodiments, the device may include resistors or chips 504 to facilitate insertion and detection of drug delivery ampoule 406 into the base unit 404.

In certain embodiments, the reservoir may be single-unit dose or multi-unit dose that may be replaceable, disposable or reusable. As illustrated in FIG. 5, in certain embodiments, the drug delivery ampoule may also comprise or be interfaced with a mouthpiece 408 and a mouthpiece cover 402. As shown, ejector mechanism 434 may be positioned in line with mouthpiece 408 and drug reservoir 435 such that the exit side of the aperture plate is perpendicular to the direction of airflow and the stream of droplets is ejected in parallel to the direction of airflow. The mouthpiece cover 402 may further include an aperture plate plug 412.

The components may be packaged in a housing, and generally oriented in an in-line configuration. The housing may be disposable or reusable, single-dose or multi-dose. Although various configurations to form the housing are within the scope of the disclosure, as illustrated in FIG. 5, the housing may comprise a top cover 506, a bottom cover 507, and an inner housing 508. The device may also include one or more ampoule release buttons 550, e.g., positioned on the side of the housing to facilitate release of the drug delivery ampoule 406 once inserted into the base unit 404.

In certain embodiments, the device may include audio and/or visual indications, e.g., to provide instructions and communications to a user. In such embodiments, the device may include a speaker or audio chip 520, one or more LED lights 516, and LCD display 517 (interfaced with an LCD control board 518 and lens cover 519). The housing may be handheld and may be adapted for communication with other devices via a Bluetooth® wireless technology communication module or similar wireless communication module, e.g., for communication with a subject's smart phone, tablet or smart device (not shown).

Figure 6:
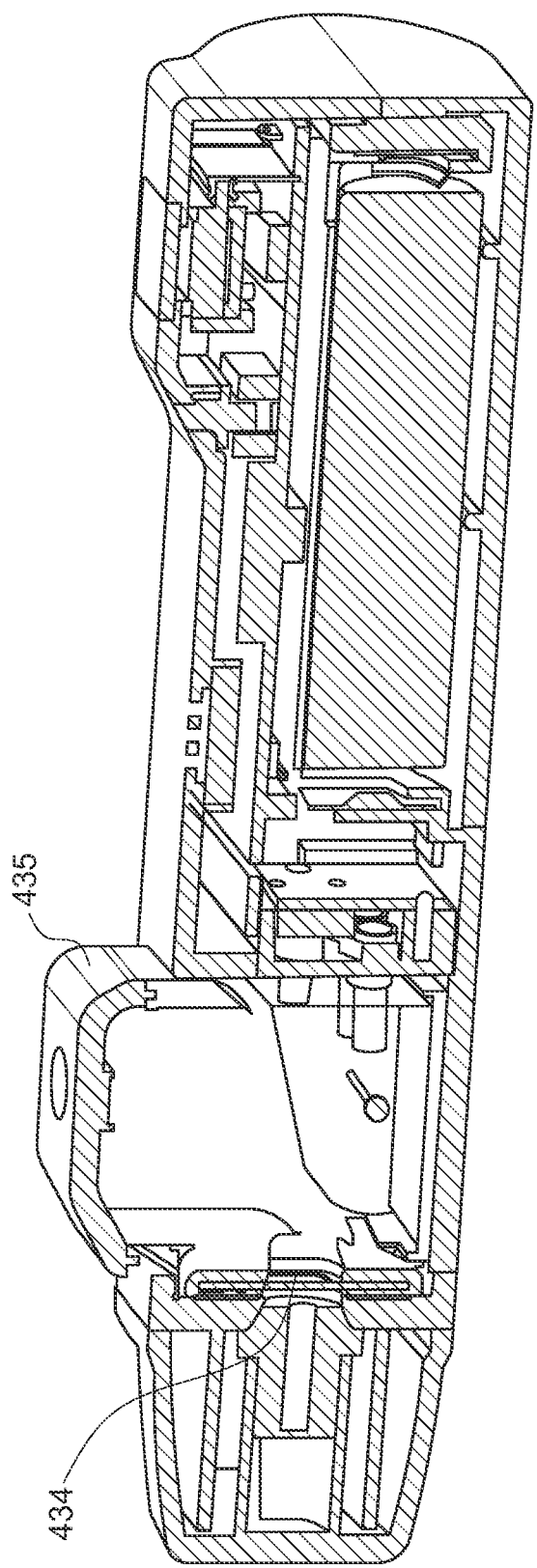
FIG. 6 is a cross section perspective view of an in-line droplet delivery device of FIG. 4A-4B, in accordance with embodiments of the disclosure.

With reference to FIG. 6, a cross-section of an in-line device of FIGS. 4A and 4B is shown to illustrate an exemplary configuration of the interior of the drug reservoir 435 and its relation to ejector mechanism 434. As shown, drug reservoir 435 may be sized and shaped such that the volume of fluid held within the reservoir is funneled and directed to the ejection surface of the aperture plate during use. More particularly, as shown, the bottom surface of the drug reservoir may be sloped towards the ejector mechanism so as to facilitate flow of the fluid within the drug reservoir during use. Without intending to be limited by theory, such configurations may be particularly suited for device orientations wherein the ejector mechanism is oriented perpendicularly to the direction of airflow. However, it is noted that the disclosure is not so limited, and various shapes, sizes and configurations of ampoule are envisioned as within the scope of the disclosure.

Figure 7:
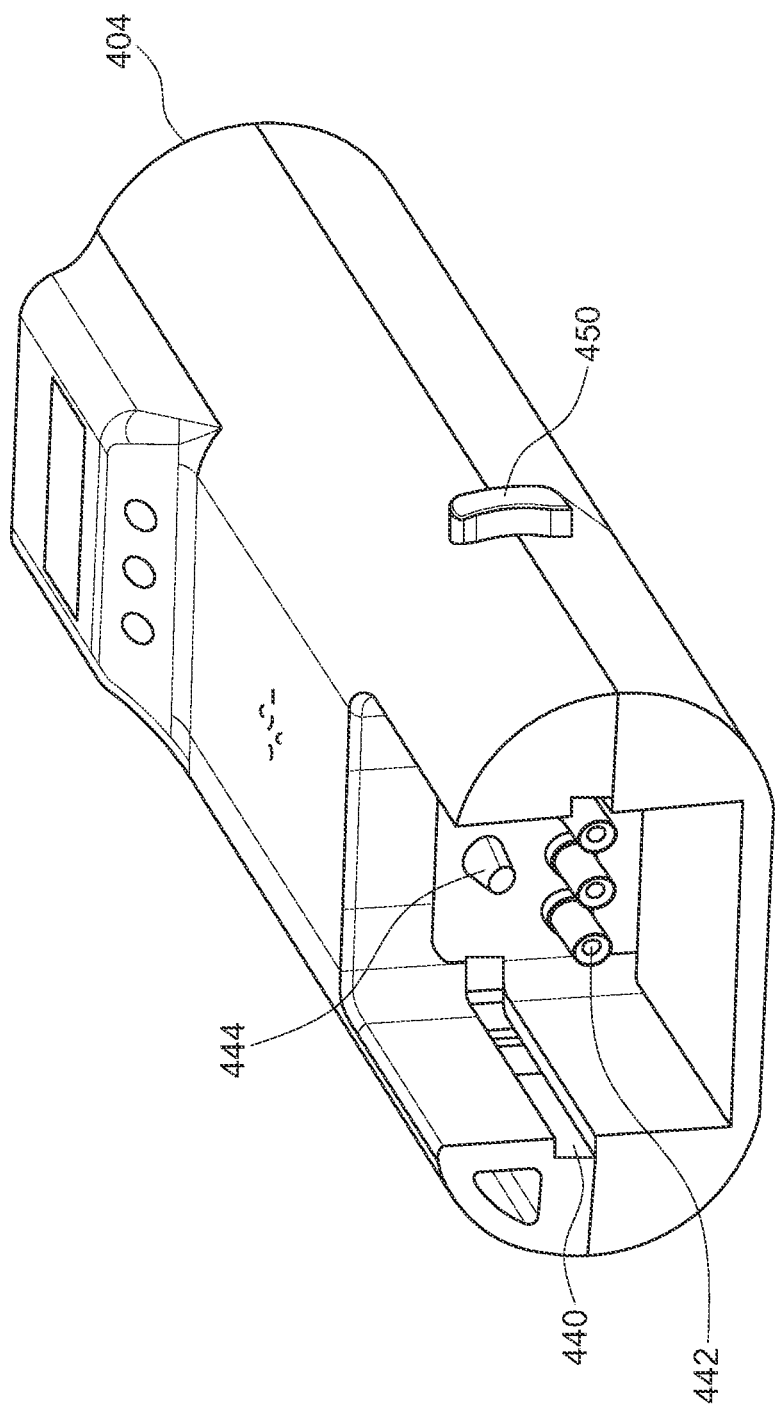
FIG. 7 is a perspective view of an in-line droplet delivery device of FIG. 4A-4B without the drug delivery ampoule inserted, in accordance with embodiments of the disclosure.

FIG. 7 illustrates the base unit 404 of the embodiment of FIGS. 4A and 4B without the drug delivery ampoule inserted. Without the drug delivery ampoule inserted, tracks 440 for directing the ampoule into place, electrical contacts 442, and sensor port 444 are shown. Also shown is release button 450.

Figure 8B:
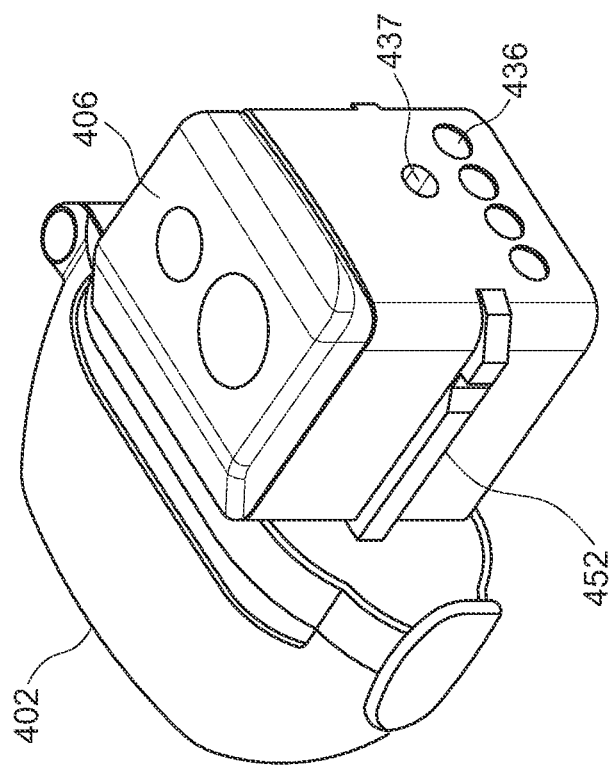
FIGS. 8A-8B are perspective views of a drug delivery ampoule and mouthpiece cover, showing a front view (FIG. 8A) and back view (FIG. 8B), in accordance with embodiments of the disclosure.
Figure 8A:
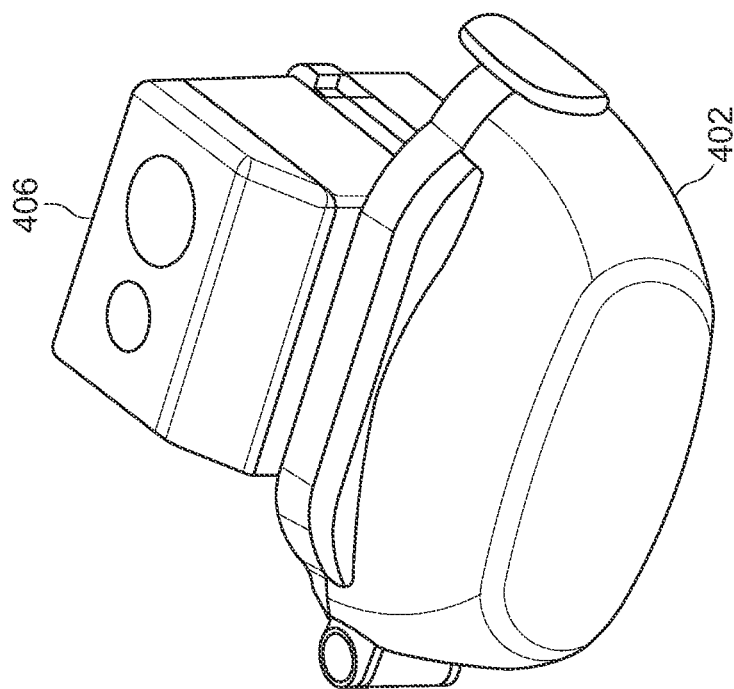

FIGS. 8A and 8B illustrate a drug delivery ampoule 406 with mouthpiece cover 402 attached and in a closed position in front view (FIG. 8A) and back view (FIG. 8B). FIG. 8B illustrates electrical contacts 436 and sensor port 437 of the ampoule, as well as protruding slides 452 to facilitate placement of the ampoule into tracks 440 during insertion. By way of example, when drug delivery ampoule 406 is inserted into base unit 404, protruding slides 452 mate with tracks 440, sensor port 437 mates with sensor port 444, and electrical contacts 436 mates with electrical contacts 442. The drug delivery ampoule is pushed into the base unit and locked into place with the protruding slides and tracks engaging one another. During use, a pressure sensor located on the control board senses pressure changes within the device via the pressure sensing ports (e.g., within the mouthpiece). To facilitate detection of pressure changes, the base unit includes a second pressure sensing port and outside channel (not shown) to facilitate sensing of reference or ambient pressure.

As discussed herein, the drug reservoir and/or drug delivery ampoule may include various vents and/or vapor barriers to facilitate venting, etc. With reference to FIGS. 9A-9C, an exemplary reservoir or ampoule is shown which is configured so as to be insensitive to pressure differentials that may occur when the user travels from sea level to sub-sea levels and at high altitudes, e.g., while traveling in an airplane where pressure differentials may be as great as 4 psi. As shown, FIG. 9A shows a perspective view of an exemplary ampoule 900. FIGS. 9B and 9C show exploded view of ampoule 900 from perspective top and bottom views. With reference to FIGS. 9B and 9C, the ampoule 900 generally includes a top cover 901 and a bottom cover 902. The ampoule 900 may be configured to include one or more superhydrophobic filter(s) 904 covering one or more vents 906, and the fluid reservoir housing may include a spiral channel (or similarly shaped) vapor barrier 905, which provides for free exchange of air into and out of the fluid reservoir, while blocking moisture or fluids from passing into the reservoir, thereby reducing or preventing fluid leakage or deposition on aperture plate surfaces. If desired, one or more O-rings 903, or similar sealing mechanism, may be used to form a seal between the top cover 901 and the bottom cover 902 in connection with the vapor barrier 905. Without intending to be limited, the superhydrophobic filter and vent may generally allow for the venting of air and equilibration of air pressure within the fluid reservoir, while maintaining a sterile environment within the fluid reservoir. The spiral channel vapor barrier will generally prevent the transfer of moisture to and from the fluid reservoir (e.g., through the vent opening).

In accordance with aspects, the in-line droplet delivery devices of the disclosure may include an air inlet flow element (see, e.g., FIGS. 10A-10C and 12A-19D) which may be positioned in the airflow at the airflow entrance of the device and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the mouthpiece. Aspects of the present embodiment further allows customizing the internal pressure resistance of the particle delivery device by allowing the placement of laminar flow elements having openings of different sizes and varying configurations to selectively increase or decrease internal pressure resistance, as will be explained in further detail herein.

In accordance with certain embodiments of the in-line droplet delivery device of the disclosure, the device may include an air inlet flow element may be positioned in the airflow at the airflow entrance of the device and configured to facilitate non-turbulent (i.e., laminar and/or transitional) airflow across the exit side of aperture plate and to provide sufficient airflow to ensure that the ejected stream of droplets flows through the droplet delivery device during use. In some embodiments, the air inlet flow element may be positioned within the mouthpiece. In addition, the air inlet flow element allows for customization of internal device pressure resistance by designing openings of different sizes and varying configurations to selectively increase or decrease internal pressure resistance.

As will be described in further detail herein, the air inlet flow element may be positioned behind the exit side of the aperture plate along the direction of airflow, or in-line or in front of the exit side of the aperture plate along the direction of airflow. In certain embodiments, the air inlet flow element comprises one or more openings formed there through and configured to increase or decrease internal pressure resistance within the droplet delivery device during use. For instance, the air inlet flow element comprises an array of one or openings. In the embodiments, the air inlet flow element comprises one or more baffles, e.g., wherein the one or more baffles comprise one or more airflow openings.

In certain embodiments, the air inlet flow element is designed and configured in order to provide an optimum airway resistance for achieving peak inspirational flows that are required for deep inhalation which promotes delivery of ejected droplets deep into the pulmonary airways. Air inlet flow elements also function to promote non-turbulent flow across the aerosol plume exit port, which also serves to stabilize airflow repeatability, stability and insures an optimal precision in the delivered dose.

Without intending to be limited by theory, in accordance with aspects of the disclosure, the size, number, shape and orientation of flow restrictions (e.g., openings, holes, flow blocks, etc.) in the air inlet flow element of the disclosure may be configured to provide a desired pressure drop within the in-line droplet delivery device. In certain embodiments, it may be generally desirable to provide a pressure drop that is not so large as to strongly affect a user's breathing or perception of breathing.

In certain implementations, the use of air inlet flow elements having differently configured, sized, and shaped flow restrictions (e.g., openings, holes, flow blocks, etc.), or the use of adjustable apertures may be required in order to accommodate the differences among the lungs and associated inspiratory flow rates of young and old, small and large, and various pulmonary disease states. For example, if the aperture is adjustable by the patient (perhaps by having a slotted ring that can be rotated), then a method may be provided to read the aperture hole setting and lock that position to avoid inadvertent changes of the aperture hole size, hence the flow measurement. Although pressure sensing is an accurate method for flow measurement, other embodiments may use, e.g., hot wires or thermistor types of flow rate measurement methods which lose heat at a rate proportional to flow rate, moving blades (turbine flow meter technology) or by using a spring-loaded plate, without limitation of example.

Figure 10C:
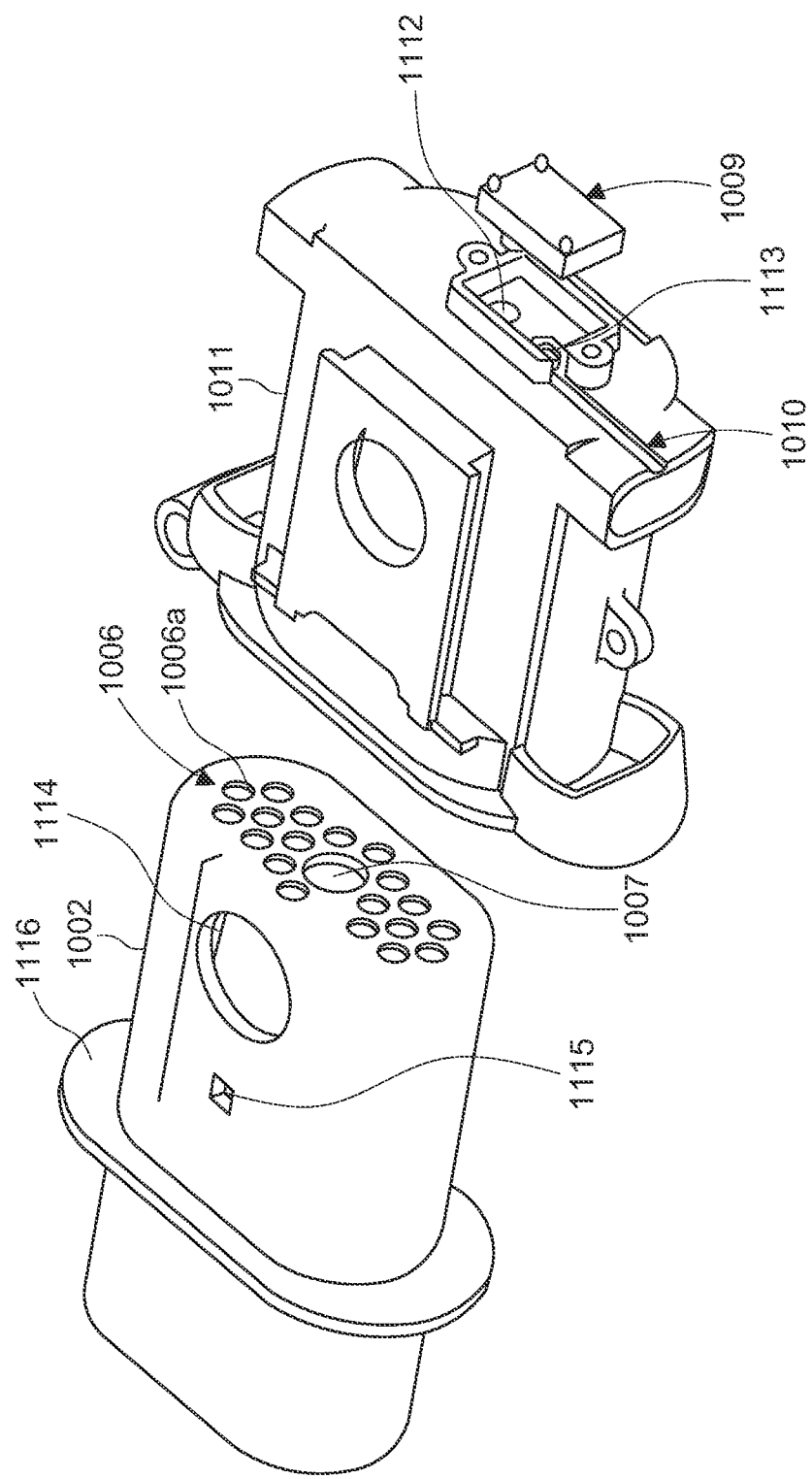
FIG. 10C is a exploded view of components of an in-line droplet delivery device of FIG. 1A-1B including a mouthpiece and internal housing, in accordance with an embodiment of the disclosure.

For instance, FIGS. 10A-10C illustrate certain exemplary air inlet flow elements of the disclosure. FIGS. 10A-10C also illustrate the position of pressure sensors, the mouthpiece, and air channels for reference pressure sensing. However, the disclosure is not so limited, and other configurations including those described herein are contemplated as within the scope of the disclosure. While not being so limited, the air inlet flow elements of FIGS. 10A-10C are particularly suitable for use with the in-line droplet delivery devices of FIGS. 1A-1B.

More particularly, FIG. 10A illustrates a cross-section of a partial in-line droplet delivery device 1000 of the disclosure including a mouthpiece cover 1001, a mouthpiece 1002, a drug delivery ampoule 1003 comprising a drug reservoir 1004 and an ejector mechanism 1005. As illustrated, the droplet delivery device includes an air inlet flow element 1006 having an array of holes 1006a at the air entrance of the mouthpiece 1002. Also shown is a pressure sensor port 1007, which may be used to sense a change in pressure within the mouthpiece. With reference to FIG. 10B, a front view of the device 1000 is illustrated, wherein a second pressure sensor port 1008 is shown to provide for sensing of a reference or ambient pressure.

FIG. 10C illustrates a partial exploded view including mouthpiece 1002 and inner housing 1011. As shown, mouthpiece 1002 includes air intake flow element 1006 with an array of holes 1006a, and pressure sensor port 1007. Further, mouthpiece 1002 may include an ejection port 1114 positioned, e.g., on the top surface of the mouthpiece so as to align with the ejector mechanism to allow for ejection of the stream of droplets into the airflow of the device during use. Other sensor ports 1115 may be positioned as desired along the mouthpiece to allow for desired sensor function, e.g., spray detection. The mouthpiece may also include positioning baffle 1116 that interfaces with the base unit upon insertion. Inner housing 1011 includes pressure sensor board 1009 and outside channel 1010 for facilitating sensing of reference or ambient pressure. The inner housing further includes a first pressure sensing port 1112 to facilitate sensing of pressure changes within the device (e.g., within the mouthpiece or housing), and a second pressure sensing port 1113 to facilitate sensing of reference or ambient pressure.

Figure 11A:
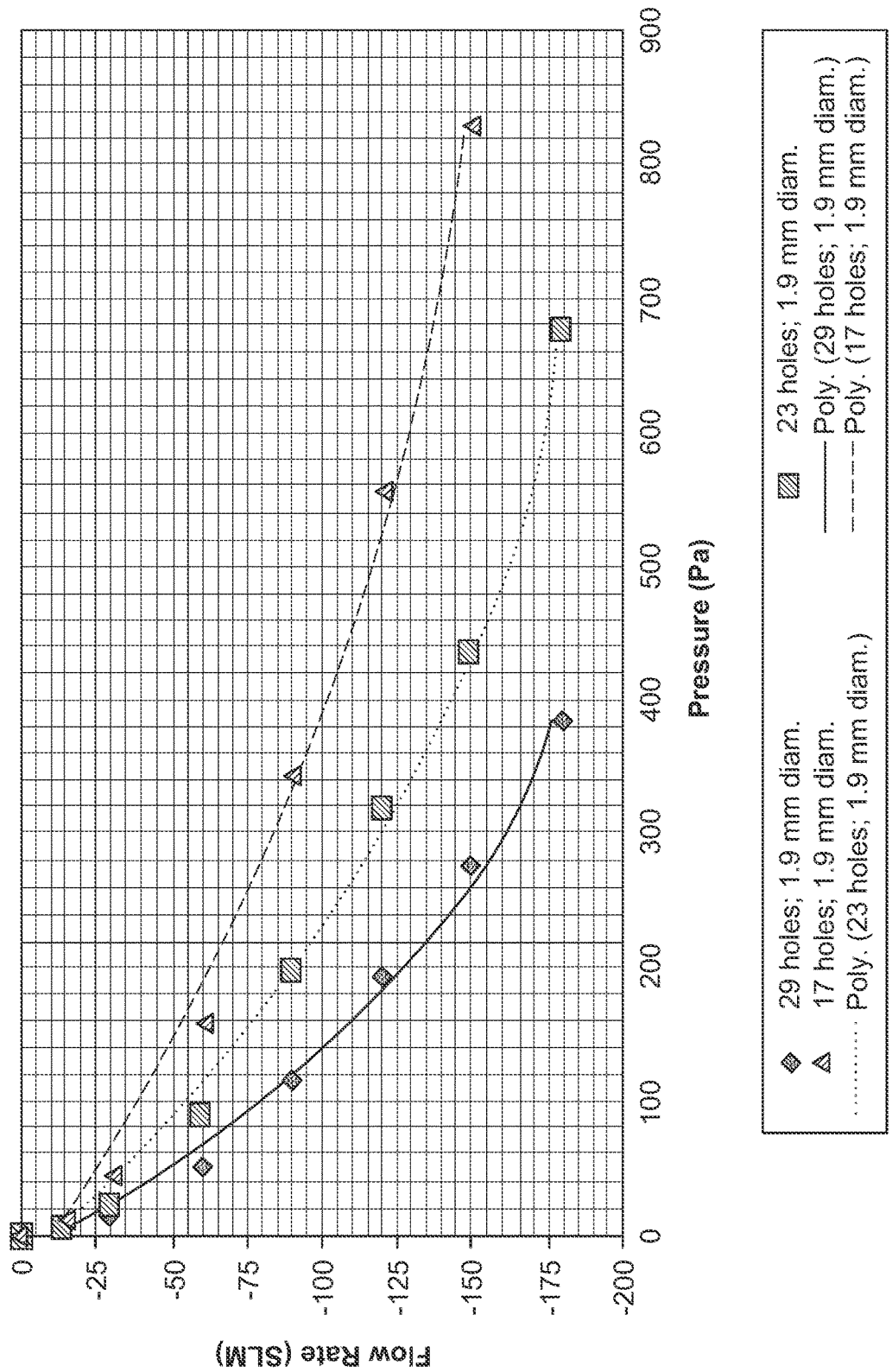
FIG. 11A is a plot of the differential pressure as a function of flow rates through exemplary air inlet flow elements as a function of number of holes, in accordance with an embodiment of the disclosure.
Figure 11B:
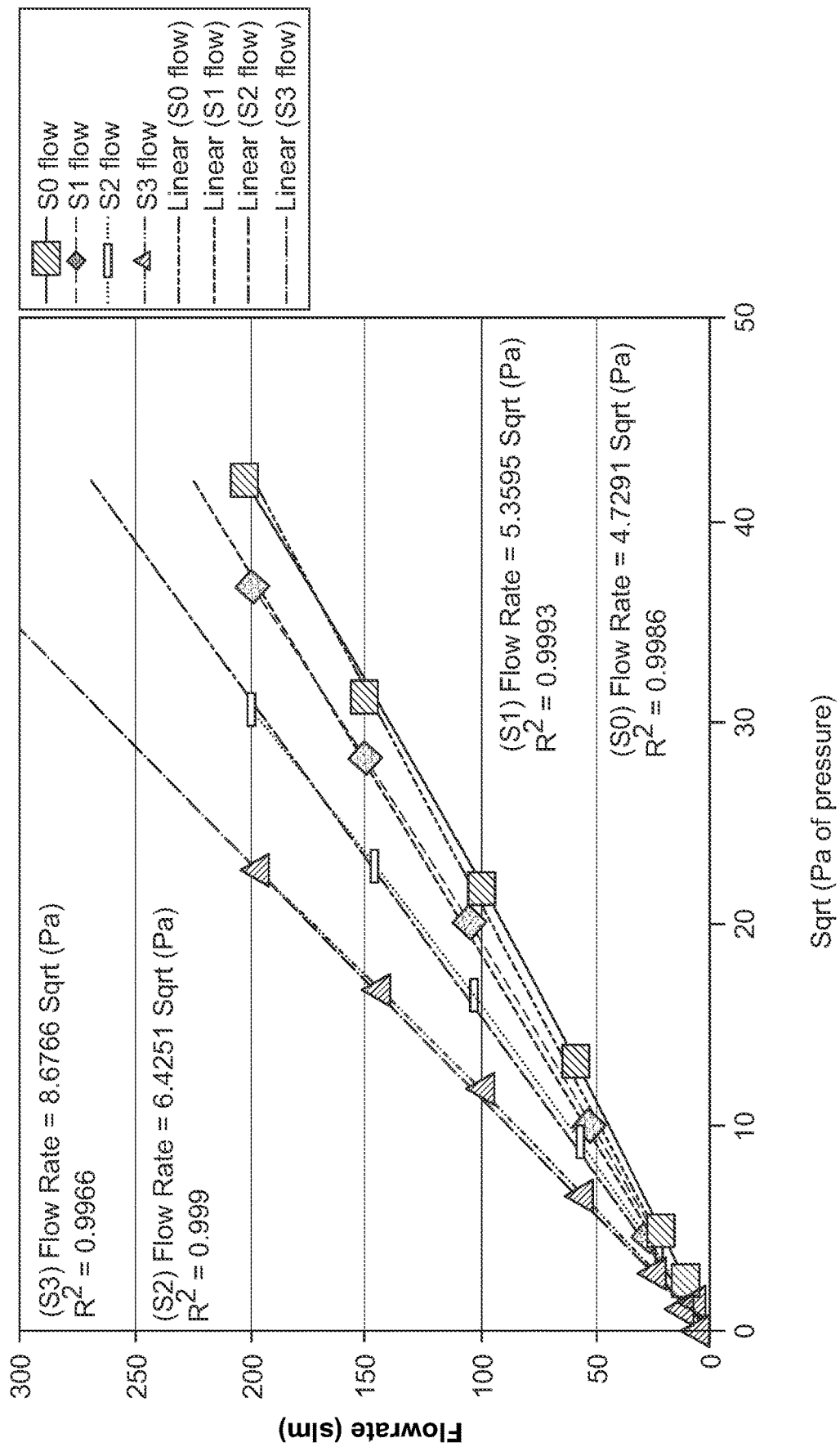
FIG. 11B is a plot of the differential pressure as a function of flow rates through exemplary air inlet flow elements as a function of screen hole size and number of holes set at a constant, 17 holes, in accordance with an embodiment of the disclosure.

In this regard, FIG. 11A illustrates differential pressure as a function of flow rates through exemplary air inlet flow elements similar to that of FIGS. 10A-10C as a function of number of holes (29 holes, 23 holes, 17 holes). Referring to FIG. 11B, the flow rate verses differential pressure as a function of hole size is shown to have a liner relationship, when flow rate is plotted as a function of the square root of differential pressure. The number of holes is held constant at 17 holes. These data provide a manner to select a design for an air inlet flow element to provide a desired pressure resistance, as well as provide a model for the relationship between flow rate and differential pressure, as measured in an exemplary droplet delivery device.

Inspiratory Flow Rate (SLM)=C(SqRt) (Pressure (Pa))

| Element # | Hole Size (mm) (17 holes) | Pressure at 10 slm (Pa) | Flow at 1000 Pa | Equation Constant (C) |
|---|---|---|---|---|
| 0 | 1.9 | 6 | 149.56 | 4.73 |
| 1 | 2.4 | 2.1 | 169.48 | 5.36 |
| 2 | 2.7 | 1.7 | 203.16 | 6.43 |
| 3 | 3 | 1.3 | 274.46 | 8.68 |

A particular non-limiting exemplary air inlet flow element may 29 holes, each 1.9 mm in diameter. However, the disclosure is not so limited. For example, the air inlet flow element may have hole diameters ranging from, e.g., 0.1 mm in diameter to diameters equal to the cross sectional diameter of the air inlet tube (e.g., 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, etc.), and number of holes may range from 1 to the number of holes, for example, to achieve the desire air flow resistance, e.g., 2, 3, 4, 5, 6, 7, 8, 9, 10, 15, 20, 25, 29, 30, 60, 90, 100, 150, etc.

FIGS. 12A-19D illustrate alternative embodiments of air inlet flow elements of the disclosure. FIGS. 12A-19D also illustrate exemplary positioning of air inlet flow elements within the airflow of a device, within the mouthpiece, as well as the interfacing of a mouthpiece including an air inlet flow element to an drug delivery ampoule.

Figure 12C:
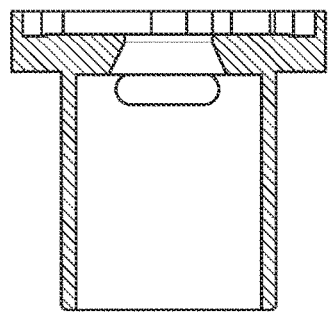
FIG. 12B shows a front cross-section and FIG. 12C shows a side cross-section, with FIG. 12D showing the same views with exemplary dimensions.
Figure 12B:
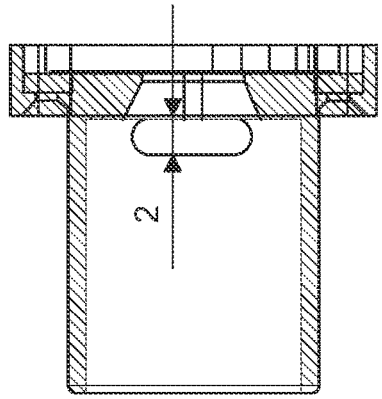
Figure 12A:
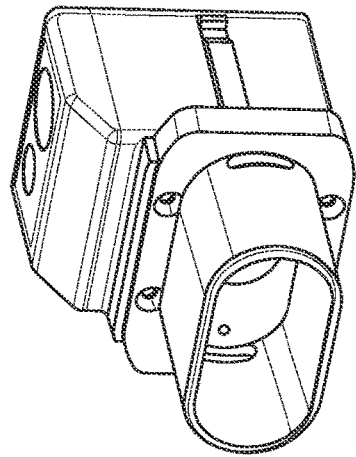
FIG. 12A shows an exemplary drug delivery ampoule with a mouthpiece interfaced at the airflow exit side of the device, in accordance with an embodiment of the disclosure.
Figure 12D:
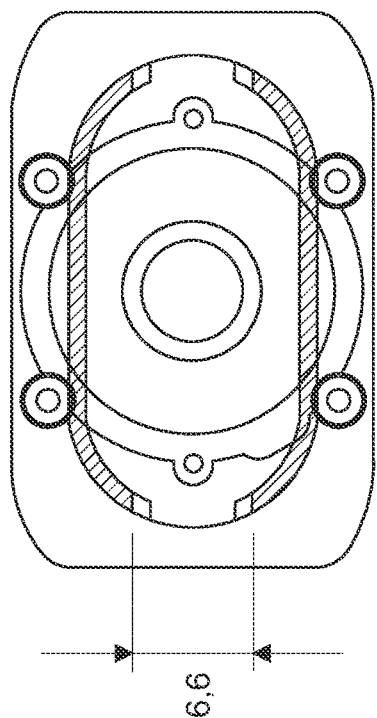
Figure 13C:
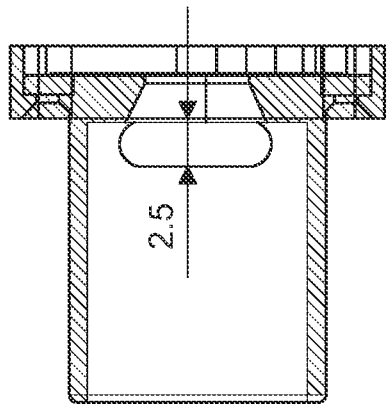
FIG. 13B shows a front cross-section and FIG. 13C shows a side cross-section, with FIG. 13D showing the same views with exemplary dimensions.
Figure 13B:
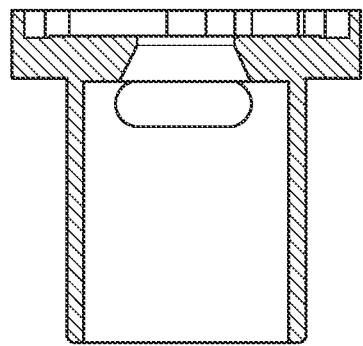
Figure 13D:
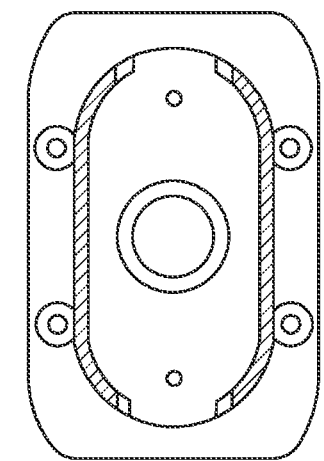
FIG. 13A shows an alternative drug delivery ampoule with a mouthpiece interfaced at the airflow exit side of the device, in accordance with an embodiment of the disclosure.
Figure 13A:
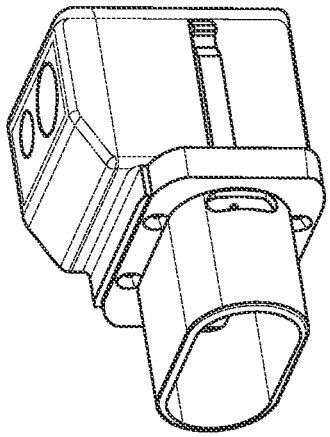

FIG. 12A shows an exemplary drug delivery ampoule with a mouthpiece interfaced at the airflow exit side of the device. The mouthpiece includes two airflow entrances on the sides, but no internal air inlet flow elements to provide resistance to airflow. FIG. 12B shows a front cross-section and 12C shows a side cross-section, with FIG. 12D showing the same views with exemplary dimensions. FIGS. 13A and 14A show similarly configured mouthpieces with two airflow entrances on the sides, but no internal air inlet flow elements to provide resistance to airflow. Again, FIGS. 13B and 14B show a front cross-section and 13C and 14C show a side cross-section, with FIGS. 13D and 14D showing the same views with exemplary dimensions to illustrate the differences in configurations between the embodiments. For instance, the embodiment of FIG. 12 has openings that are 6.6 mm long and 2 mm high, the embodiment of FIG. 13 has openings that are 7.9 mm long and 2.5 mm high, and the embodiment of FIG. 14 has openings that are 8.1 mm long and 3 mm high. Of course, the disclosure is not limited to these specific dimensions, and varied dimensions and numbers of air inflow openings are envisions as within the scope of the disclosure.

Figure 15C:
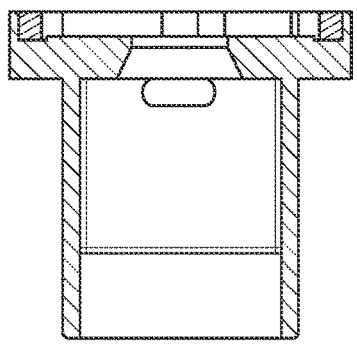
FIG. 15B shows a front cross-section and FIG. 15C shows a side cross-section, with FIG. 15D showing the same views with exemplary dimensions.
Figure 15D:
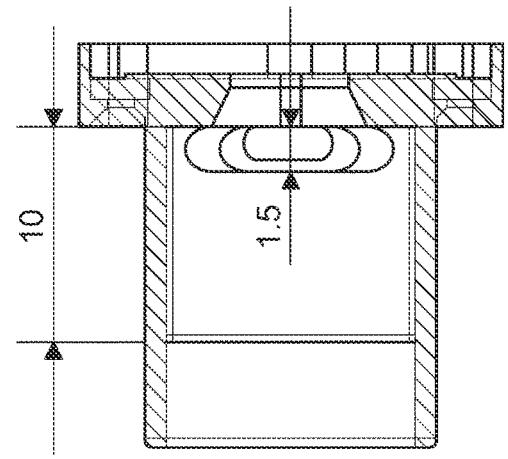
FIG. 15A shows an exemplary drug delivery ampoule with a mouthpiece interfaced at the airflow exit side of the device, in accordance with an embodiment of the disclosure. The mouthpiece includes two airflow entrances on the exterior sides of the mouthpiece, and two interior baffles with additional airflow entrances to provide resistance and modeling of airflow.
Figure 15B:
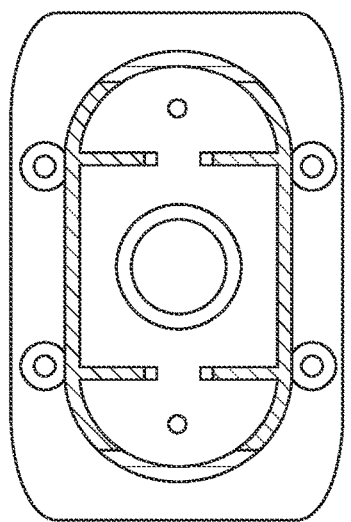
Figure 15A:
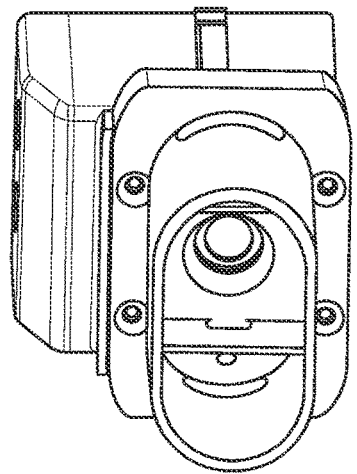
Figure 20:
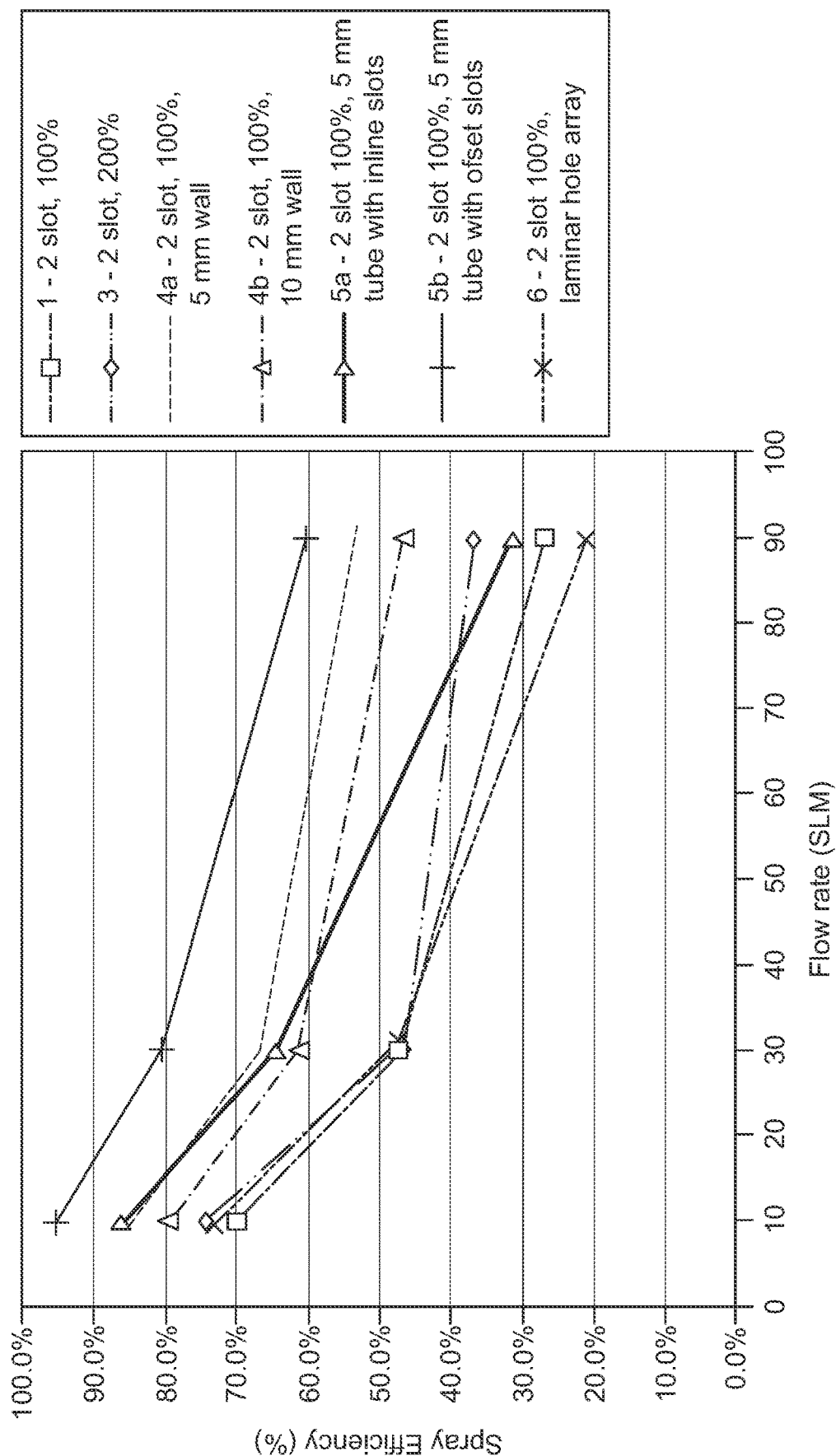
FIG. 20 is a plot of spray efficiency as a function of flow rates through exemplary air inlet flow elements as a function of number and configuration of openings, baffles, etc., in accordance with an embodiment of the disclosure.
Figure 21A:
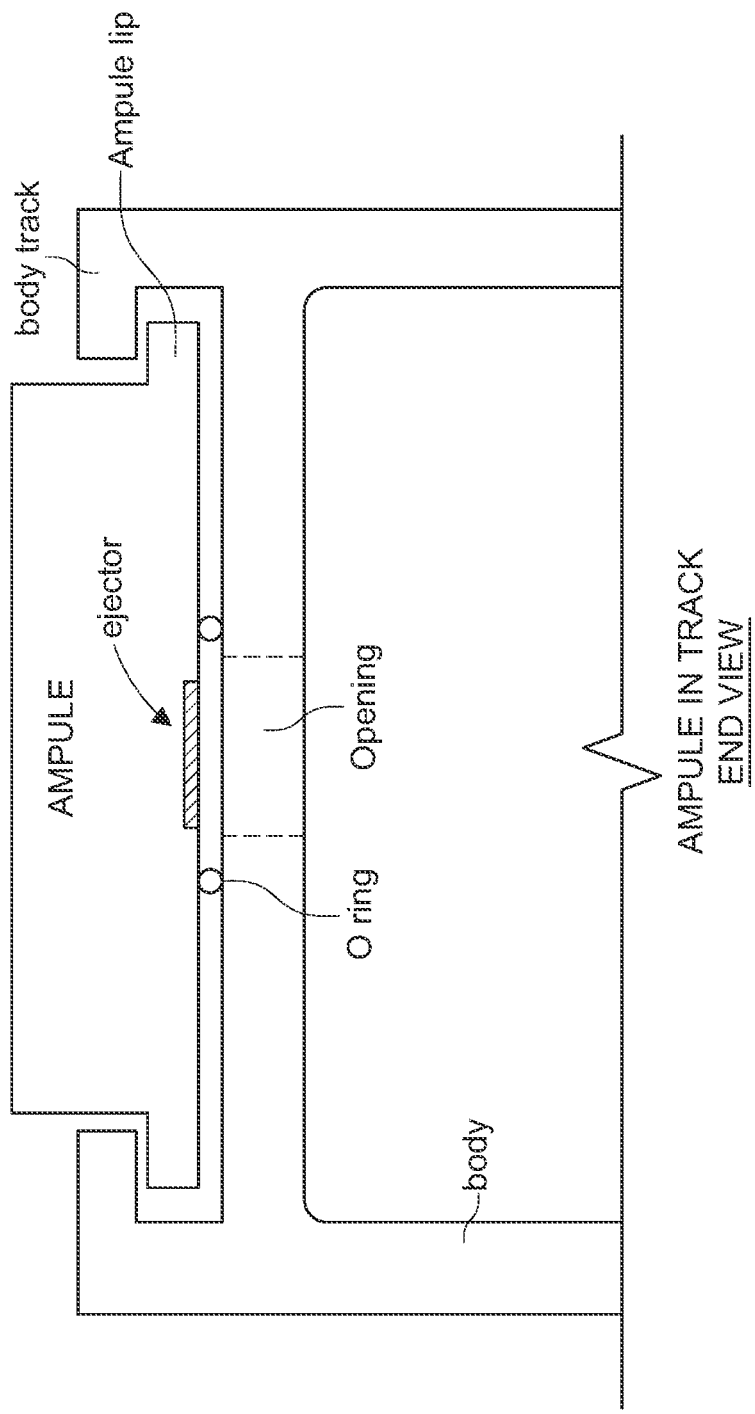
Figure 21B:
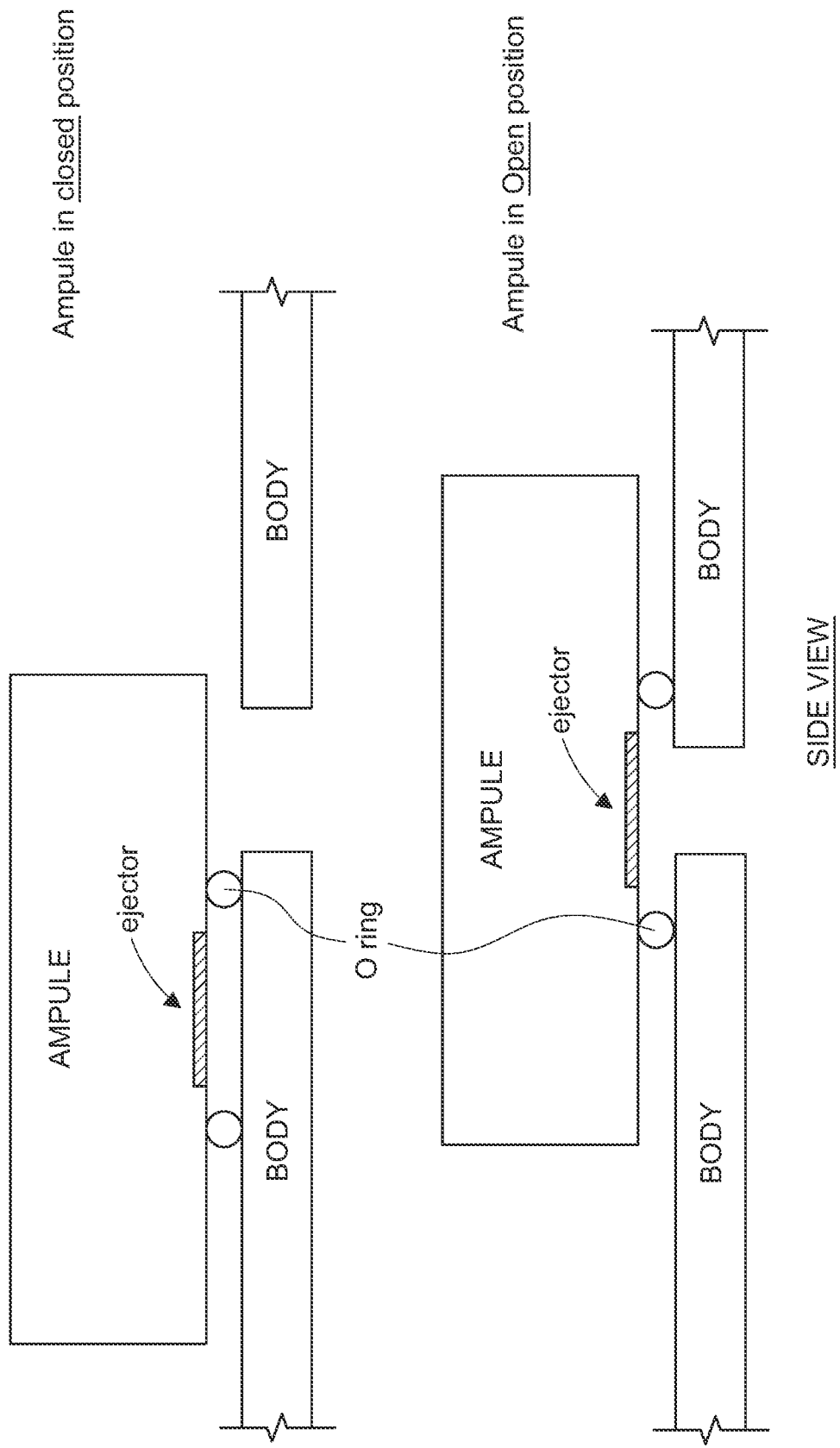
Figure 21D:
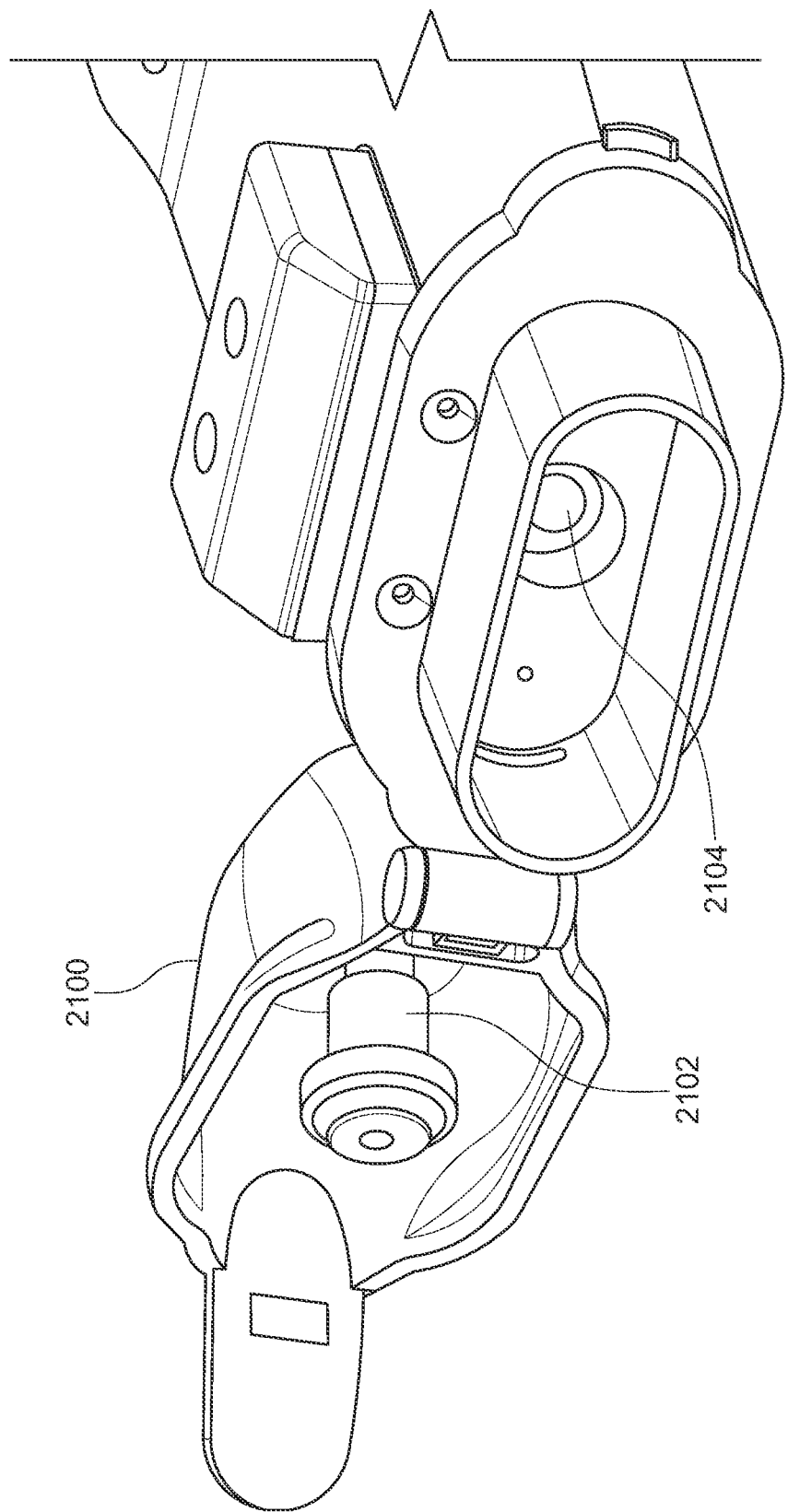

FIG. 15A shows an exemplary drug delivery ampoule with a mouthpiece interfaced at the airflow exit side of the device. The mouthpiece includes two airflow entrances on the exterior sides of the mouthpiece, and two interior baffles with additional airflow entrances to provide resistance and modeling of airflow. FIG. 15B shows a front cross-section and 15C shows a side cross-section, with FIG. 15D showing the same views with exemplary dimensions. FIG. 16A shows a similarly configured mouthpiece that includes two airflow entrances on the exterior sides of the mouthpiece, and two interior baffles with additional airflow entrances to provide resistance and modeling of airflow. However, the interior baffles of FIG. 16A are larger (10 mm in height) than that of FIG. 15A (5 mm in height). FIG. 16B shows a front cross-section and 16C shows a side cross-section, with FIG. 16D showing the same views with exemplary dimensions.

FIG. 17A shows an exemplary drug delivery ampoule with a mouthpiece interfaced at the airflow exit side of the device. The mouthpiece includes two airflow entrances on the exterior sides of the mouthpiece, and a substantially concentric baffle (two arcs that form a circle with the top and bottom of the mouthpiece) with two additional airflow entrances to provide resistance and modeling of airflow. FIG. 17B shows a front cross-section and 17C shows a side cross-section, with FIG. 17D showing the same views with exemplary dimensions. FIG. 18A shows a similarly configured mouthpiece with a substantially concentric interior baffle, but the interior baffle includes four airflow entrances to provide resistance and modeling of airflow. FIG. 18B shows a front cross-section and 18C shows a side cross-section, with FIG. 18D showing the same views with exemplary dimensions.

FIG. 19A shows an exemplary drug delivery ampoule with a mouthpiece interfaced at the airflow exit side of the device. The mouthpiece includes two airflow entrances on the exterior sides of the mouthpiece, and a substantially concentric baffle with two additional airflow entrances to provide resistance and modeling of airflow. In addition, the interior area of the mouthpiece between the concentric baffle and the wall of the mouthpiece includes an array element positioned above the airflow entrances to provide additional resistance and modeling to airflow. The array element is positioned in a parallel arrangement with the direction of airflow. Again, FIG. 19B shows a front cross-section and 19C shows a side cross-section, with FIG. 19D showing the same views with exemplary dimensions.

In accordance with the disclosure, it has been found that the presence of inner air inlet flow elements generally improve spray efficiency for exemplary fluid solutions (deionized water and albuterol solution. For instance, as shown in FIG. 20, at 30 SLM, inner air inlet flow elements increase spray efficiency from 47% to 66%, and orienting interior airflow entrances away from ejection streams improves spray efficiency to 80% or more. The mouthpiece and drug reservoir are a single unit and can be weighted before ejection (W1), after ejection (W2) and after drying (W3) the mouthpiece to measure the percentage of ejected drug that leaves the mouthpiece for delivery to a user. Spray efficiency=(W1−W2)/(W1−W3)

In certain aspects of the disclosure, the in-line device may be configured to protect the surface of the aperture plate, to minimize evaporation losses, and to minimize contamination while the device is closed and not in use. For instance, as described herein, when the reservoir/ampoule is in the closed position, the surface of the aperture plate of the ejector mechanism may be closed/sealed against the housing or the mouthpiece cover. However, in certain embodiments, when the reservoir/ampoule includes an O-ring or gasket to facilitate the seal of the surface of the aperture plate of the ejector mechanism, the sliding of the reservoir/ampoule between the open and closed position may, in certain aspects, create friction which needs to be overcome by a compression spring during opening and closing.

In one embodiment, friction between the ampoule O-ring and the device housing may be reduced by applying a compressive force between the ampoule and the device housing in the last few millimeters as the ampoule is closed. Thus, higher friction is limited to the first few millimeters during opening, when the compression spring is providing the highest force; and during the last few millimeters of closing when the ampoule door is almost closed and force on the door is easiest for the user to apply. Force applied as the door is almost closed also creates minimal reaction forces at the door's hinge, improving robustness of the device. Applying pressure to the O-ring over a shorter distance also reduces wear on the O-ring (or gasket).

Without being limited, in certain embodiments, applying a compressive sealing force during the last few millimeters of ampoule motion to the closed position can be accomplished by utilizing a ramp on either the ampoule or device side of the ampoule track which engages a budge on the opposite face (device for ampoule or ampoule for device) as the ampoule approaches the closed position. This can also be a pair of ramps which engage as the ampoule approaches the closed position. In certain aspects, the point(s) of contact between the ampoule and device should be in alignment with the center of pressure of the O-ring to create a uniform sealing pressure. Note that to achieve enough compression for good sealing, the total vertical motion created by the ramp only needs to be in the range of 0.1 mm.

Alternatively to a sealing force generated by a fixed movement of the ampoule towards the device, a flexible compressive element can apply a downward force the rises as the ampoule approaches the closed position. By way of non-limiting example, this could be the ramp intersecting a flexible, rubber-like, material or a metallic or plastic spring, including a cantilever (leaf) spring that the ramp encounters as it arrives at the closed position of the ampoule.

The compressive force applied to the O-ring does not have to be large, but sufficient for the compliant O-ring to seal against the surface roughness of the device surface. In certain embodiments, a more compliant material will require less compressive force to seal. Similarly, the O-ring can be made from a slippery material such as teflon-coated or teflon-encapsulated material to reduce the sliding friction of the ampoule. Similarly, sealing may be done by a lip seal at the face.

FIGS. 21A-21C illustrate exemplary embodiments showing a ramp structure on the ampoule lip that presses the ampoule down and compresses the O-ring while in the "closed" position. Note, as illustrated the size of the ramp is greatly exaggerated. In one embodiment, the ramp may be about 0.1 to 0.2 mm high. FIG. 21A shows an end view showing ampoule with lips that are engaged in track that is part of body of device. FIG. 21B shows how an ampoule moves from closed to open position. Mouthpiece and user to the right. FIG. 21C illustrates a side view of an ampoule in track with a ramp on a lip to force a aperture plate seal, showing a closed and open position.

In other embodiments, the surface of the aperture plate may be protected by the mouthpiece cover. For instance, as shown in FIG. 21D, mouthpiece cover 2100 may include aperture plate plug 2102 that is specifically sized and shaped so as to form a mating seal against the surface of the aperture plate 2104 when the cover is closed. In certain embodiments, the aperture plate plug 2102 may have a stepped shape such that the plug forms a seal against the surface of the housing around the aperture plate without putting direct pressure on the surface of the aperture plate.

In certain embodiments, as illustrated herein, the reservoir/cartridge module may include components that may carry information read by the housing electronics including key parameters such as ejector mechanism functionality, drug identification, and information pertaining to patient dosing intervals. Some information may be added to the module at the factory, and some may be added at the pharmacy. In certain embodiments, information placed by the factory may be protected from modification by the pharmacy. The module information may be carried as a printed barcode or physical barcode encoded into the module geometry (such as light transmitting holes on a flange which are read by sensors on the housing). Information may also be carried by a programmable or non-programmable microchip on the module which communicates to the electronics in the housing.

By way of example, module programming at the factory or pharmacy may include a drug code which may be read by the device, communicated via Bluetooth® wireless technology to an associated user smartphone and then verified as correct for the user. In the event a user inserts an incorrect, generic, damaged, etc., module into the device, the smartphone might be prompted to lock out operation of the device, thus providing a measure of user safety and security not possible with passive inhaler devices. In other embodiments, the device electronics can restrict use to a limited time period (perhaps a day, or weeks or months) to avoid issues related to drug aging or build-up of contamination or particulates within the device housing.

The in-line droplet delivery device may further include various sensors and detectors to facilitate device activation, spray verification, patient compliance, diagnostic mechanisms, or as part of a larger network for data storage, big data analytics and for interacting and interconnected devices used for subject care and treatment, as described further herein. Further, the housing may include an LED assembly on a surface thereof to indicate various status notifications, e.g., ON/READY, ERROR, etc.

The airflow exit of the housing of the droplet delivery device through which the ejected plume of droplets exit as they are inhaled into a subject's airways, may be configured and have, without limitation, a cross sectional shape of a circle, oval, rectangular, hexagonal or other shape, while the shape of the length of the tube, again without limitation, may be straight, curved or have a Venturi-type shape.

In another embodiment (not shown), a mini fan or centrifugal blower may be located at the air inlet side of the laminar flow element or internally of the housing within the airsteam. The mini fan generally may provide additional airflow and pressure to the output of the plume. For patients with low pulmonary output, this additional airplume may ensure that the plume of droplets is pushed through the device into the patient's airway. In certain implementations, this additional source of airflow ensures that the plume exit port is swept clean of the droplets and also provides mechanism for spreading the particle plume into an airflow which creates greater separation between droplets. The airflow provided by the mini fan may also act as a carrier gas, ensuring adequate dose dilution and delivery.

In other embodiments, the internal pressure resistance of the in-line droplet delivery device may be customized to an individual user or user group by modifying the mouthpiece tube design to include various configurations of air aperture grids or openings, thereby increasing or decreasing resistance to airflow through the device as the user inhales. For instance, different air entrance aperture sizes and numbers may be used to achieve different resistance values, and thereby different internal device pressure values. This feature provides a mechanism to easily and quickly adapt and customize the airway resistance of the particle delivery device to the individual patient's state of health or condition.

In another aspect of the disclosure, in certain embodiments, the in-line droplet delivery devices provide for various automation, monitoring and diagnostic functions. By way of example, as described above, device actuation may be provided by way of automatic subject breath actuation. Further, in certain embodiments, the device may provide automatic spray verification, to ensure that the device has generated the proper particle generation and provided to proper dosing to the subject. In this regard, the particle delivery device may be provided with one or more sensors to facilitate such functionality.

For instance, an airflow sensor located in the mouthpiece may measure inspiratory and expiratory flow rates. This sensor is placed so that it does not interfere with drug delivery or become a site for collection of residue or promote bacterial growth or contamination. A differential (or gage) pressure sensor downplume of a flow restrictor (e.g., air inlet flow element) measures airflow based upon the pressure differential between the inside of the mouthpiece relative to the outside air pressure. During inhalation (inspiratory flow) the mouthpiece pressure will be lower than the ambient pressure and during exhalation (expiratory flow) the mouthpiece pressure will be greater than the ambient pressure. The magnitude of the pressure differential during an inspiratory cycle is a measure of the magnitude of airflow and airway resistance at the air inlet end of the delivery tube.

Again, a Bluetooth® wireless technology communication module or similar wireless communication module may be provided in order to link the droplet delivery device to a smartphone or other similar smart devices (not shown). Bluetooth® wireless technology connectivity facilitates implementation of various software or App's which may provide and facilitate patient training on the use of the device. A major obstacle to effective inhaler drug therapy has been either poor patient adherence to prescribed aerosol therapy or errors in the use of an inhaler device. By providing a real time display on the smartphone screen of a plot of the patient's inspiratory cycle, (flow rate versus time) and total volume, the patient may be challenged to reach a goal of total inspiratory volume that was previously established and recorded on the smartphone during a training session in a doctor's office. Bluetooth® wireless technology connectivity further facilitates patient adherence to prescribed drug therapy and promotes compliance by providing a means of storing and archiving compliance information, or diagnostic data (either on the smartphone or cloud or other large network of data storage) that may be used for patient care and treatment.

More specifically, in certain embodiments, the droplet delivery device may provide automatic spray verification via LED and photodetector mechanisms. For instance, an infra-red transmitter (e.g., IR LED, or UV LED<280 nm LED), and infra-red or UV (UV with <280 nm cutoff) photodetector may be mounted along the droplet ejection side of the device to transmit an infra-red or UV beam or pulse, which detects the plume of droplets and thereby may be used for spray detection and verification. The IR or UV signal interacts with the aerosol plume and can be used to verify that a plume of droplets has been ejected as well as provide a measure of the corresponding ejected dose of medicament. Examples include but not limited to, infrared 850 nm emitters with narrow viewing angles of either, 8, 10 and 12-degrees, (MTE2087 series) or 275 nm UV LED with a GaN photodetector for aerosol plume verification in the solar blind region of the spectra. Alternatively in some applications, the sub 280 nm LEDs (e.g. 260 nm LEDs) can be used to disinfect the spacer tube 128.

By way of example, the concentration of a medicament in the ejected fluid may be made, according to Beer's Law Equation (Absorbance=e L c), where, e is the molar absorptivity coefficient (or molar extinction coefficient) which is a constant that is associated with a specific compound or formulation, L is the path length or distance between LED emitter and photodetector, and c is the concentration of the solution. This implementation provides a measure of drug concentration and can be used for verification and a means and way to monitoring patient compliance as well as to detect the successful delivery of medication.

In another embodiment, spray verification and dose verification can be monitored by measuring the transmission of 850 nM to 950 nM light across the spray in a region where the droplets are not variably diluted with different inhalation flow rates. The average and alternating signals from the detector may be measured to calibrate and confirm the optical path (average signal) and detect the spray (alternating signal). In practice, the alternating signal can be measured by a 100 Hz low-pass filter between the detector and analog converter, sampling the signal 100 to 500 times a second, calculating the average and the range (maximum minus minimum) over 100 mS periods, and comparing these values to preset values to confirm proper operation and whether there was spray or not.

This method has the strong advantages of: low power consumption (less than 1 ma to the emitter); unaffected by stray light (visible light blocking on the detector); relatively resistant to digital noise or the 100 kHz piezo drive by the 100 Hz low-pass filter; the average signal level can be used to adjust the optical path for attenuation caused by drug deposits on the LED or detector; and simple hardware with a positive signal that is robustly measured.

This system also allows simple regulation of the optical signal strength by increasing power to the emitter should the average signal level decrease. Practically, this means using pulse width modulation of emitter current to regulate average emitter power. The pulses should be at a high rate, e.g., 100 kHz, so that this noise can be removed by the 100 Hz low pass filter. Nominal operation might use a 10% duty cycle of 10 mA to achieve and average current of 1 mA. This system would have the ability to increase the average current to 10 mA and correct for up to a factor of 10 attenuation by drug deposits.

In operation with the 950 nM emitter and detector having angles of +−20 degrees and spaced 10 mm apart. With 0.5 mA emitter power, a 10K collector resistor and 100 Hz low-pass filter, the average signal output is 2 volts and the peak to peak value of the alternating component is 4 mV without spray and 40 mV during spray. Without intending to be limited, in practice, there may be a transient large peak to peak value when the spray begins and ends as the bulk attenuation causes a large shift. The resistor sizing here is for continuous running of the emitter and not PWM.

In another aspect of the disclosure, the particle delivery device may be used in connection with or integrated with breathing assist devices such as a mechanical ventilator or portable Continuous Positive Airway Pressure (CPAP) machine, to provide in-line dosing of therapeutic agents with the breathing assistance airflow.

For example, mechanical ventilators with endo-tracheal (ET) tubes are used to block secretions from entering the lungs of an unconscious patient and/or to breathe for the patient. The ET tube seals to the inside of the trachea just below the larynx with an inflatable balloon. However, common undesirable side-effects that result from use of mechanical ventilators include ventilator-assisted pneumonia (VAP), which occurs in about ⅓ of patients who are on ventilators for 48 hours or more. As a result, VAP is associated with high morbidity (20% to 30%) and increased health care systems costs. (Fernando, et al., Nebulized antibiotics for ventilation-associated pneumonia: a systematic review and meta-analysis. *Critical Care* 19:150 2015).

Tobramycin administration through the pulmonary route is generally regarded as superior to intravenous administration for treating VAP, with nebulizers being typically used to deliver the antibiotics through generation of a continuous plume of droplets into the ventilator airflow. The main benefit of inhaled versus oral or intravenous administered antibiotics is the ability to deliver a higher concentration of the antibiotic directly into the lungs. However, continuous generation of nebulizer mist provides imprecise dosing that cannot be verified between inhalation and exhalation cycles.

As such, an embodiment of the disclosure is provided wherein an in-line droplet delivery device is placed in-line with a ventilator, (for example a GE Carescape R860). The in-line droplet delivery device generates a plume of droplets as described herein, which includes a therapeutic agent such as tobramycin, which enters into the ventilator airplume near to the patient end of the endotracheal tube. In such an embodiment, the ventilator supplies a plume of inhalation air and removes a plume of exhalation air in separate tubes that merge to a single endotracheal tube close to the patient to minimize mixing of inhalations and exhalations and dead volume. The in-line droplet delivery device may be placed close to the patient end of the endotracheal tube in order to minimize loss of droplets that may stick to the tube sidewall. The patient end of the endotracheal tube is placed in a patient's throat and held in place with a balloon near the end of the tube.

Actuation of the in-line droplet delivery device is initiated at the start of an inhalation cycle. The in-line droplet delivery device can be battery powered and self-initiating breath actuated or connected to electronics that are part of the ventilator. The system may be configured so that dosing frequency and duration may be set either within the ventilator or the device. Similarly, plume generation timing and duration can be determined by the device or initiated by the ventilator. For example, the device may be programmed to dispense for half a second once every ten breaths on a continuous basis or perhaps once a minute. An in-line droplet delivery device may operate in a standalone manner or communicate the timing of dispenses and flowrates to the ventilator by a direct electrical connection or via Bluetooth® wireless technology or a similar wireless protocol.

Another aspect of the disclosure provides a system which may also be used with conventional portable CPAP machines to deliver therapeutic agents, e.g., where continuous or periodic dosing during the course of the night is valuable. In another embodiment, the in-line droplet delivery devices of the disclosure many be used in connection with a portable CPAP machine to prevent and treat cardiac events during sleep.

Typically CPAP machines use a mask to supply positive air pressure to a patient while sleeping. Applications of the in-line droplet delivery devices in conjunction with CPAP machines may provide an efficient method for continuous dosing of therapeutic agents such as antibiotics, cardiac medications, etc., for outpatient treatment of diseases, conditions, or disorders, such as pneumonia, atrial fibrillation, myocardial infarction, or any disease, condition, or disorder where continuous or periodic nighttime delivery of a medicine is desired.

In sleep apnea (SA) there are periods of not breathing and an associated decline in blood oxygen level. Not surprisingly, cardiac failure or "heart attacks" are associated with sleep apnea. This association is thought to be due to both the stress on the heart related to low oxygen levels and the increased stress on the heart as the body requires increased blood pressure and cardiac output from the heart. Additionally, there is increased risk of sleep apnea in older and overweight adults. Thus those with SA have a higher risk of heart attacks than the general population because the SA stresses the heart and because the risk factors associated with SA are very similar to the risk factors for heart attacks.

The Journal of New England in 2016 published a four-year study of the effects of CPAP on 2700 men with sleep apnea and found that CPAP significantly reduced snoring and daytime sleepiness and improved health-related quality of life and mood. (R. Doug McEvoy, et al. CPAP for Prevention of Cardiovascular Events in Obstructive Sleep Apnea, N ENGL. J. MED. 375; 10 nejm.org Sep. 8, 2016). However, the use of CPAP did not significantly reduce the number of cardiac events. The article noted that "Obstructive sleep apnea is a common condition among patients with cardiovascular disease, affecting 40 to 60% of such patients."

Many of these cardiac events can be lessened by administration of the proper medication. For example, beta blockers such as Metoprolol can lessen atrial fibrillation and the effects of myocardial infarction to sufficient extent as to prevent death in such an episode.

In certain aspects of the disclosure, the need to lessen adverse cardiac events in the population of people using CPAP devices by sensing the presence of the event and administering an ameliorating drug via pulmonary delivery is addressed. Specifically, a cardiac event may be detected by conventionally available means to detect and evaluate cardiac condition. These include heart rate monitors (such as electrical sensors held in place by an elastic band across the chest or optical monitoring at the earlobe, finger or wrist), automated blood pressure cuffs, or blood-oxygen saturation monitors on the finger or ear). When the monitor detects an adverse condition a specific dose of appropriate drug is administered by a particle delivery device of the disclosure via the CPAP tube or mask so that the drug is inhaled and carried to the blood plume via deep inhalation into the lung. Pulmonary administration is optimized both by the generation of droplets less than 5 microns in size and delivery of the droplets at the beginning of an inhalation cycle.

For example, an in-line droplet delivery device of the disclosure may be used with a CPAP machine to assist with cardiac events during sleeping. In certain aspects of the disclosure described herein, the patient may use a CPAP machine during sleep with a CPAP mask in place, wherein pressurized air is delivered to the mask by the CPAP machine. Cardiac condition may be monitored by optical measurement of the heartbeat either at finger, toe, ear lobe or the wrist. The in-line droplet delivery device may be placed in-line with the tube between the CPAP machine and the CPAP mask, or alternative may be placed at the airflow entrance of CPAP mask. Breathing is monitored by airflow measurement in the tube from the CPAP machine to the CPAP mask. Airflow rate and direction can be measured by measuring the pressure on either side of a screen which adds a slight amount of airflow restriction. Typically there will be continuous positive airflow which increases in flow rate at inspiration. A controller detects abnormal cardiac condition such as an increase in atrial fibrillation and triggers ejection of droplets of an anti-arrhythmic drug at the start of an inhalation cycle as detected by airflow in the CPAP supply tube. Information may be recorded and stored in a patient's smartphone, and various alerts may be sounded if a cardiac event is detected (e.g., transmitted via Bluetooth® wireless technology or other wireless communication methodology), if desired. Further, the patient's condition and drug dispenses may be monitored via a smartphone app, providing the patient and his medical provider with an accurate record of the patient's condition.

Other diseases commonly associated with sleep apnea, use of a mechanical ventilator, or a CPAP machine may also benefit from a system which non-invasively monitors patient condition and provides pulmonary administration of the appropriate ameliorating medication via a particle delivery device of the disclosure. For example, those with diabetes frequently are concerned that low blood sugar from a slight insulin overdose will lead to unconsciousness. In this case, abnormally low heartrate, breathing or blood pressure can be detected and sugar or insulin administered via droplets to the pulmonary system.

Without limitation, the following are exemplary operational parameters for the in-line droplet delivery device of the disclosure.

1. Device turns ON when mouthpiece cover is opened.
   a) Left green LED always on and not blinking while device is ON and no error conditions. If error condition then the LED may be different (see sections after 5-9).
   b) Device must turn OFF (lights and all actions) when cap is closed
2. Breath actuation
   a) Device must be ready to breath actuate ¼ second after the mouthpiece is open
   b) Pressure sensor is read during voice, and dispense can begin during voice.
   c) When dispense begins three green LEDs turn on. One second after dispense done chime sounds and three green LEDs blink for 9 seconds.
   d) "Close the cap" begins 10 seconds after dispense is done.
   e) Second breath actuation allowed 1 second (or more) after first dispense complete AND after pressure has dropped to very low level (first inhalation has ended). User can also press cap button (or close and then open cap) to reset device after first dispense completed to do a second breath-actuated dispense.
   f) Device "wakes up" every 8 minutes to make sure cartridge is in place and cap is closed. User does not know that device has turned on to check cap.
   g) Only four dispenses allowed each time cap is open (safety of children)
3. Dose Counter:
   a) Is reset to 200 when a new cartridge is connected.
   b) At completion of dispense the counter for that cartridge is incremented
   c) Dose counter LED is on when the device is ON. Blue LED should blink when dose counter is less than 16 doses.
   d) A method is needed to reset the dose counter for in-house testing (today it is cartridge with reset resistor)
4. Voice:
   a) Voice starts about 0.25 second after cap is opened "exhale completely and then inhale deeply".
   b) One second after dispense is done there is a chime and then "hold your breath 6 5 4 3 2 1". Then one second later "close the cap".
   c) Volume control buttons can be adjusted any time the device is turned ON
   d) Volume level is retained in memory
   e) Volume level set to high when a new cartridge is connected
   f) Voice will always have maximum volume for error messages.

5. Device left on:
a) If the device is left on for five or more seconds after the final part of "hold your breath", then the device enters the "turn off" state and remains in that state until it is turned OFF by closing the cap
b) In the "turn off" state, the device blinks the three red LEDs, makes a three harsh buzzes and voice says "close the cap" (full volume). The pattern of three buzzes and voice repeats three times and then the device turns OFF. This pattern is done every eight minutes for three cycles. Then the pattern is done once every hour.
6. Cartridge missing:
a) When device is ON and cartridge is not detected in one second (either because cartridge is missing or not making good connection), device blinks red LED (middle). Harsh buzz and voice says "no cartridge". Sequence is repeated three times with three second pause between end of voice and next harsh buzz Device then turns OFF until the cap is opened and the device then says "no cartridge" if there still is no cartridge.
b) When cartridge detected, left LED turns green and device begins "exhale completely" sequence.
7. Cartridge empty:
a) When there are sixteen or less doses remaining in cartridge, the left LED is yellow when the device turns ON. After ejection turn on three yellow LEDs and When there are 16, 8, 6, or 4 doses remaining, Voice says "replace cartridge soon" after " . . . 5, 4, 3, 2, 1". When there are two doses or less voice says "replace cartridge".
b) When there are zero doses remaining in cartridge, all LEDs are red when device is ON. Voice says "Cartridge empty"
c) When a new cartridge is inserted the counter is reset.
d) When cartridge counter is 0, there are 10 "rescue" doses available. Device operates normally for "rescue" dose use.
8. Low battery:
a) When battery voltage during dispense drops below 3.1 volts, a "low battery" flag is set. The flag is a memory location.
b) When battery voltage drops below 2.9 volts 0.1 second before the end of a dispense, a "bad battery" flag is set
c) The "low battery" flag resets when the battery reads 4.5 volts or more when the device is ON. The "bad battery" flag resets when a battery voltage above 4.0 volts is detected when the device is turned ON.
d) When "low battery" flag is ON, the device blinks the yellow battery LED and voice says "replace batteries" when turned ON. Device will still dispense during a "low battery" flag.
e) When "bad battery" flag is ON, the device blinks the red battery LED and says "replace batteries before use". The device will blink all three LEDs and will not dispense during a "bad battery" condition.
9. Evaporation/Cartridge Expiry:
a) Cumulative time a cartridge is evaporating is measured by the total time the cartridge is not on the device after the cartridge is first detected by the device plus the total time the cap has not been closed while the cartridge is connected to the device.
b) When the evaporation time for a cartridge exceeds 75 hours the dose counter for the cartridge is set to 0 and all LEDs turn on with a steady red. Voice says "replace cartridge". Ten rescue doses are allowed when the dose counter is set to 0.
c) Cartridges with ID chips will store total evaporation time and total drug dispensed.
10. Communication with smart phone:
a) Smart phone communication can only begin when the device is ON. Communication ends when the device is turned OFF and current communication is completed. Communication does not occur during dispense.

EXAMPLES

Dose Uniformity Study

Testing was performed to compare delivered-dose uniformity of the in-line droplet delivery devices of the disclosure, as illustrated in FIGS. 4A and 4B herein.

Delivered Dosage Uniformity (DDU) testing was performed to measure the amount of drug discharged from the mouthpiece of the MDI and compare that to the specified target delivered dose (TDD).

Testing was performed on equipment like that described in USP Unit Spray <601> sampling apparatus. Testing was carried out under optimized conditions of air flow rate and total air volume (drawn through the device) during the test. The volume of collection was set to not exceed 2 L at a constant flow rate of 28.3 SLPM. The total air volume was determined as 1.42 L based on the device being activated for 3 seconds at a constant flow rate of 28.3 SLPM.

The testing was performed as follows:

USP <601> recommends an air flow rate of 28.3 liters per minute (LPM) for testing delivered-dose uniformity. With the vacuum pump running, the air flow was set to 28.3 SLPM by adjusting the flow control valve and the timer was set to 3 seconds.

The device was placed on a Model XS204 Mettler-Toledo® scale (Mettler-Toledo, LLC, Columbus, Ohio) and weighed. The device was placed into the sampling apparatus. The button was pressed to activate the solenoid. The airflow of 28.3 SLPM was passed through the mouthpiece for 3 seconds. A three second duration was sufficient to ensure that the dose was completely discharged. The device was then removed from the mouthpiece adapter and weighed. The difference in weight represented the dose delivered from the device.

A summary of the spray content uniformity testing for 10 unique drug cartridges is provided in Table 1. The test is designed to demonstrate the uniformity of medication per spray consistent with the label claim for an appropriate number (n=10) of containers. The primary purpose of this test is to ensure the spray content uniformity within the same container and among multiple containers. For each cartridge, testing was performed at the maximum level of drug fill (3.0 ml) and at the minimum level of drug fill (0.45 ml). The maximum level of drug fill represents a new cartridge that has not been used by the patient. The minimum level of drug fill represents a cartridge that has been used by the patient and has only 10 doses of drug remaining. The drug was dispensed over 1.5 seconds. The testing utilized albuterol sulfate at a concentration of 8,000 µg/ml in the exemplary device and Combivent Respimat.

| Cartridge | Time | Mean (µL) | Std Dev (µL) | Min (µL) | Q1 (µL) | Med (µL) | Q3 (µL) | Max (µL) |
| --- | --- | --- | --- | --- | --- | --- | --- | --- |
| C-01 | Begin | 10.01 | 0.80 | 9.10 | 9.35 | 9.80 | 10.50 | 11.50 |
| | End | 10.08 | 0.39 | 9.30 | 9.80 | 10.20 | 10.35 | 10.60 |
| C-02 | Begin | 10.92 | 0.60 | 9.90 | 10.50 | 10.85 | 11.28 | 12.10 |
| | End | 11.24 | 0.64 | 9.90 | 10.88 | 11.55 | 11.65 | 11.90 |

-continued

| Cartridge | Time | Mean (μL) | Std Dev (μL) | Min (μL) | Q1 (μL) | Med (μL) | Q3 (μL) | Max (μL) |
|---|---|---|---|---|---|---|---|---|
| C-03 | Begin | 10.42 | 0.35 | 10.00 | 10.10 | 10.40 | 10.63 | 11.10 |
|  | End | 11.05 | 0.38 | 10.20 | 10.88 | 11.05 | 11.33 | 11.60 |
| C-04 | Begin | 9.79 | 0.33 | 9.40 | 9.48 | 9.75 | 10.05 | 10.30 |
|  | End | 8.93 | 0.34 | 8.40 | 8.58 | 9.00 | 9.18 | 9.40 |
| C-05 | Begin | 10.91 | 0.93 | 9.30 | 10.30 | 11.10 | 11.65 | 12.00 |
|  | End | 9.12 | 0.24 | 8.60 | 8.98 | 9.20 | 9.23 | 9.50 |
| C-06 | Begin | 10.08 | 0.55 | 9.40 | 9.58 | 10.00 | 10.73 | 10.80 |
|  | End | 9.22 | 0.45 | 8.60 | 8.88 | 9.10 | 9.63 | 10.00 |
| C-07 | Begin | 9.81 | 0.33 | 9.30 | 9.55 | 9.85 | 10.03 | 10.40 |
|  | End | 9.29 | 0.59 | 8.60 | 8.90 | 9.10 | 9.90 | 10.20 |
| C-08 | Begin | 9.67 | 0.63 | 8.90 | 9.10 | 9.65 | 9.93 | 11.10 |
|  | End | 9.17 | 0.41 | 8.60 | 8.85 | 9.15 | 9.45 | 9.90 |
| C-09 | Begin | 10.05 | 0.35 | 9.60 | 9.78 | 10.00 | 10.43 | 10.60 |
|  | End | 9.01 | 0.30 | 8.50 | 8.78 | 9.00 | 9.33 | 9.40 |
| C-10 | Begin | 10.71 | 0.60 | 9.60 | 10.08 | 10.90 | 11.15 | 11.30 |
|  | End | 10.48 | 0.74 | 9.60 | 9.78 | 10.45 | 11.10 | 11.60 |
| Resp-1 | Begin | 13.54 | 2.11 | 11.10 | 12.25 | 13.10 | 14.13 | 18.60 |
|  | End | 14.51 | 0.96 | 12.70 | 13.93 | 14.60 | 15.20 | 15.90 |
| Resp-2 | Begin | 14.79 | 2.83 | 11.80 | 12.45 | 13.70 | 17.03 | 20.20 |
|  | End | 14.64 | 1.27 | 12.60 | 13.10 | 15.10 | 15.40 | 16.40 |
| Resp-3 | Begin | 14.38 | 2.16 | 11.80 | 12.40 | 14.10 | 16.93 | 17.30 |
|  | End | 14.37 | 1.14 | 11.40 | 14.18 | 14.55 | 15.03 | 15.50 |

None of the determinations were outside of 80 to 120 percent of the label claim for the devices. None of the determinations were outside of 75 to 125 percent of the label claim for the devices. The mean for each of the cartridge from the beginning (n=10 determinations) and ending (n=10 determinations) were not outside of 85 to 115 percent of the label claim for the devices. All the devices met the requirements for inhalers from FDA/CDER and USP.

Delivered Dosage Uniformity (DDU) testing was performed to measure the amount of drug discharged from the mouthpiece of an exemplary device of the disclosure, and was compared to the specified target delivered dose (TDD). The target dose for the device was 10.5 μL. Testing was performed on equipment like that described in USP Unit Spray <601> sampling apparatus. Testing was carried out under optimized conditions of air flow rate and total air volume (drawn through the device) during the test. The testing demonstrated spray content uniformity within the same container (beginning and ending of drug cartridge), among multiple containers (N=10), and across 200 doses. The mean and median delivered dose across 200 samples of the device was within 0.33%. All the acceptance criteria from FDA/CDER, "Guidance for Industry: Nasal Spray and Inhalation Solution, Suspension, and Spray Drug Products—Chemistry, Manufacturing, and Controls Documentation" and USP <601>"Aerosols, Nasal Sprays, Metered-dose Inhalers, and Dry Powder Inhalers" were met.

Cascade Impactor Testing

Testing was performed to evaluate in-line droplet delivery devices of the disclosure, as illustrated in FIGS. 4A and 4B herein. The testing evaluated the devices for total drug mass output rates, aerosol particle size distributions, total drug respirable mass, delivery efficiencies, and repeatability. For aerosol particle size characterization, the study utilized two Eight-Stage Non-Viable Anderson Cascade Impactors. The impactors were flow rate monitored and controlled at 28.3 L/min for particle size characterization of disseminated Albuterol Sulfate aerosols. Following each test, impactor stage samples were extracted and recovered in solvent and analyzed for the active pharmaceutical ingredient (API) using a Thermo Scientific™ Dionex Ultimate 3000 nano-HPLC with UV detection system (Thermo Fisher Scientific Inc., Waltham, Mass.).

Exemplary devices of the disclosure were evaluated using Albuterol sulfate at a concentration of 9,818 ug/ml, which is equivalent to 8,817 ug/ml of Albuterol. The devices were tested in triplicate trials for each drug cartridge. The comparative device was tested with three (3) units that were tested singly. First testing involved single actuation content, which measured drug delivery per actuation for the device of the disclosure. Each of the three (3) cartridges were tested thirty (30) times and results were analyzed by HPLC. The cascade impactor trials involved triplicate testing for each cartridge and the comparative device for a total of twelve (12) trials. Cascade impactors were chilled to 4° C. prior to testing and the device was actuated into the cascade impactors in the 4° C. chilled environment before extracting the samples.

The study evaluated the aerosol characteristics and the delivered dose of albuterol sulfate using exemplary devices of the disclosure. The single actuation content tests involved testing three (3) cartridges a total of thirty (30) times each into the single actuation apparatus, which consists of a vacuum tube with a 47 mm filter to collect drug delivery per actuation. The filter was then analyzed by HPLC to measure total drug content. For cascade impactor tests a total of three (3) cartridges and one (1) predicate device were tested in triplicate, 0.600 ml albuterol sulfate ampoule containing a concentration of 9,818 ug/ml albuterol sulfate was added to each cartridge for the testing.

To determine the particle size distributions and respirable mass of test aerosols, inhaler test samples were collected using an Anderson Cascade Impactor (ACI) sampling at a constant 28.3 lpm during the entirety of each test. The Anderson Cascade Impactor is an FDA approved device that can be used to determine the coarse particle mass, coarse particle fraction, respirable particle mass, respirable particle fraction, fine particle mass, and fine particle fraction of test aerosols. ACI data can also be used to calculate the Mass Median Aerodynamic Diameter (MMAD) and Geometric Standard Deviation (GSD) of the aerosol size distribution. The testing was conducted using one respiratory drug: albuterol sulfate (beta-agonist bronchodilator) at a concentration of 9,818 ug/ml.

Figure 22:
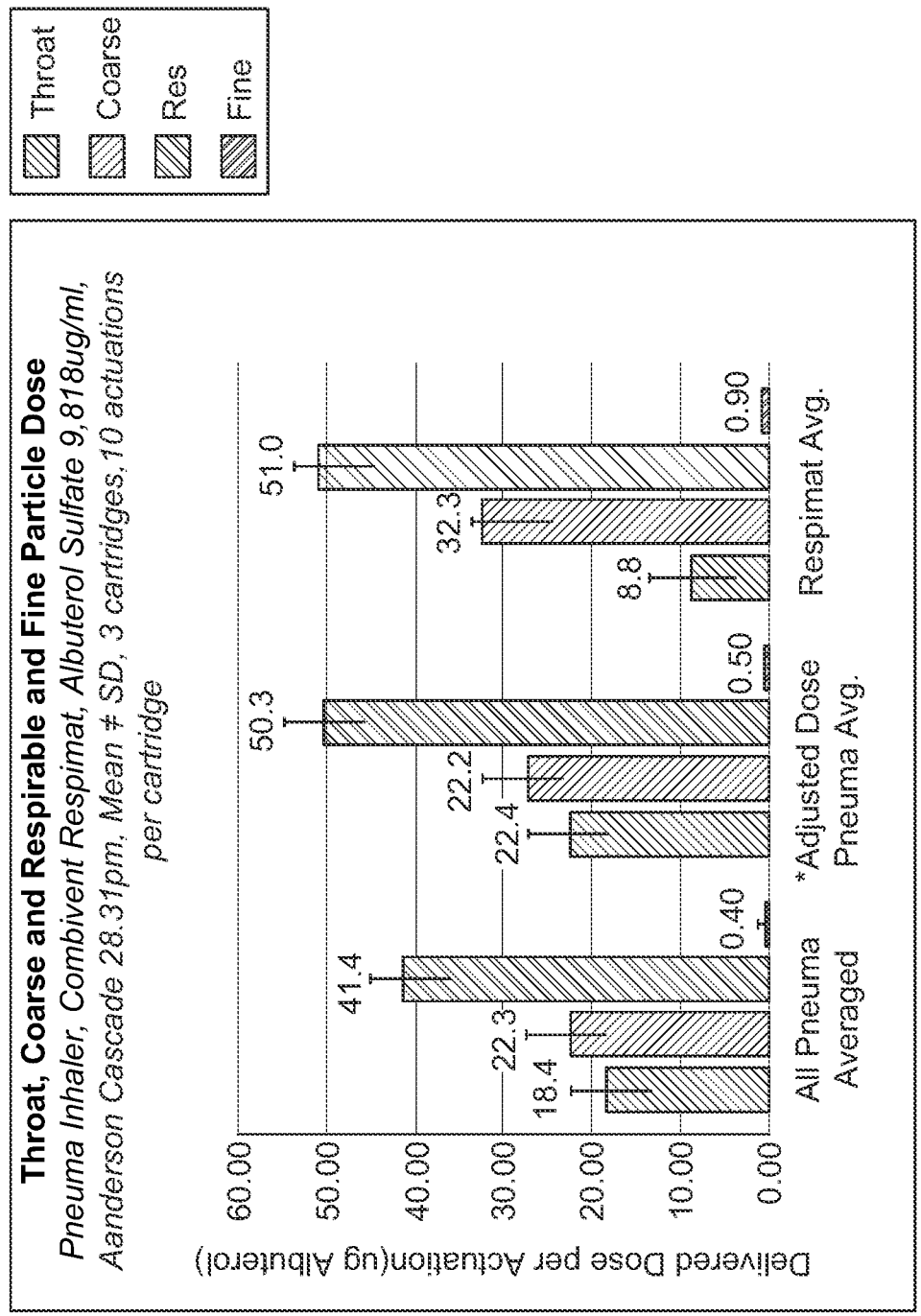

The Mouth, Throat, Coarse, Respirable and Fine Particle Dose for in-line droplet delivery devices of disclosure and comparative devices (Respimat) (Mean±SD), *Adjusted for 11,880 μg/ml Albuterol Sulfate Solution, are displayed in FIG. 22.

All publications and patent applications cited in this specification are herein incorporated by reference as if each individual publication or patent application were specifically, and individually, indicated to be incorporated by reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed:

1. An electronically actuated in-line droplet delivery device for delivering a fluid as an ejected stream of droplets to the pulmonary system of a subject, the device comprising:

a housing configured in a substantially in-line orientation;

a mouthpiece having an air entrance and positioned at an airflow exit of the device;

an air inlet flow element positioned in an airflow at an airflow entrance of the device, wherein the air inlet flow element is positioned at the air entrance of the mouthpiece;

a reservoir disposed within or in fluid communication with the housing for receiving a volume of fluid;

an electronically actuated ejector mechanism in fluid communication with the reservoir and configured to generate the ejected stream of droplets;

at least one differential pressure sensor positioned within the housing, the at least one differential pressure sensor configured to activate the ejector mechanism upon sensing a pre-determined pressure change within the mouthpiece to thereby generate the ejected stream of droplets;

the ejector mechanism comprising a piezoelectric actuator and an aperture plate, the aperture plate having a plurality of openings formed through its thickness and the piezoelectric actuator operable to oscillate the aperture plate at a frequency to thereby generate the ejected stream of droplets;

wherein the housing, air inlet flow element, and mouthpiece are configured to facilitate non-turbulent airflow across an exit side of the aperture plate and to provide sufficient airflow through the housing during use;

wherein the housing and ejector mechanism are oriented such that the exit side of the aperture plate is perpendicular to a direction of the airflow and the stream of droplets is ejected in parallel to the direction of airflow;

wherein the aperture plate and air inlet flow element are both positioned in-line along the direction of the airflow;

and wherein the ejector mechanism is configured to generate the ejected stream of droplets wherein at least about 50% of the droplets have an average ejected droplet diameter of less than about 6 microns, such that at least about 50% of the mass of the ejected stream of droplets is delivered in a respirable range to the pulmonary system of the subject during use.

2. The droplet delivery device of claim 1, wherein the air inlet flow element is positioned in front of the exit side of the aperture plate along the direction of the airflow.

3. The droplet delivery device of claim 1, wherein the air inlet flow element comprises one or more openings formed therethrough and configured to increase or decrease internal pressure resistance within the droplet delivery device during use.

4. The droplet delivery device of claim 3, wherein the air inlet flow element comprises an array of the one or more openings.

5. The droplet delivery device of claim 3, wherein the air inlet flow element comprises one or more baffles.

6. The droplet delivery device of claim 5, wherein the one or more baffles comprise the one or more openings.

7. The droplet delivery device of claim 1, wherein the aperture plate comprises a domed shape.

8. The droplet delivery device of claim 1, wherein the aperture plate is composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof.

9. The droplet delivery device of claim 1, wherein one or more of the plurality of openings have different cross-sectional shapes or diameters to thereby provide ejected droplets having different average ejected droplet diameters.

10. The droplet delivery device of claim 1, wherein the mouthpiece is removably coupled with the device.

11. The droplet delivery device of claim 1, wherein the reservoir is removably coupled with the housing.

12. The droplet delivery device of claim 1, further comprising a wireless communication module.

13. The droplet delivery device of claim 1, wherein the device further comprises one or more additional sensors selected from an infra-red transmitter, a photodetector, a pressure sensor, and combinations thereof.

14. An electronically actuated in-line droplet delivery device for delivering a fluid as an ejected stream of droplets to the pulmonary system of a subject, the device comprising:

a housing configured in a substantially in-line orientation;

a mouthpiece positioned at an airflow exit of the device;

an air inlet flow element positioned in an airflow at an airflow entrance of the device;

a reservoir disposed within or in fluid communication with the housing for receiving a volume of fluid;

an electronically actuated ejector mechanism in fluid communication with the reservoir and configured to generate the ejected stream of droplets, wherein the reservoir is coupled to the ejector mechanism to form a combination reservoir/ejector mechanism module, and the combination reservoir/ejector mechanism module is removably coupled with the housing;

at least one differential pressure sensor positioned within the housing, the at least one differential pressure sensor configured to activate the ejector mechanism upon sensing a pre-determined pressure change within the mouthpiece to thereby generate the ejected stream of droplets;

the ejector mechanism comprising a piezoelectric actuator and an aperture plate, the aperture plate having a plurality of openings formed through its thickness and the piezoelectric actuator operable to oscillate the aperture plate at a frequency to thereby generate the ejected stream of droplets;

wherein the housing, air inlet flow element, and mouthpiece are configured to facilitate non-turbulent airflow across an exit side of the aperture plate and to provide sufficient airflow through the housing during use;

wherein the housing and ejector mechanism are oriented such that the exit side of the aperture plate is perpendicular to a direction of the airflow and the stream of droplets is ejected in parallel to the direction of airflow;

wherein the aperture plate and air inlet flow element are both positioned in-line along the direction of the airflow;

and wherein the ejector mechanism is configured to generate the ejected stream of droplets wherein at least about 50% of the droplets have an average ejected droplet diameter of less than about 6 microns, such that at least about 50% of the mass of the ejected stream of droplets is delivered in a respirable range to the pulmonary system of the subject during use.

15. The droplet delivery device of claim 14, further comprising a wireless communication module.

16. The droplet delivery device of claim 14, wherein the device further comprises one or more additional sensors selected from an infra-red transmitter, a photodetector, a pressure sensor, and combinations thereof.

17. The droplet delivery device of claim 14, wherein the air inlet flow element is positioned in front of the exit side of the aperture plate along the direction of the airflow.

18. The droplet delivery device of claim 14, wherein the air inlet flow element comprises one or more openings formed therethrough and configured to increase or decrease internal pressure resistance within the droplet delivery device during use.

19. The droplet delivery device of claim 18, wherein the air inlet flow element comprises an array of the one or more openings.

20. The droplet delivery device of claim 18, wherein the air inlet flow element comprises one or more baffles.

21. The droplet delivery device of claim 20, wherein the one or more baffles comprise the one or more openings.

22. The droplet delivery device of claim 14, wherein the aperture plate comprises a domed shape.

23. The droplet delivery device of claim 14, wherein the aperture plate is composed of a material selected from the group consisting of poly ether ether ketone (PEEK), polyimide, polyetherimide, polyvinylidine fluoride (PVDF), ultra-high molecular weight polyethylene (UHMWPE), nickel, nickel-cobalt, nickel-palladium, palladium, platinum, metal alloys thereof, and combinations thereof.

24. The droplet delivery device of claim 14, wherein one or more of the plurality of openings have different cross-sectional shapes or diameters to thereby provide ejected droplets having different average ejected droplet diameters.

25. The droplet delivery device of claim 14, wherein the mouthpiece is removably coupled with the device.

26. The droplet delivery device of claim 14, wherein the reservoir is removably coupled with the housing.

\* \* \* \* \*